United States Patent
Guckian et al.

(10) Patent No.: US 9,765,016 B2
(45) Date of Patent: Sep. 19, 2017

(54) S1P MODULATING AGENTS

(71) Applicant: BIOGEN MA INC., Cambridge, MA (US)

(72) Inventors: Kevin Guckian, Northborough, MA (US); Gnanasambandam Kumaravel, Lexington, MA (US); Xiaogao Liu, Dover, MA (US); Bin Ma, Arlington, MA (US); Hairuo Peng, Needham, MA (US)

(73) Assignee: BIOGEN MA INC., Cambridge, MA (US)

( * ) Notice: Subject to any disclaimer, the term of this patent is extended or adjusted under 35 U.S.C. 154(b) by 0 days.

(21) Appl. No.: 14/763,893

(22) PCT Filed: Jan. 29, 2014

(86) PCT No.: PCT/US2014/013591
§ 371 (c)(1),
(2) Date: Jul. 28, 2015

(87) PCT Pub. No.: WO2014/120764
PCT Pub. Date: Aug. 7, 2014

(65) Prior Publication Data
US 2015/0361029 A1    Dec. 17, 2015

Related U.S. Application Data

(60) Provisional application No. 61/757,952, filed on Jan. 29, 2013, provisional application No. 61/865,846, filed on Aug. 14, 2013.

(51) Int. Cl.
| | |
|---|---|
| *C07C 229/14* | (2006.01) |
| *C07C 229/48* | (2006.01) |
| *C07C 229/50* | (2006.01) |
| *C07D 205/04* | (2006.01) |
| *C07D 207/08* | (2006.01) |
| *C07D 207/16* | (2006.01) |
| *C07D 211/34* | (2006.01) |
| *C07D 211/62* | (2006.01) |
| *A61K 31/196* | (2006.01) |
| *A61K 31/197* | (2006.01) |
| *A61K 31/198* | (2006.01) |
| *A61K 31/397* | (2006.01) |
| *A61K 31/40* | (2006.01) |
| *A61K 31/445* | (2006.01) |
| *A61K 31/695* | (2006.01) |
| *A61K 45/06* | (2006.01) |
| *C07F 7/08* | (2006.01) |

(52) U.S. Cl.
CPC .......... *C07C 229/14* (2013.01); *A61K 31/196* (2013.01); *A61K 31/197* (2013.01); *A61K 31/198* (2013.01); *A61K 31/397* (2013.01); *A61K 31/40* (2013.01); *A61K 31/445* (2013.01); *A61K 31/695* (2013.01); *A61K 45/06* (2013.01); *C07C 229/48* (2013.01); *C07C 229/50* (2013.01); *C07D 205/04* (2013.01); *C07D 207/08* (2013.01); *C07D 207/16* (2013.01); *C07D 211/34* (2013.01); *C07D 211/62* (2013.01); *C07F 7/0812* (2013.01); *C07C 2601/04* (2017.05); *C07C 2601/08* (2017.05); *C07C 2601/14* (2017.05); *C07C 2602/26* (2017.05); *C07C 2602/44* (2017.05)

(58) Field of Classification Search
CPC ... C07C 229/14; C07C 229/48; C07C 229/50; C07C 2602/26; C07C 2602/44; C07D 205/04; C07D 207/08; C07D 207/16; A61K 45/06; A61K 31/196; A61K 31/197; A61K 31/198; A61K 31/397; A61K 31/40; A61K 31/445; A61K 31/695
See application file for complete search history.

(56) References Cited

U.S. PATENT DOCUMENTS

| | | | |
|---|---|---|---|
| 4,962,224 A | 10/1990 | Wrobel et al. | |
| 5,847,194 A * | 12/1998 | Wetterich | ............ C07C 271/22 560/25 |
| 2010/0160258 A1 | 6/2010 | Caldwell et al. | |
| 2010/0305154 A1 | 12/2010 | Fitch | |
| 2012/0190649 A1 | 7/2012 | Thomas et al. | |

FOREIGN PATENT DOCUMENTS

| | | |
|---|---|---|
| GB | 1004281 A | 9/1965 |
| WO | 2012/109108 A1 | 8/2012 |

OTHER PUBLICATIONS

Edmonds, Pharmacol Ther vol. 132(3), 352-360, 2011.*
Cosconati, J Med Chem, vol. 57, 5072-5073, 2014.*
Blanchet, Antiviral Research, vol. 95, 159-166, 2012.*
Wrobel et al.; "Syntheses of Tolrestat Analogues Containing Additional Substituents in the Ring and Their Evaluation as Aldose Reductase Inhibitors Identification of Potent, Orally Active 2-Fluoro Derivatives"; Journal of Medicinal Chemistry, American Chemical Society; 34(8):2504-2520 (Aug. 1, 1991).
Jaillard et al.; "Edg8/S1P5: An Oligodendroglial Receptor with Dual Function on Process Retraction and Cell Survival"; The Journal of Neuroscience; 25(6):1459-1469 (Feb. 9, 2005).
Mattes et al.; "Design and Synthesis of Selective and Potent Orally Active S1P5 Agonists"; ChemMedChem; 5:1693-1696 (2010).

(Continued)

*Primary Examiner* — D M Seaman
(74) *Attorney, Agent, or Firm* — McCarter & English, LLP; Steven G. Davis; Xin Zhang

(57) ABSTRACT

Compounds of formula (I) can modulate the activity of one or more S 1P receptors. Sphingosine 1-phosphate (S IP) is a lysophospholipid mediator that evokes a variety of cellular responses by stimulation of five members of the endothelial cell differentiation gene (EDG) receptor family, namely S1P1, S1P2, S1P3, S1P4, and S1P5 (formerly EDG1, EDG5, EDG3, EDG6 and EDG8). The EDG receptors are G-protein coupled receptors (GPCRs) and on stimulation propagate second messenger signals via activation of heterotrimeric G-protein alpha (Ga.) subunits and beta-gamma (G( )y) dimers.

18 Claims, No Drawings

(56) References Cited

OTHER PUBLICATIONS

Miron et al.; "Fingolimond (FTY720) Enhances Remyelination Following Demyelination of Organotypic Cerebellar Slices"; The American Journal of Pathology; 176(6):2682-2694 (Jun. 2010).
Novgorodov et al.; "Activation of Sphingosine-1-Phosphate Receptor S1P5 Inhibits Oligodendrocyte Progenitor Migration"; The FASEB Journal; 21:1503-1514 (May 2007).

* cited by examiner

S1P MODULATING AGENTS

RELATED APPLICATIONS

This application is a 35 U.S.C. §371 national stage filing of International Application No. PCT/US2014/013591, filed on Jan. 29, 2014, which claims priority to U.S. Provisional Application No. 61/865,846, filed on Aug. 14, 2013, and U.S. Provisional Application No. 61/757,952, filed on Jan. 29, 2013, the entire contents of each of which are incorporated herein by reference in their entirety.

TECHNICAL FIELD

This invention relates to compounds that are S1P modulating agents, and methods of making and using such compounds.

BACKGROUND

Sphingosine 1-phosphate (SIP) is a lysophospholipid mediator that evokes a variety of cellular responses by stimulation of five members of the endothelial cell differentiation gene (EDG) receptor family, namely $S1P_1$, $S1P_2$, $S1P_3$, $S1P_4$, and $S1P_5$ (formerly EDG1, EDG5, EDG3, EDGE and EDG8). The EDG receptors are G-protein coupled receptors (GPCRs) and on stimulation propagate second messenger signals via activation of heterotrimeric G-protein alpha ($G_\alpha$) subunits and beta-gamma ($G_{\beta\gamma}$) dimers. These receptors share 50-55% amino acid sequence identity and cluster with three other structurally related lysophosphatidic acid (LPA) receptors, namely $LPA_1$, $LPA_2$, and $LPA_3$ (formerly EDG2, EDG4 and EDG7).

The recent development of agonists targeting S1P receptors has provided insight regarding the role of this signaling system in physiologic homeostasis. For example, the immunomodulating agent, FTY720 (2-amino-2-[2-(4-octylphenyl)ethyl]propane 1,3-diol), that following phosphorylation, is an agonist at 4 of 5 S1P receptors (i.e., $S1P_1$, $S1P_3$, $S1P_4$, and $S1P_5$), revealed that affecting SIP receptor activity influences lymphocyte trafficking. In particular, S1P type 4 receptors ($S1P_4$) are expressed mainly in leukocytes, and specifically $S1P_4$ mediates immunosuppressive effects of S1P by inhibiting proliferation and secretion of effector cytokines, while enhancing secretion of the suppressive cytokine IL-10. See, for example, Wang, W. et. al., (2005) FASEB J. 19(12): 1731-3, which is incorporated by reference in its entirety.

S1P type 5 receptors ($S1P_5$) are predominantly expressed in white matter tracts, oligodendrocyte precursor cells (OPCs), and remain expressed in mature myelinating oligodendrocytes. In the central nervous system, OPCs arise in restricted periventricular germinal and migrate to developing white matter where they differentiate and form myelin sheaths around axons that insulate them and enhance conduction velocity of electrical impulses. Binding of S1P to $S1P_5$ receptors has been shown to be a negative regulator of OPC motility through a Rho kinase-dependent pathway involving phosphorylation of collapsing response-mediated protein (CRMP2). In mature oligodendrocytes, however, binding of S1P to $S1P_5$ receptors results in increased cell survival, mediated through an Akt signaling pathway. (Novgorodov, A. et al., (2007) *FASEB J*, 21: 1503-1514 and Jaillard, et al., the Journal of Neuroscience (2005), 25(6): 1459-1469, both of which are incorporated by reference in their entirety). This data suggests that S1P5 receptors are involved in regulating myelination.

A number of diseases or disorders involve demyelination of the central or peripheral nervous system which can occur for a number of reasons such as immune dysfunction as in multiple sclerosis, encephalomyelitis, Guillain-Barre Syndrome, chronic inflammatory demyelinating polyneuropathy (CIDP), transverse myelitis, and optic neuritis; demyelination due to injury such as spinal cord injury, traumatic brain injury, stroke, acute ischemic optic neuropathy, or other ischemia, cerebral palsy, neuropathy (e.g. neuropathy due to diabetes, chronic renal failure, hypothyroidism, liver failure, or compression of the nerve (e.g. in Bell's palsy)), post radiation injury, and central pontine myelolysis (CPM); inherited conditions such as Charcot-Marie-Tooth disease (CMT), Sjogren-Larsson syndrome, Refsum disease, Krabbe disease, Canavan disease, Alexander disease, Friedreich's ataxia, Pelizaeus-Merzbacher disease, Bassen-Kornzweig syndrome, metachromatic leukodystrophy (MLD), adrenoleukodystrophy, and nerve damage due to pernicious anemia; viral infection such as progressive multifocal leukoencephalopathy (PML), Lyme disease, or tabes dorsalis due to untreated syphilis; toxic exposure due to chronic alcoholism (which is a possible cause of Marchiafava-Bignami disease), chemotherapy, or exposure to chemicals such as organophosphates; or dietary deficiencies such as vitamin B12 deficiency, vitamin E deficiency and copper deficiency. Other demyelination disorders may have unknown causes or multiple causes such as trigeminal neuralgia, Marchiafava-Bignami disease and Bell's palsy. One practically successful approach to treating demyelination disorders which are caused by autoimmune dysfunction has been to attempt to limit the extent of demyelination by treating the patient with immunoregulatory drugs. However, typically this approach has merely postponed but not avoided the onset of disability in these patients. Patients with demyelination due to other causes have even fewer treatment options. Therefore, the need exists to develop new treatments for patients with demyelination diseases or disorders.

Moreover, altered sphingolipid metabolism has been shown to play a role in cognitive and neurodegenerative diseases. It has been observed that the brains of patients with Alzheimer's disease, amyotrophic lateral sclerosis (ALS) and acquired immunodeficiency syndrome (AIDS) dementia have been shown to have elevated ceramide and sphingosine and low S1P compared to cognitively normal individuals. In patients with Alzheimer's disease, it has been shown that genes responsible for ceramide synthesis and S1P degradation are upregulated while genes responsible for S1P synthesis remain the same as cognitively normal individuals (Mielke, M. M. and Lyketsos, C. G., *Neuromolecular Med.* (2010), 12(4):331-340). This data suggests that high ceramide and low S1P are the hallmarks of neurodegenerative disease.

While ceramide has been shown to be pro-apoptotic, the binding of S1P to S1P receptors has been linked to resistance to apoptosis, increased cell migration and division, and oligodendrocyte differentiation and survival. Compounds which could either shift the balance of ceramide/S1P in favor of S1P-mediated survival and away from ceramide-mediated cell death or which could mimic the activity of S1P in the brain are expected to be of benefit in treating neurodegenerative and cognitive disorders.

SUMMARY

The present invention relates to compounds which modulate S1P5 receptor activity. In demyelination disorders, remyelination can occur subsequent to demyelination and can contribute to functional recovery. Remyelination is mediated by OPCs that have differentiated into myelinating cells. Compounds which modulate S1P5 receptor activity of OPCs and mature myelinating cells may be useful in stimulating remyelination leading to functional recovery in demyelination diseases and disorders. Moreover, since S1P5 receptors are expressed in the central nervous system, predominantly on oligodendrocytes and neurons, S1P5 modulators may be of therapeutic benefit in neurodegenerative and cognitive disease by shifting the ceramide/S1P balance in the brain in favor of S1P-mediated survival and/or by mimicking the activity of S1P in the brain.

In one aspect, a compound is represented by formula (I):

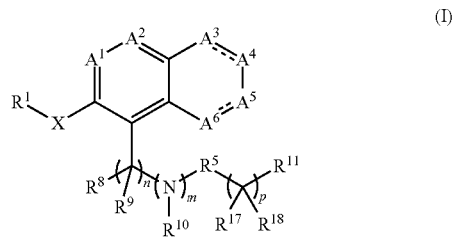

(I)

or a pharmaceutically acceptable salt thereof, wherein:

X can be O, $S(O)_r$, $NR^{12}$, $C(O)$ or $CH_2$.

$A^1$ can be $CR^2$ or N.

$A^2$ can be $CR^3$ or N.

$A^3$, $A^4$, $A^5$ and $A^6$ can each independently be $CR^2$, $C(R^2)_2$, N, or $NR^{19}$.

"- - - - -" can indicate a double or a single bond.

$R^1$ can be a $C_{6-20}$alkyl, a $C_{3-14}$carbocyclyl, a 3- to 15-membered heterocyclyl, a $C_{6-10}$aryl, or a five- to 14-membered heteroaryl, where the heterocyclyl and the heteroaryl can comprise from 1 to 10 heteroatoms independently selected from N, S or O, and where $R^1$ may be optionally substituted with from one to six independently selected $R^6$.

$R^2$ and $R^3$, for each occurrence, can be independently selected from the group consisting of hydrogen, halo, hydroxyl, nitro, cyano, carboxy, $C_{1-6}$alkyl, $C_{1-6}$haloalkyl, $C_{3-8}$cycloalkyl, $C_{3-8}$halocycloalkyl, $C_{1-6}$alkoxy, $C_{1-6}$haloalkoxy, $C_{3-8}$cycloalkoxy, $C_{3-8}$halocycloalkoxy, $C_{1-6}$alkanoyl, amino, N—($C_{1-6}$alkyl)amino, N,N-di-($C_{1-6}$alkyl)amino, $C_{1-6}$alkoxycarbonyl, $C_{1-6}$alkanoyloxy, carbamoyl, N—($C_{1-6}$alkyl)carbamoyl, N,N-di-($C_{1-6}$alkyl)carbamoyl, $C_{1-6}$alkylamido, mercapto, $C_{1-6}$alkylthio, $C_{1-6}$alkylsulfonyl, sulfamoyl, N—($C_{1-6}$alkyl)sulfamoyl, N,N-di-($C_{1-6}$alkyl)sulfamoyl, and $C_{1-6}$alkylsulfonamido.

$R^5$ can be a $C_{1-6}$alkyl, $C_{3-8}$carbocyclyl, a 3- to 8-membered heterocyclyl, $C_{6-10}$aryl, a 5- to 10-membered heteroaryl, a bridged ring system comprising from 6 to 12 ring members, a spiro ring system comprising from 5-14 ring members; or a bicyclic ring system represented by the following formula:

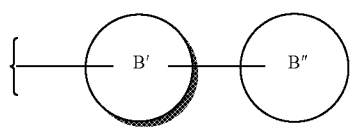

where B' and B" can be independently selected from the group consisting of monocyclic $C_{3-8}$carbocyclyl, a monocyclic 3- to 8-membered heterocyclyl, phenyl or a 5- to 6-membered heteroaryl; where $R^5$ may be optionally substituted with from 1 to 4 independently selected $R^7$.

$R^6$, for each occurrence, can be independently selected from the group consisting of halo, $C_{1-6}$alkyl, $C_{1-6}$alkoxy, $C_{1-6}$haloalkyl, $C_{3-8}$cycloalkyl, $C_{6-10}$aryl, $C_{1-6}$alkoxy-$C_{1-6}$alkyl, and tri-($C_{1-6}$alkyl)silyl; or two $R^6$ that are attached to the same carbon atom may form $C_{3-8}$spirocycloalkyl or 3- to 8-membered spiroheterocycloalkyl.

$R^7$, for each occurrence, can independently be halo, hydroxyl, nitro, cyano, $C_{1-6}$alkyl, $C_{1-6}$haloalkyl, $C_{1-6}$alkoxy, $C_{1-4}$haloalkoxy, $C_{2-6}$alkenyl, $C_{2-6}$alkynyl, $C_{3-8}$cycloalkyl, $C_{3-8}$halocycloalkyl, $C_{3-8}$cycloalkoxy, $C_{3-8}$halocycloalkoxy, —$NR^aR^b$, —$C(O)NR^aR^b$, —$N(R^a)C(O)R^b$, —$C(O)R^a$, —$S(O)_rR^a$, or —$N(R^a)S(O)_2R^b$.

$R^8$ and $R^9$ can each independently be hydrogen, a carboxy, $C_{1-6}$alkyl, or a $C_{2-6}$alkenyl; or $R^8$ and $R^9$ together with the carbon to which they are attached are —C(=O)—, a $C_{3-8}$spirocycloalkyl, or a 3- to 8-membered spiroheterocycloalkyl.

$R^{10}$ and $R^{12}$ can each, independently, be hydrogen or a $C_{1-6}$alkyl.

$R^{11}$ can be —OH, —$C(O)OR^{15}$, —$C(O)N(R^{16})_2$, —$C(O)N(R^{15})$—$S(O)_2R^{15}$, —$S(O)_2OR^{15}$, —$C(O)NHC(O)R^{15}$, —$Si(O)OH$, —$B(OH)_2$, —$N(R^{15})S(O)_2R^{15}$, —$S(O)_2N(R^{15})_2$, —O—$P(O)(OR^{15})_2$, —$P(O)(OR^{15})_2$, —CN, —$S(O)_2NHC(O)R^{15}$, —$C(O)NHS(O)_2R^{15}$, —C(O)NHOH, —C(O)NHCN, or a heteroaryl or a heterocyclyl selected from the group consisting of formulae (a)-(i'):

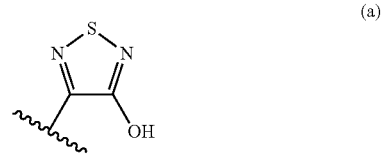

(a)

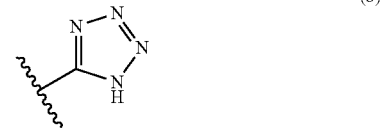

(b)

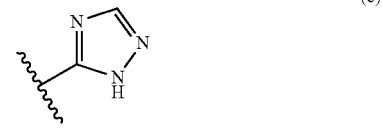

(c)

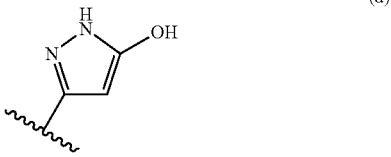

(d)

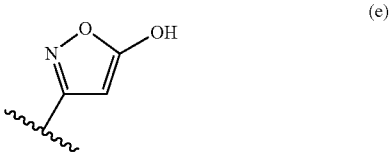

(e)

(f) 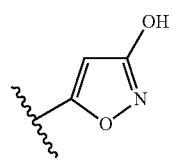
(g) 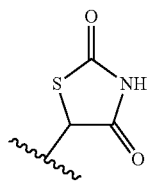
(h) 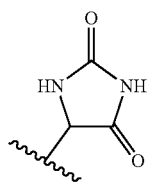
(i) 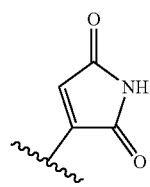
(j) 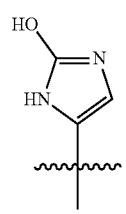
(k) 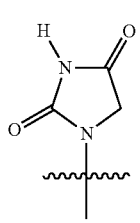
(l) 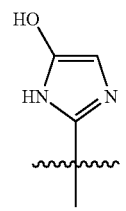
(m) 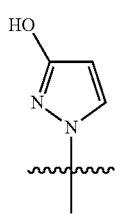
(n) 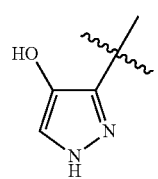
(o) 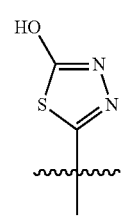
(p) 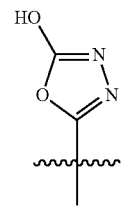
(q) 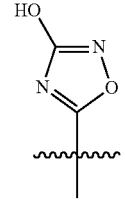
(r) 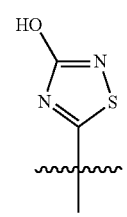
(s) 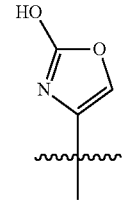
(t) 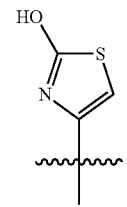

-continued
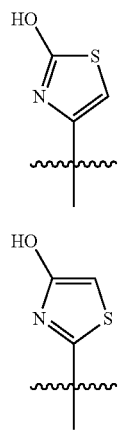
(u)
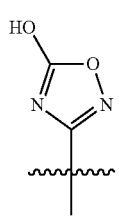
(v)
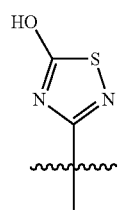
(w)
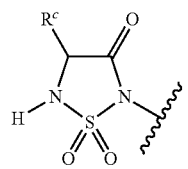
(x)
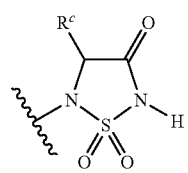
(y)
(z)
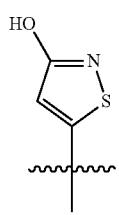
(a')
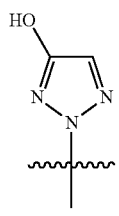
(b')
-continued
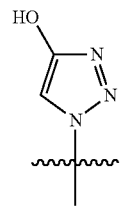
(c')
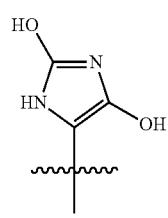
(d')
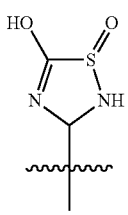
(e')
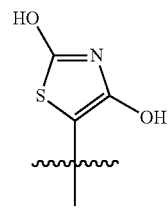
(f')
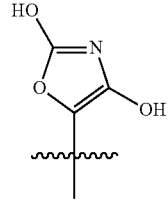
(g')
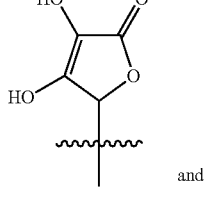
(h')
and
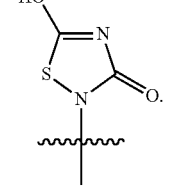
(i')
$R^{15}$ for each occurrence can be independently selected from the group consisting of hydrogen, $C_{1-8}$alkyl, $C_{2-8}$alkenyl, $C_{2-8}$alkynyl, $C_{3-8}$cycloalkyl, $C_{3-8}$cycloalkenyl, $C_{6-10}$aryl, a 5 to 14 membered heteroaryl, and a 3 to 15 membered heterocyclyl; where the heteroaryl or heterocyclyl can comprises from 1 to 10 heteroatoms independently selected from O, N, or S; and where $R^{15}$ may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—($C_{1-4}$alkyl)sulfamoyl, and N,N—($C_{1-4}$dialkyl)-sulfamoyl.

$R^{16}$ can be $R^{15}$; or two $R^{16}$ together with the nitrogen atom to which they are attached can form a 5 to 14 membered heteroaryl or a 3 to 15 membered heterocyclyl, where the heteroaryl or heterocyclyl can comprise from 1 to 10 heteroatoms independently selected from O, N, or S; and where the heteroaryl or heterocyclyl may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—$C_{1-4}$alkylsulfamoyl, and N,N—($C_{1-4}$dialkyl)-sulfamoyl.

$R^{17}$ and $R^{18}$, for each occurrence, can each independently be hydrogen, a halo, or a $C_{1-4}$haloalkyl.

$R^{19}$ for each occurrence can be independently selected from the group consisting of hydrogen, carboxy, $C_{1-6}$alkyl, $C_{1-6}$haloalkyl, $C_{3-8}$cycloalkyl, $C_{3-8}$halocycloalkyl, $C_{1-6}$alkanoyl, $C_{1-6}$alkoxycarbonyl, carbamoyl, N—($C_{1-6}$alkyl)carbamoyl, N,N-di-($C_{1-6}$alkyl)carbamoyl, $C_{1-6}$alkylsulfonyl, sulfamoyl, N—($C_{1-6}$alkyl)sulfamoyl, and N,N-di-($C_{1-6}$alkyl)sulfamoyl.

$R^a$ and $R^b$, for each occurrence, can independently be hydrogen, $C_{1-6}$alkyl, $C_{2-6}$alkenyl, $C_{2-6}$alkynyl, $C_{3-8}$cycloalkyl, $C_{6-10}$aryl, or $C_{3-8}$halocycloalkyl.

$R^c$ is hydrogen or a $C_{1-4}$alkyl.

m can be 0 or 1, provided that when m is 0, $R^5$ can comprise at least one nitrogen.

n can be an integer from 1 to 6.

p can be 0 or an integer from 1 to 6.

r, for each occurrence, can independently be 0, 1, or 2.

The compound is not:
methyl 2-(((2-((4-(tert-butyl)cyclohexyl)oxy)-4-methylnaphthalen-1-yl)methyl)amino)acetate;
2-(((2-((4-(tert-butyl)cyclohexyl)oxy)-4-methylnaphthalen-1-yl)methyl)amino)acetic acid;
4-(((2-((4-(tert-butyl)cyclohexyl)oxy)-4-methylnaphthalen-1-yl)methyl)amino)butanoic acid;
methyl 1-((2-((4-(tert-butyl)cyclohexyl)oxy)-4-methylnaphthalen-1-yl)methyl)azetidine-3-carboxylate;
1-((2-((4-(tert-butyl)cyclohexyl)oxy)-4-methylnaphthalen-1-yl)methyl)azetidine-3-carboxylic acid; ethyl 3-(((2-((4-(tert-butyl)cyclohexyl)oxy)-4-methylnaphthalen-1-yl)methyl)amino)propanoate;
3-(((2-((4-(tert-butyl)cyclohexyl)oxy)-4-methylnaphthalen-1-yl)methyl)amino)propanoic acid;
methyl 1-((2-((4-(tert-butyl)cyclohexyl)oxy)-4-methylnaphthalen-1-yl)methyl)pyrrolidine-3-carboxylate; or
1-((2-((4-(tert-butyl)cyclohexyl)oxy)-4-methylnaphthalen-1-yl)methyl)pyrrolidine-3-carboxylic acid.

In some embodiments, $R^3$ can be a halo, $C_{1-6}$alkyl, $C_{1-6}$haloalkyl or cyano. $R^5$ can be substituted by —$(CR^{17}R^{18})_p$—$R^7$ and can be optionally substituted by from 1 to 3 independently selected $R^{11}$. $R^1$ can be a cyclohexyl which can be optionally substituted with from one to three independently selected $R^6$. m can be 1 and $R^5$ can be $C_{1-6}$alkyl.

In some embodiments, m can be 0; and $R^5$ can be selected from the group consisting of:

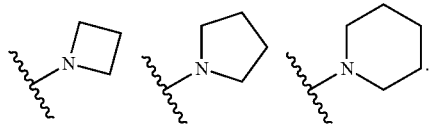

In some embodiments, $R^7$ can be COOH. $A^1$ can be $CR^2$ and $A^2$ can be $CR^3$. $A^4$ and $A^6$ can each independently be $CR^2$.

In some embodiments, $A^2$ can be $CR^3$, and each of $A^1$, $A^3$, $A^4$, $A^5$, and $A^6$, independently, can be $CR^2$.

In some embodiments, X can be O.

In another aspect, a compound can be selected from the group consisting of:
2-(((2-(((trans)-4-(tert-butyl)cyclohexyl)oxy)-4-methylnaphthalen-1-yl)methyl)amino)acetic acid;
4-(((2-(((trans)-4-(tert-butyl)cyclohexyl)oxy)-4-methylnaphthalen-1-yl)methyl)amino)butanoic acid;
1-((2-(((trans)-4-(tert-butyl)cyclohexyl)oxy)-4-methylnaphthalen-1-yl)methyl)azetidine-3-carboxylic acid;
3-(((2-(((trans)-4-(tert-butyl)cyclohexyl)oxy)-4-methylnaphthalen-1-yl)methyl)amino)propanoic acid;
1-((2-(((trans)-4-(tert-butyl)cyclohexyl)oxy)-4-methylnaphthalen-1-yl)methyl)pyrrolidine-3-carboxylic acid;
3-(((2-(((trans)-4-(tert-butyl)cyclohexyl)oxy)-4-iodonaphthalen-1-yl)methyl)amino)propanoic acid;
1-((2-(trans-4-tert-butylcyclohexyloxy)-4-methylnaphthalen-1-yl)methyl)-4-methylpiperidine-4-carboxylic acid;
4-(((2-((trans-4-(tert-butyl)cyclohexyl)oxy)-4-methylnaphthalen-1-yl)methyl)amino)bicyclo[2.2.2]octane-1-carboxylic acid;
3-(((2-((trans-4-(tert-butyl)cyclohexyl)oxy)-4-methylnaphthalen-1-yl)methyl)amino)cyclobutanecarboxylic acid;
4-(((2-((trans-4-(tert-butyl)cyclohexyl)oxy)-4-methylnaphthalen-1-yl)methyl)amino)cyclohexanecarboxylic acid;
3-(((2-((trans-4-(tert-butyl)cyclohexyl)oxy)-4-methylnaphthalen-1-yl)methyl)amino)cyclopentanecarboxylic acid;
2-(1-((2-((trans-4-(tert-Butyl)cyclohexyl)oxy)-4-methylnaphthalen-1-yl)methyl)piperidin-4-yl)acetic acid;
2-(1-((2-((trans-4-(tert-butyl)cyclohexyl)oxy)-4-methylnaphthalen-1-yl)methyl)azetidin-3-yl)acetic acid;
2-(1-((2-((trans-4-(tert-butyl)cyclohexyl)oxy)-4-methylnaphthalen-1-yl)methyl)pyrrolidin-3-yl)acetic acid;
1-((2-(cyclohexyloxy)-4-methylnaphthalen-1-yl)methyl)piperidine-4-carboxylic acid;
1-((4-methyl-2-((trans-4-(tert-pentyl)cyclohexyl)oxy)naphthalen-1-yl)methyl)piperidine-4-carboxylic acid;
1-((4-methyl-2-((trans-4-phenylcyclohexyl)oxy)naphthalen-1-yl)methyl)piperidine-4-carboxylic acid;
1-((4-methyl-2-(spiro[4.5]decan-8-yloxy)naphthalen-1-yl)methyl)piperidine-4-carboxylic acid;
1-((4-methyl-2-(spiro[5.5]undecan-3-yloxy)naphthalen-1-yl)methyl)piperidine-4-carboxylic acid;
1-((2-((cis-4-(tert-Butyl)cyclohexyl)oxy)-4-methylnaphthalen-1-yl)methyl)piperidine-4-carboxylic acid;
1-((4-methyl-2-((cis-4-methylcyclohexyl)oxy)naphthalen-1-yl)methyl)piperidine-4-carboxylic acid;
1-((2-((cis-4-Ethylcyclohexyl)oxy)-4-methylnaphthalen-1-yl)methyl)piperidine-4-carboxylic acid;
1-((4-methyl-2-((cis-4-phenylcyclohexyl)oxy)naphthalen-1-yl)methyl)piperidine-4-carboxylic acid;

1-((4-methyl-2-((trans-4-(trimethylsilyl)cyclohexyl)oxy) naphthalen-1-yl)methyl)piperidine-4-carboxylic acid;

1-((4-methyl-2-((cis-4-(trimethylsilyl)cyclohexyl)oxy) naphthalen-1-yl)methyl)piperidine-4-carboxylic acid;

1-((2-(((trans)-4-(tert-butyl)cyclohexyl)oxy)-4-(trifluoromethyl)naphthalen-1-yl)methyl)piperidine-4-carboxylic acid;

1-((2-(((trans)-4-(tert-butyl)cyclohexyl)oxy)-4-iodonaphthalen-1-yl)methyl)piperidine-4-carboxylic acid;

1-((2-(((trans)-4-(tert-butyl)cyclohexyl)oxy)-4-chloronaphthalen-1-yl)methyl)piperidine-4-carboxylic acid;

(R)-1-((6-((trans-4-(tert-Butyl)cyclohexyl)oxy)-8-methylnaphthalen-2-yl)methyl)pyrrolidine-3-carboxylic acid;

(S)-1-((2-(((trans)-4-(tert-butyl)cyclohexyl)oxy)-4-methylnaphthalen-1-yl)methyl)pyrrolidine-3-carboxylic acid; and 1-((2-(((trans)-4-(tert-butyl)cyclohexyl)oxy)-4-methylnaphthalen-1-yl)methyl)piperidine-4-carboxylic acid;

or a pharmaceutically acceptable salt thereof.

In another aspect, a pharmaceutical composition includes a pharmaceutically acceptable carrier or excipient and a compound, or a pharmaceutically acceptable salt thereof, according to formula (I).

In another aspect, a method of preventing, treating, or reducing symptoms of a condition mediated by S1P activity in a mammal, such as S1P5 activity, comprising administering to said mammal an effective amount of a compound according formula (I), or a pharmaceutically acceptable salt thereof.

In one embodiment, the condition can be selected from the group consisting of multiple sclerosis, an autoimmune disease, a chronic inflammatory disorder, asthma, an inflammatory neuropathy, arthritis, transplantation rejection, Crohn's disease, ulcerative colitis, lupus erythematosis, psoriasis, an ischemia-reperfusion injury, a solid tumor, a tumor metastasis, a disease associated with angiogenesis, a vascular disease, a pain condition, an acute viral disease, an inflammatory bowel condition, insulin-dependent diabetes, non-insulin dependent diabetes, a fibrosis of the lung, or a malignancy of the lung in a mammal. In another embodiment, the condition can be rheumatoid arthritis.

In another embodiment, the invention relates to a method of preventing, treating, or reducing symptoms of a demyelination disorder in a mammal, comprising administering to said mammal an effective amount of a compound according formula (I), or a pharmaceutically acceptable salt thereof. In one embodiment, the demyelination disorder is caused by immune dysfunction and is selected from the group consisting of multiple sclerosis, encephalomyelitis, Guillain-Barre Syndrome, chronic inflammatory demyelinating polyneuropathy (CIDP), transverse myelitis, and optic neuritis. In another embodiment, the demyelination disorder is due to injury such as spinal cord injury, traumatic brain injury, stroke, acute ischemic optic neuropathy, or other ischemia, cerebral palsy, neuropathy (e.g. neuropathy due to diabetes, chronic renal failure, hypothyroidism, liver failure, or compression of the nerve (e.g. in Bell's palsy)), post radiation injury, and central pontine myelolysis (CPM). In another embodiment, the demyelination disorder is an inherited conditions such as Charcot-Marie-Tooth disease (CMT), Sjogren-Larsson syndrome, Refsum disease, Krabbe disease, Canavan disease, Alexander disease, Friedreich's ataxia, Pelizaeus-Merzbacher disease, Bassen-Kornzweig syndrome, metachromatic leukodystrophy (MLD), adrenoleukodystrophy, and nerve damage due to pernicious anemia. In another embodiment, the demyelination disorder is a viral infection such as progressive multifocal leukoencephalopathy (PML), Lyme disease, or tabes dorsalis due to untreated syphilis. In another embodiment, the demyelination disorder is due to toxic exposure due to chronic alcoholism (which is a possible cause of Marchiafava-Bignami disease), chemotherapy, or exposure to chemicals such as organophosphates. In another embodiment, the demyelination disorder is due to a dietary deficiency such as vitamin B12 deficiency, vitamin E deficiency or copper deficiency. In another embodiment, the demyelination disorders may have unknown causes or multiple causes such as trigeminal neuralgia, Marchiafava-Bignami disease and Bell's palsy. In a specific embodiment, the demyelination disorder is multiple sclerosis.

In another embodiment, the invention relates to a method of preventing, treating, or reducing symptoms of a neurodegenerative or cognitive disease. In one embodiment, the neurodegenerative or cognitive diseases is Alzheimer's disease, ALS or AIDS dementia.

The method can further include administering to said mammal an effective amount of one or more drugs selected from the group consisting of: a corticosteroid, a bronchodilator, an antiasthmatic, an antiinflammatory, an antirheumatic, an immunosuppressant, an antimetabolite, an immunomodulating agent, an antipsoriatic, and an antidiabetic.

In another aspect, a method of preventing, treating, or reducing chronic pain in a mammal includes administering to said mammal an effective amount of a compound according to formula (I), or a pharmaceutically acceptable salt thereof.

The chronic pain can be inflammatory pain. The chronic pain can be neuropathic pain.

Other features or advantages will be apparent from the following detailed description of several embodiments, and also from the appended claims.

DETAILED DESCRIPTION

The disclosed compounds can be S1P modulating agents. In other words, the disclosed compounds can have activity as receptor agonists or receptor antagonists at one or more S1P receptors. In particular, the compounds can be S1P5 antagonists.

A compound, or a pharmaceutically acceptable salt thereof, can be represented by formula (I):

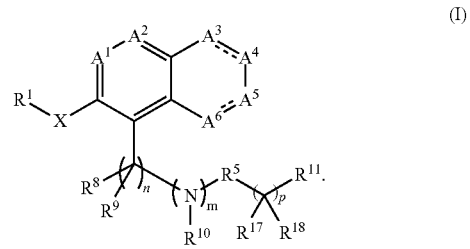

X can be O, S(O)$_r$, NR$^{12}$, C(O) or CH$_2$.
A$^1$ can be CR$^2$ or N.
A$^2$ can be CR$^3$ or N.
A$^3$, A$^4$, A$^5$ and A$^6$ can each independently be CR$^2$, C(R$^2$)$_2$, N, or NR$^{19}$.
"- - - - -" can indicate a double or a single bond.
R$^1$ can be a C$_{6-20}$alkyl, a C$_{3-14}$carbocyclyl, a 3- to 15-membered heterocyclyl, a C$_{6-10}$aryl, or a five- to 14-membered heteroaryl, where the heterocyclyl and the heteroaryl can comprise from 1 to 10 heteroatoms independently selected from N, S or O, and where $R^1$ may be optionally substituted with from one to six independently selected $R^6$.

$R^2$ and $R^3$, for each occurrence, can be independently selected from the group consisting of hydrogen, halo, hydroxyl, nitro, cyano, carboxy, $C_{1-6}$alkyl, $C_{1-6}$haloalkyl, $C_{3-8}$cycloalkyl, $C_{3-8}$halocycloalkyl, $C_{1-6}$alkoxy, $C_{1-6}$haloalkoxy, $C_{3-8}$cycloalkoxy, $C_{3-8}$halocycloalkoxy, $C_{1-6}$alkanoyl, amino, N—($C_{1-6}$alkyl)amino, N,N-di-($C_{1-6}$alkyl)amino, $C_{1-6}$alkoxycarbonyl, $C_{1-6}$alkanoyloxy, carbamoyl, N—($C_{1-6}$alkyl)carbamoyl, N,N-di-($C_{1-6}$alkyl)carbamoyl, $C_{1-6}$alkylamido, mercapto, $C_{1-6}$alkylthio, $C_{1-6}$alkylsulfonyl, sulfamoyl, N—($C_{1-6}$alkyl)sulfamoyl, N,N-di-($C_{1-6}$alkyl)sulfamoyl, and $C_{1-6}$alkylsulfonamido.

$R^5$ can be a $C_{1-6}$alkyl, $C_{3-8}$carbocyclyl, a 3- to 8-membered heterocyclyl, $C_{6-10}$aryl, a 5- to 10-membered heteroaryl, a bridged ring system comprising from 6 to 12 ring members, a spiro ring system comprising from 5-14 ring members; or a bicyclic ring system represented by the following formula:

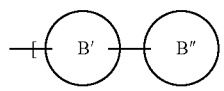

where B' and B" can be independently selected from the group consisting of monocyclic $C_{3-8}$carbocyclyl, a monocyclic 3- to 8-membered heterocyclyl, phenyl or a 5- to 6-membered heteroaryl; where $R^5$ may be optionally substituted with from 1 to 4 independently selected $R^7$.

$R^6$, for each occurrence, can be independently selected from the group consisting of halo, $C_{1-6}$alkyl, $C_{1-6}$alkoxy, $C_{1-6}$haloalkyl, $C_{3-8}$cycloalkyl, $C_{6-10}$ aryl, $C_{1-6}$alkoxy-$C_{1-6}$ alkyl, and tri-($C_{1-6}$alkyl)silyl; or two $R^6$ that are attached to the same carbon atom may form $C_{3-8}$spirocycloalkyl or 3- to 8-membered spiroheterocycloalkyl.

$R^7$, for each occurrence, can independently be halo, hydroxyl, nitro, cyano, $C_{1-6}$alkyl, $C_{1-6}$haloalkyl, $C_{1-6}$alkoxy, $C_{1-4}$haloalkoxy, $C_{2-6}$alkenyl, $C_{2-6}$alkynyl, $C_{3-8}$cycloalkyl, $C_{3-8}$halocycloalkyl, $C_{3-8}$cycloalkoxy, $C_{3-8}$halocycloalkoxy, —NR$^a$R$^b$, —C(O)NR$^a$R$^b$, —N(R$^a$)C(O)R$^b$, —C(O)R$^a$, —S(O)$_r$R$^a$, or —N(R$^a$)S(O)$_2$R$^b$.

$R^8$ and $R^9$ can each independently be hydrogen, a carboxy, $C_{1-6}$alkyl, or a $C_{2-6}$alkenyl; or $R^8$ and $R^9$ together with the carbon to which they are attached are —C(=O)—, a $C_{3-8}$spirocycloalkyl, or a 3- to 8-membered spiroheterocycloalkyl.

$R^{10}$ and $R^{12}$ can each, independently, be hydrogen or a $C_{1-6}$alkyl.

$R^{11}$ can be —OH, —C(O)OR$^{15}$, —C(O)N(R$^{16}$)$_2$, —C(O)N(R$^{15}$)—S(O)$_2$R$^{15}$, —S(O)$_2$OR$^{15}$, —C(O)NHC(O)R$^{15}$, —Si(O)OH, —B(OH)$_2$, —N(R$^{15}$)S(O)$_2$R$^{15}$, —S(O)$_2$N(R$^{15}$)$_2$, —O—P(O)(OR$^{15}$)$_2$, —P(O)(OR$^{15}$)$_2$, —CN, —S(O)$_2$NHC(O)R$^{15}$, —C(O)NHS(O)$_2$R$^{15}$, —C(O)NHOH, —C(O)NHCN, or a heteroaryl or a heterocyclyl selected from the group consisting of formulae (a)-(i'):

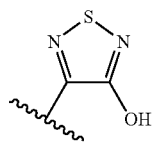
(a)

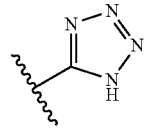
(b)

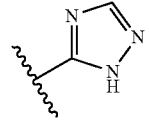
(c)

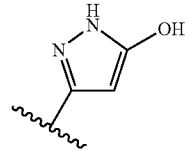
(d)

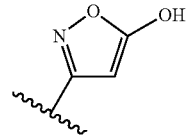
(e)

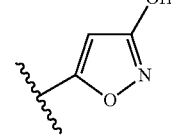
(f)

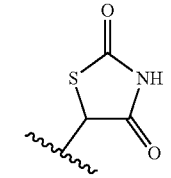
(g)

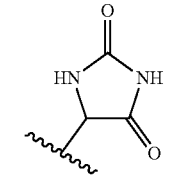
(h)

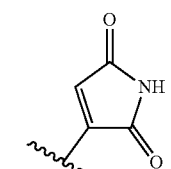
(i)

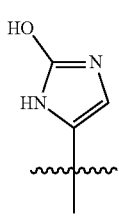
(j)

15
-continued
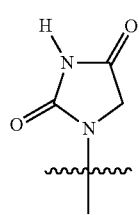 (k)
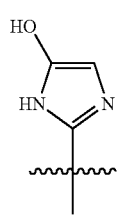 (l)
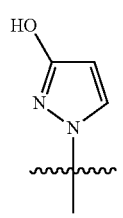 (m)
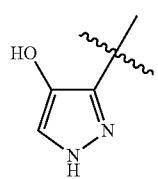 (n)
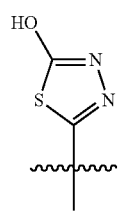 (o)
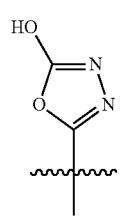 (p)
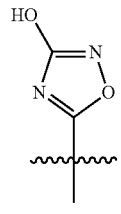 (q)
16
-continued
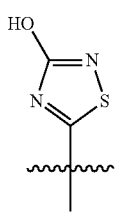 (r)
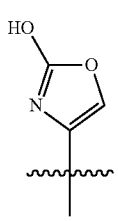 (s)
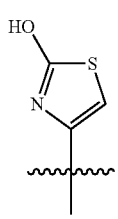 (t)
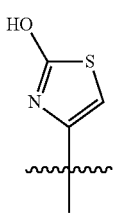 (u)
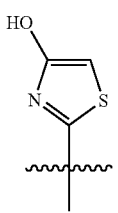 (v)
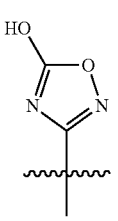 (w)
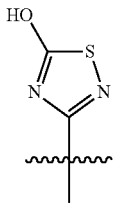 (x)

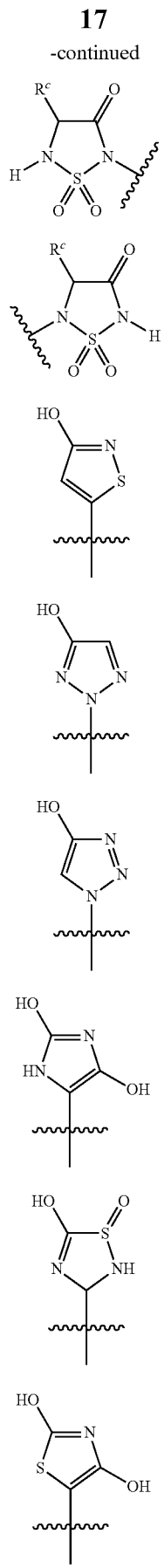
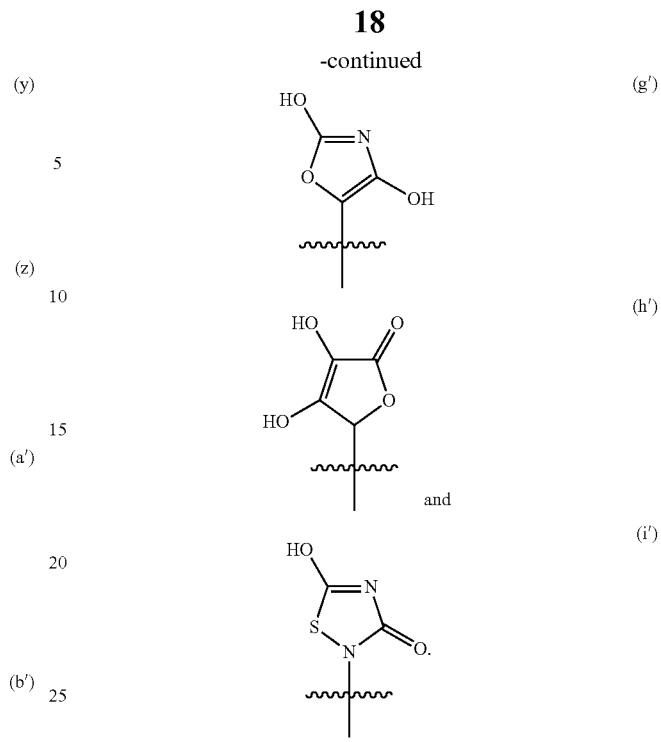

R[15] for each occurrence can be independently selected from the group consisting of hydrogen, $C_{1-8}$alkyl, $C_{2-8}$alkenyl, $C_{2-8}$alkynyl, $C_{3-8}$cycloalkyl, $C_{3-8}$cycloalkenyl, $C_{6-10}$aryl, a 5 to 14 membered heteroaryl, and a 3 to 15 membered heterocyclyl; where the heteroaryl or heterocyclyl can comprises from 1 to 10 heteroatoms independently selected from O, N, or S; and where R[15] may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—($C_{1-4}$alkyl)sulfamoyl, and N,N—($C_{1-4}$dialkyl)-sulfamoyl.

R[16] can be R[15]; or two R[16] together with the nitrogen atom to which they are attached can form a 5 to 14 membered heteroaryl or a 3 to 15 membered heterocyclyl, where the heteroaryl or heterocyclyl can comprise from 1 to 10 heteroatoms independently selected from O, N, or S; and where the heteroaryl or heterocyclyl may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—$C_{1-4}$alkylsulfamoyl, and N,N—($C_{1-4}$dialkyl)-sulfamoyl.

R[17] and R[18], for each occurrence, can each independently be hydrogen, a halo, or a $C_{1-4}$haloalkyl.

R[19] for each occurrence can be independently selected from the group consisting of hydrogen, carboxy, $C_{1-6}$alkyl, $C_{1-6}$haloalkyl, $C_{3-8}$cycloalkyl, $C_{3-8}$halocycloalkyl, $C_{1-6}$alkanoyl, $C_{1-6}$alkoxycarbonyl, carbamoyl, N—($C_{1-6}$alkyl)carbamoyl, N,N-di-($C_{1-6}$alkyl)carbamoyl, $C_{1-6}$alkylsulfonyl, sulfamoyl, N—($C_{1-6}$alkyl)sulfamoyl, and N,N-di-($C_{1-6}$alkyl)sulfamoyl.

R[a] and R[b], for each occurrence, can independently be hydrogen, $C_{1-6}$alkyl, $C_{2-6}$alkenyl, $C_{2-6}$alkynyl, $C_{3-8}$cycloalkyl, $C_{6-10}$aryl, or $C_{3-8}$halocycloalkyl.

$R^c$ is hydrogen or a $C_{1-4}$alkyl.

m can be 0 or 1, provided that when m is 0, $R^5$ can comprise at least one nitrogen.

n can be an integer from 1 to 6.

p can be 0 or an integer from 1 to 6.

r, for each occurrence, can independently be 0, 1, or 2,

The compound is not:

methyl 2-(((2-((4-(tert-butyl)cyclohexyl)oxy)-4-methylnaphthalen-1-yl)methyl)amino)acetate;

2-(((2-((4-(tert-butyl)cyclohexyl)oxy)-4-methylnaphthalen-1-yl)methyl)amino)acetic acid;

4-(((2-((4-(tert-butyl)cyclohexyl)oxy)-4-methylnaphthalen-1-yl)methyl)amino)butanoic acid;

methyl 1-((2-((4-(tert-butyl)cyclohexyl)oxy)-4-methylnaphthalen-1-yl)methyl)azetidine-3-carboxylate;

1-((2-((4-(tert-butyl)cyclohexyl)oxy)-4-methylnaphthalen-1-yl)methyl)azetidine-3-carboxylic acid;

ethyl 3-(((2-((4-(tert-butyl)cyclohexyl)oxy)-4-methylnaphthalen-1-yl)methyl)amino)propanoate;

3-(((2-((4-(tert-butyl)cyclohexyl)oxy)-4-methylnaphthalen-1-yl)methyl)amino)propanoic acid;

methyl 1-((2-((4-(tert-butyl)cyclohexyl)oxy)-4-methylnaphthalen-1-yl)methyl)pyrrolidine-3-carboxylate; or 1-((2-((4-(tert-butyl)cyclohexyl)oxy)-4-methylnaphthalen-1-yl)methyl)pyrrolidine-3-carboxylic acid.

In some embodiments, $R^3$ can be a halo, $C_{1-6}$alkyl, $C_{1-6}$haloalkyl or cyano. $R^5$ can be substituted by —$(CR^{17}R^{18})_p$—$R^7$ and can be optionally substituted by from 1 to 3 independently selected $R^{11}$. $R^1$ can be a cyclohexyl which can be optionally substituted with from one to three independently selected $R^6$. m can be 1 and $R^5$ can be $C_{1-6}$alkyl.

In some embodiments, m can be 0; and $R^5$ can be selected from the group consisting of:

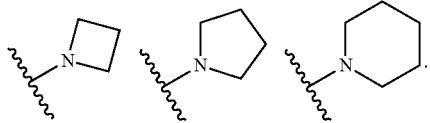

In some embodiments, $R^7$ can be COOH. $A^1$ can be $CR^2$ and $A^2$ can be $CR^3$. $A^4$ and $A^6$ can each independently be $CR^2$.

In some embodiments, $A^2$ can be $CR^3$, and each of $A^1, A^3, A^4, A^5$, and $A^6$, independently, can be $CR^2$.

In some embodiments, X can be O.

The compound can be selected from the group consisting of:

2-(((2-(((trans)-4-(tert-butyl)cyclohexyl)oxy)-4-methylnaphthalen-1-yl)methyl)amino)acetic acid;

4-(((2-(((trans)-4-(tert-butyl)cyclohexyl)oxy)-4-methylnaphthalen-1-yl)methyl)amino)butanoic acid;

1-((2-(((trans)-4-(tert-butyl)cyclohexyl)oxy)-4-methylnaphthalen-1-yl)methyl)azetidine-3-carboxylic acid;

3-(((2-(((trans)-4-(tert-butyl)cyclohexyl)oxy)-4-methylnaphthalen-1-yl)methyl)amino)propanoic acid;

1-((2-(((trans)-4-(tert-butyl)cyclohexyl)oxy)-4-methylnaphthalen-1-yl)methyl)pyrrolidine-3-carboxylic acid;

3-(((2-(((trans)-4-(tert-butyl)cyclohexyl)oxy)-4-iodonaphthalen-1-yl)methyl)amino)propanoic acid;

1-((2-(trans-4-tert-butylcyclohexyloxy)-4-methylnaphthalen-1-yl)methyl)-4-methylpiperidine-4-carboxylic acid;

4-(((2-((trans-4-(tert-butyl)cyclohexyl)oxy)-4-methylnaphthalen-1-yl)methyl)amino)bicyclo[2.2.2]octane-1-carboxylic acid;

3-(((2-((trans-4-(tert-butyl)cyclohexyl)oxy)-4-methylnaphthalen-1-yl)methyl)amino)cyclobutanecarboxylic acid;

4-(((2-((trans-4-(tert-butyl)cyclohexyl)oxy)-4-methylnaphthalen-1-yl)methyl)amino)cyclohexanecarboxylic acid;

3-(((2-((trans-4-(tert-butyl)cyclohexyl)oxy)-4-methylnaphthalen-1-yl)methyl)amino)cyclopentanecarboxylic acid;

2-(1-((2-((trans-4-(tert-Butyl)cyclohexyl)oxy)-4-methylnaphthalen-1-yl)methyl)piperidin-4-yl)acetic acid;

2-(1-((2-((trans-4-(tert-butyl)cyclohexyl)oxy)-4-methylnaphthalen-1-yl)methyl)azetidin-3-yl)acetic acid;

2-(1-((2-((trans-4-(tert-butyl)cyclohexyl)oxy)-4-methylnaphthalen-1-yl)methyl)pyrrolidin-3-yl)acetic acid;

1-((2-(cyclohexyloxy)-4-methylnaphthalen-1-yl)methyl)piperidine-4-carboxylic acid;

1-((4-methyl-2-((trans-4-(tert-pentyl)cyclohexyl)oxy)naphthalen-1-yl)methyl)piperidine-4-carboxylic acid;

1-((4-methyl-2-((trans-4-phenylcyclohexyl)oxy)naphthalen-1-yl)methyl)piperidine-4-carboxylic acid;

1-((4-methyl-2-(spiro[4.5]decan-8-yloxy)naphthalen-1-yl)methyl)piperidine-4-carboxylic acid;

1-((4-methyl-2-(spiro[5.5]undecan-3-yloxy)naphthalen-1-yl)methyl)piperidine-4-carboxylic acid;

1-((2-((cis-4-(tert-Butyl)cyclohexyl)oxy)-4-methylnaphthalen-1-yl)methyl)piperidine-4-carboxylic acid;

1-((4-methyl-2-((cis-4-methylcyclohexyl)oxy)naphthalen-1-yl)methyl)piperidine-4-carboxylic acid;

1-((2-((cis-4-Ethylcyclohexyl)oxy)-4-methylnaphthalen-1-yl)methyl)piperidine-4-carboxylic acid;

1-((4-Methyl-2-((cis-4-phenylcyclohexyl)oxy)naphthalen-1-yl)methyl)piperidine-4-carboxylic acid;

1-((4-methyl-2-((trans-4-(trimethylsilyl)cyclohexyl)oxy)naphthalen-1-yl)methyl)piperidine-4-carboxylic acid;

1-((4-methyl-2-((cis-4-(trimethylsilyl)cyclohexyl)oxy)naphthalen-1-yl)methyl)piperidine-4-carboxylic acid;

1-((2-(((trans)-4-(tert-butyl)cyclohexyl)oxy)-4-(trifluoromethyl)naphthalen-1-yl)methyl)piperidine-4-carboxylic acid;

1-((2-(((trans)-4-(tert-butyl)cyclohexyl)oxy)-4-iodonaphthalen-1-yl)methyl)piperidine-4-carboxylic acid;

1-((2-(((trans)-4-(tert-butyl)cyclohexyl)oxy)-4-chloronaphthalen-1-yl)methyl)piperidine-4-carboxylic acid;

(R)-1-((6-(((trans-4-(tert-Butyl)cyclohexyl)oxy)-8-methylnaphthalen-2-yl)methyl)pyrrolidine-3-carboxylic acid;

(S)-1-((2-(((trans)-4-(tert-butyl)cyclohexyl)oxy)-4-methylnaphthalen-1-yl)methyl)pyrrolidine-3-carboxylic acid; and 1-((2-(((trans)-4-(tert-butyl)cyclohexyl)oxy)-4-methylnaphthalen-1-yl)methyl)piperidine-4-carboxylic acid;

or a pharmaceutically acceptable salt thereof.

The term "fused ring system," as used herein, is a ring system that has two or three rings (preferably two rings) independently selected from carbocyclyl, heterocyclyl, aryl or heteroaryl rings that share one side. A fused ring system may have from 4-15 ring members, preferably from 5-10 ring members. Examples of fused ring systems include octahydroisoquinolin-2(1H)-yl, 2,3-dihydro-1H-indenyl, octahydro-1H-pyrido[1,2-a]pyrazinyl, and decahydroisoquinolinyl).

The term "bridged ring system," as used herein, is a ring system that has a carbocyclyl or heterocyclyl ring wherein two non-adjacent atoms of the ring are connected (bridged) by one or more (preferably from one to three) atoms selected from C, N, O, or S. A bridged ring system can have more than one bridge within the ring system (e.g., adamantyl). A bridged ring system may have from 6-10 ring members, preferably from 7-10 ring members. Examples of bridged ring systems include adamantyl, 9-azabicyclo[3.3.1]nonan-9-yl, 8-azabicyclo[3.2.1]octanyl, bicyclo[2.2.2]octanyl, 3-azabicyclo[3.1.1]heptanyl, bicyclo[2.2.1]heptanyl, (1R, 5S)-bicyclo[3.2.1]octanyl, 3-azabicyclo[3.3.1]nonanyl, and bicyclo[2.2.1]heptanyl. More preferably, the bridged ring system is selected from the group consisting of 9-azabicyclo [3.3.1]nonan-9-yl, 8-azabicyclo[3.2.1]octanyl, and bicyclo [2.2.2]octanyl.

The term "spiro ring system," as used herein, is a ring system that has two rings each of which are independently selected from a carbocyclyl or a heterocyclyl, wherein the two ring structures having one atom in common. Spiro ring systems have from 5 to 14 ring members. Example of spiro ring systems include 2-azaspiro[3.3]heptanyl, spiropentanyl, 2-oxa-6-azaspiro[3.3]heptanyl, 2,7-diazaspiro[3.5]nonanyl, 2-oxa-7-azaspiro[3.5]nonanyl, 6-oxa-9-azaspiro[4.5]decanyl, 6-oxa-2-azaspiro[3.4]octanyl, 5-azaspiro[2.3]hexanyl and 2,8-diazaspiro[4.5]decanyl.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 6 carbon atoms, or 1 to 4 carbon atoms. In some embodiments, an alkyl comprises from 6 to 20 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, or n-decyl.

"Alkylene" refers to a divalent alkyl group. Examples of alkylene groups include methylene, ethylene, propylene, n-butylene, and the like. The alkylene is attached to the rest of the molecule through a single bond and to the radical group through a single bond. The points of attachment of the alkylene to the rest of the molecule and to the radical group can be through one carbon or any two carbons within the carbon chain.

As used herein, the term "haloalkyl" refers to an alkyl, as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro substituent. Dihaloalkyl and polyhaloalkyl groups can be substituted with two or more of the same halo atoms or a combination of different halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms. Preferred haloalkyl groups are trifluoromethyl and difluoromethyl.

"Halogen" or "halo" may be fluoro, chloro, bromo or iodo.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-6 carbon atoms, more preferably about 1-4 carbon atoms.

As used herein, the term "haloalkoxy" refers to haloalkyl-O—, wherein haloalkyl is defined herein above. Representative example of haloalkoxy groups are trifluoromethoxy, difluoromethoxy, and 1,2-dichloroethoxy. Preferably, haloalkoxy groups have about 1-6 carbon atoms, more preferably about 1-4 carbon atoms.

As used herein, the term "alkylthio" refers to alkyl-S—, wherein alkyl is defined herein above.

As used herein, the term "carbocyclyl" refers to saturated or partially unsaturated (but not aromatic) monocyclic, bicyclic or tricyclic hydrocarbon groups of 3-14 carbon atoms, preferably 3-9, or more preferably 3-8 carbon atoms. Carbocyclyls include fused or bridged ring systems. The term "carbocyclyl" encompasses cycloalkyl groups. The term "cycloalkyl" refers to completely saturated monocyclic, bicyclic or tricyclic hydrocarbon groups of 3-12 carbon atoms, preferably 3-9, or more preferably 3-8 carbon atoms. Exemplary monocyclic carbocyclyl groups include, but are not limited to, cyclopropyl, cyclobutyl, cyclopentyl, cyclopentenyl, cyclohexyl or cyclohexenyl. Exemplary bicyclic carbocyclyl groups include bornyl, decahydronaphthyl, bicyclo[2.1.1]hexyl, bicyclo[2.2.1]heptyl, bicyclo[2.2.1] heptenyl, 6,6-dimethylbicyclo[3.1.1]heptyl, 2,6,6-trimethylbicyclo[3.1.1]heptyl, or bicyclo[2.2.2]octyl. Exemplary tricyclic carbocyclyl groups include adamantyl.

As used herein, the term "halocycloalkyl" refers to a cycloalkyl, as defined herein, that is substituted by one or more halo groups as defined herein. Preferably the halocycloalkyl can be monohalocycloalkyl, dihalocycloalkyl or polyhalocycloalkyl including perhalocycloalkyl. A monohalocycloalkyl can have one iodo, bromo, chloro or fluoro substituent. Dihalocycloalkyl and polyhalocycloalkyl groups can be substituted with two or more of the same halo atoms or a combination of different halo groups.

As used herein, the term "cycloalkoxy" refers to cycloalkyl-O—, wherein cycloalkyl is defined herein above.

As used herein, the term "halocycloalkoxy" refers to halocycloalkyl-O—, wherein halocycloalkyl is defined herein above.

The term "spirocycloalkyl" as used herein, is a cycloalkyl that has one ring atom in common with the group to which it is attached. Spirocycloalkyl groups may have from 3 to 14 ring members. In a preferred embodiment, the spirocycloalkyl has from 3 to 8 ring carbon atoms and is monocyclic.

The term "aryl" refers to monocyclic, bicyclic or tricyclic aromatic hydrocarbon groups having from 6 to 14 carbon atoms in the ring portion. In one embodiment, the term aryl refers to monocyclic and bicyclic aromatic hydrocarbon groups having from 6 to 10 carbon atoms. Representative examples of aryl groups include phenyl, naphthyl, fluorenyl, and anthracenyl.

The term "aryl" also refers to a bicyclic or tricyclic group in which at least one ring is aromatic and is fused to one or two non-aromatic hydrocarbon ring(s). Nonlimiting examples include tetrahydronaphthalene, dihydronaphthalenyl and indanyl.

As used herein, the term "heterocyclyl" refers to a saturated or unsaturated, non-aromatic monocyclic, bicyclic or tricyclic ring system which has from 3- to 15-ring members at least one of which is a heteroatom, and up to 10 of which may be heteroatoms, wherein the heteroatoms are independently selected from O, S and N, and wherein N and S can be optionally oxidized to various oxidation states. In one embodiment, a heterocyclyl is a 3-8-membered monocyclic. In another embodiment, a heterocyclyl is a 6-12-membered bicyclic. In yet another embodiment, a heterocyclycyl is a 10-15-membered tricyclic ring system. The heterocyclyl group can be attached at a heteroatom or a carbon atom. Heterocyclyls include fused or bridged ring systems. The term "heterocyclyl" encompasses heterocycloalkyl groups. The term "heterocycloalkyl" refers to completely saturated monocyclic, bicyclic or tricyclic heterocyclyl comprising 3-15 ring members, at least one of which is a heteroatom, and up to 10 of which may be heteroatoms, wherein the heteroatoms are independently selected from O, S and N, and wherein N and S can be optionally oxidized to various oxidation states. Examples of heterocyclyls include dihydrofuranyl, [1,3]dioxolane, 1,4-dioxane, 1,4-dithiane, piperazinyl, 1,3-dioxolane, imidazolidinyl, imidazolinyl, pyrrolidine, dihydropyran, oxathiolane, dithiolane, l,3-dioxane, 1,3-dithianyl, oxathianyl, thiomorpholinyl, oxiranyl, aziridinyl, oxetanyl, azetidinyl, tetrahydrofuranyl, pyrrolidinyl, tetrahydropyranyl, piperidinyl, morpholinyl, piperazinyl, azepinyl, oxapinyl, oxazepinyl and diazepinyl.

The term "spiroheterocycloalkyl" as used herein, is a heterocycloalkyl that has one ring atom in common with the group to which it is attached. Spiroheterocycloalkyl groups may have from 3 to 15 ring members. In a preferred embodiment, the spiroheterocycloalkyl has from 3 to 8 ring atoms selected from carbon, nitrogen, sulfur and oxygen and is monocyclic.

As used herein, the term "heteroaryl" refers to a 5-14 membered monocyclic-, bicyclic-, or tricyclic-ring system, having 1 to 10 heteroatoms independently selected from N, O or S, wherein N and S can be optionally oxidized to various oxidation states, and wherein at least one ring in the ring system is aromatic. In one embodiment, the heteroaryl is monocyclic and has 5 or 6 ring members. Examples of monocyclic heteroaryl groups include pyridyl, thienyl, furanyl, pyrrolyl, pyrazolyl, imidazoyl, oxazolyl, isoxazolyl, thiazolyl, isothiazolyl, triazolyl, oxadiazolyl, thiadiazolyl and tetrazolyl. In another embodiment, the heteroaryl is bicyclic and has from 8 to 10 ring members. Examples of bicyclic heteroaryl groups include indolyl, benzofuranyl, quinolyl, isoquinolyl indazolyl, indolinyl, isoindolyl, indolizinyl, benzamidazolyl, quinolinyl, 5,6,7,8-tetrahydroquinoline and 6,7-dihydro-5H-pyrrolo[3,2-d]pyrimidine.

An amino is a group having the formula $NH_2$—. The term N-alkylamino is an amino group in which one of the hydrogen atoms is replaced with an alkyl group. The term N,N-dialkylamino is an amino group in which each hydrogen atoms is replaced with an alkyl group which may be the same or different.

The term "alkanoyl" refers to alkyl-C(O)— wherein the alkyl is defined as above.

The term "alkoxycarbonyl" refers to alkoxy-C(O)—, wherein the alkoxy group is defined as above.

The term "alkanoyloxy" refers to alkyl-C(O)O—, wherein the alkyl is defined as above.

A carbamoyl is a group having the formula $NH_2C(O)$—. The term N-alkylcarbamoyl is a carbamoyl group in which one of the hydrogen atoms is replaced with an alkyl group. The term N,N-dialkylcarbamoyl is a carbamoyl group in which each hydrogen atoms is replaced with an alkyl group which may be the same or different.

The term "alkylamido" refers to a group having the formula alkyl-C(O)—NH—. As used herein, the term "alkylsulfonyl" refers to a group having the formula alkyl-$SO_2$—.

A sulfamoyl is a group having the formula $NH_2S(O)_2$—. The term N-alkylsulfamoyl is a sulfamoyl group in which one of the hydrogen atoms is replaced with an alkyl group.

The term N,N-dialkylsulfamoyl is a sulfamoyl group in which each hydrogen atoms is replaced with an alkyl group which may be the same or different.

The term "alkylsulfonamido" refers to a group having the formula alkyl-$S(O)_2$—NH—.

The term "trialkylsilyl" refers to (alkyl)$_3$-Si—, wherein each of the alkyl groups may be the same or different.

The number of carbon atoms in a group is specified herein by the prefix "$C_{x-xx}$", wherein x and xx are integers. For example, "$C_{1-4}$alkyl" is an alkyl group which has from 1 to 4 carbon atoms; $C_{1-6}$alkoxy is an alkoxy group having from 1 to 6 carbon atoms; $C_{6-10}$aryl is an aryl group which has from 6 to 10 carbon atoms; $C_{1-4}$haloalkyl is a haloalkyl group which has from 1 to 4 carbon atoms; and N,N-di-$C_{1-6}$alkylamino is a N,N-dialkylamino group in which the nitrogen is substituted with two alkyl groups each of which is independently from 1 to 6 carbon atoms.

The disclosed compounds can contain one or more asymmetric centers in the molecule. In accordance with the present disclosure any structure that does not designate the stereochemistry is to be understood as embracing all the various optical isomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis, or chromatographic separation using a chiral stationary phase). The compounds can be isotopically-labeled compounds, for example, compounds including various isotopes of hydrogen, carbon, nitrogen, oxygen, phosphorous, fluorine, iodine, or chlorine. The disclosed compounds may exist in tautomeric forms and mixtures and separate individual tautomers are contemplated. In addition, some compounds may exhibit polymorphism.

A compound of formula (I) can modulate the activity of S1P receptors. A compound of formula (I) can have S1P receptor agonist or antagonist activity. The compound can be selective for the S1P5 receptor. In one embodiment, the compound can be a selective S1P5 antagonist. In another embodiment, the compound can be a selective S1P5 agonist. Being selective can mean that the compound binds to the receptor (or relatively small group of related molecules or proteins) in a complex mixture, or in other words, when exposed to a variety of closely related receptor types, the compound can bind preferentially to just one of the receptor types.

The compound can have a greater affinity for the S1P5 receptor, by at least 2-fold, by at least 5-fold, by at least 10-fold, by at least 50-fold, by at least 100-fold, or by at least 1000-fold, than for S1P1 receptor, S1P2 receptor, S1P3 receptor, or S1P4 receptor.

An inhibitor of S1P5 mediated activity can block S1P interaction with an S1P5 receptor. For example, the inhibitor can be an antagonist of an S1P5 receptor. An antagonist can be a molecule that has affinity for the receptor but does not induce activity or a specific activity from the receptor. The antagonist can bind with an S1P5 receptor with an $IC_{50}$ value of less than 1 µM, less than 750 nM, less than 500 nM, less than 250 nM or less than 100 nM. The antagonist can bind with an S1P5 receptor with an $IC_{50}$ value in a range between 1 nM and 1 µM, between 1 nM and 500 nM, between 10 nM and 250 nM, between 25 nm and 100 nM, or between 50 nM and 100 nM.

In some cases, the compounds can also promote oligodendrocyte progenitor cell differentiation. The compounds can promote myelination or remyelination.

S1P binding to the S1P5 receptor can inhibit cell migration. For example, S1P binding specifically to the S1P5 receptor blocks OPC migration. See, for example, Novgorodov, A. S., et al., "Activation of sphingosine-1-phosphate receptor S1P5 inhibits oligodendrocyte progenitor migration," FASEB J. 21, 1503-1514 (2007), which is incorporated by reference in its entirety. Thus S1P may be a part of the neuron-oligodendroglial communication network regulating OPC migration and may provide directional guidance cues for migrating OPCs in the developing brain.

In addition, the S1P-mediated proliferation response of human esophageal cancer cells was lower when transfected with S1P5 (Hu, W.-M., et al., "Effect of S1P5 on proliferation and migration of human esophageal cancer cells," World J. Gastroenterol. 16, 1859-1866 (2010), which is incorporated by reference in its entirety). Thus, in some cases, the compounds can inhibit cell migration, including migration of OPCs.

S1P5 expression can affect cell migration in other ways. S1P5 deficient mice exhibit a defect in the egress of natural killer cells from lymph nodes. See Jenne, C. N., et al., "T-bet-dependent S1P5 expression in NK cells promotes egress from lymph nodes and bone marrow," J. Exp. Med 206, 2469-2481 (2009), which is incorporated by reference in its entirety. S1P5 also contributes to formation of the blood brain barrier and maintaining immune quiescence of the endothelial cells of the barrier. See van Doom, R., et al., "Sphingosine 1-phosphate receptor 5 mediates the immune quiescence of the human brain endothelial barrier," J. Neuroinflammation, 9:133 (2012), which is incorporated by reference in its entirety.

An "SIP modulating agent" refers a compound or composition that is capable of inducing a detectable change in S1P receptor activity in vivo or in vitro (e.g., at least 10% increase or decrease in S1P receptor activity as measured by a given assay such as the assays described in the examples and known in the art. "SIP receptor," refers to all of the S1P receptor subtypes (for example, the S1P receptors S1P1, S1P2, S1P3, S1P4, or S1P5), unless the specific subtype is indicated. It is well known in the art how to determine S1P agonist or antagonist activity using the standard tests described herein, or using other similar tests which are well known in the art. In some cases, depending on the cell type and conditions used, an S1P modulating agent can have agonist or antagonist activity, even at the same receptor subtype.

The biological effects of an S1P modulating agent vary depending on whether the compound has S1P receptor agonist or antagonist activity. Potential uses of an S1P modulating agent include, but are not limited to, prevention or treatment of a pathological condition or symptom in a mammal. For example, the condition can include asthma, an inflammatory neuropathies, arthritis, lupus erythematosis, psoriasis, an ischemia reperfusion injury, a solid tumor, a tumor metastasis, a disease associated with angiogenesis, a vascular disease, a pain condition, an acute viral disease, or insulin-dependent diabetes, and non-insulin dependent diabetes. The condition can alter lymphocyte trafficking as a method of treatment for neuropathic pain, inflammation-induced pain (e.g., where prostaglandins are involved) or treatment of autoimmune pathologies such as uveitis, type I diabetes, rheumatoid arthritis, chronic inflammatory disorders, inflammatory bowel diseases (e.g., Crohn's disease and ulcerative colitis), and multiple sclerosis. In addition, S1P modulating compounds may be useful in drug-eluting stents to reduce inflammation. Additional uses can include treatment of brain degenerative diseases, heart diseases, cancers, or hepatitis C. See, for example, WO 2005/085295, WO 2004/010987, WO 03/097028, and WO 2006/072562, each of which is incorporated by reference in its entirety. A class of S1P receptor agonists are described in provisional U.S. Application No. 60/956,111, filed Aug. 15, 2007, and PCT/US2008/073378, filed Aug. 15, 2008, each of which is incorporated by reference in its entirety. See also provisional U.S. Application No. 61/231,539, filed Aug. 5, 2009, and PCT/US2010/44607, filed Aug. 5, 2010, each of which is incorporated by reference in its entirety. See also provisional U.S. Application No. 61/440,254, filed Feb. 7, 2011, and PCT/US2012/23799 filed Feb. 6, 2012, each of which is incorporated by reference in its entirety.

Additional potential uses of an S1P modulating agent include, but are not limited to, prevention or treatment of a pathological condition or symptom in a mammal. In one embodiment, the pathological condition is treated or prevented by inhibited cell migration of OPCs. In another embodiment, the pathological condition is treated or prevented by promoting the survival of oligodendrocytes.

Potential uses of an S1P receptor antagonist or agonist, and S1P5 receptor type selective antagonists or agonist particularly, include, but are not limited to, prevention or treatment of a pathological condition or symptom in a mammal.

LPA has been shown to be involved in lymphocyte trafficking and helps promote entry of lymphocytes into secondary lymphoid organs (see Kanda, et al., Nat. Immunology (2008), 9:415-423). Therefore, the disclosed compounds are expected to be useful for altering lymphocyte trafficking as a method for prolonging allograft survival, for example transplantation including solid organ transplants, treatment of graft vs. host disease, bone marrow transplantation, and the like.

In addition, disclosed compounds can be useful as antagonists of the cannabinoid $CB_1$ receptor. $CB_1$ antagonism is associated with a decrease in body weight and an improvement in blood lipid profiles. The $CB_1$ antagonism could be in concert with S1P receptor activity, or be independent of activity at any S1P receptor.

In addition, disclosed compounds can be useful for inhibition of group IVA cytosolic $PLA_2$ ($cPLA_2$). $cPLA_2$ catalyzes the release of eicosanoic acids (e.g., arachidonic acid). The eicosanoic acids are transformed to pro-inflammatory eicosanoids such as prostaglandins and leukotrienes. Thus, disclosed compounds may be useful as anti-inflammatory agents. This inhibition could be in concert with SIP receptor activity, or be independent of activity at any S1P receptor.

In addition, disclosed compounds may be useful for inhibition of the multiple substrate lipid kinase (MuLK). MuLK is highly expressed in many human tumor cells and thus its inhibition might slow the growth or spread of tumors.

Neurological Disorders $S1P_5$ receptors are predominantly expressed in white matter tracts, OPCs, and remain expressed in mature myelinating oligodendrocytes. Evidence suggests that S1P5 receptors are involved in regulating myelination since binding of S1P to S1P5 receptors in mature oligodendrocytes promotes their survival whereas binding of S1P to S1P5 receptors on OPCs inhibits their motility. Since remyelination can occur subsequent to demyelination and can contribute to functional recovery, S1P5 modulators (e.g., S1P5 agonists or S1P5 antagonists) are expected to be useful in treating or preventing demyelination disorders.

For example, MS can begin with a relapsing-remitting pattern of neurologic involvement, which then can progress to a chronic phase with increasing neurological damage. MS can be associated with the destruction of myelin, oligodendrocytes or axons localized to chronic lesions. However, the demyelination observed in MS may not always permanent and remyelination has been documented in early stages of the disease. Remyelination of neurons can require oligodendrocytes. Thus, S1P5 agonist, which would be expected to increase the survival of mature oligodendrocytes or S1P5 antagonist which would be expected to increase the motility of OPC, depending on the stage of the disease would be expected to be useful in treating or preventing MS and other demyelination disorders.

Therefore, the compounds of the invention are expected to be useful in treating or preventing demyelination disorder which include, but are not limited to, demyelination due to immune dysfunction as in multiple sclerosis, encephalomyelitis, Guillain-Barre Syndrome, chronic inflammatory demyelinating polyneuropathy (CIDP), transverse myelitis, and optic neuritis; demyelination due to injury such as spinal cord injury, traumatic brain injury, stroke, acute ischemic optic neuropathy, or other ischemia, cerebral palsy, neuropathy (e.g. neuropathy due to diabetes, chronic renal failure, hypothyroidism, liver failure, or compression of the nerve (e.g. in Bell's palsy)), post radiation injury, and central pontine myelolysis (CPM); demyelination due to inherited conditions such as Charcot-Marie-Tooth disease (CMT), Sjogren-Larsson syndrome, Refsum disease, Krabbe disease, Canavan disease, Alexander disease, Friedreich's ataxia, Pelizaeus-Merzbacher disease, Bassen-Kornzweig syndrome, metachromatic leukodystrophy (MLD), adrenoleukodystrophy, and nerve damage due to pernicious anemia; demyelination due to a viral infection such as progressive multifocal leukoencephalopathy (PML), Lyme disease, or tabes dorsalis due to untreated syphilis; demyelination due to toxic exposure such as chronic alcoholism (which is a possible cause of Marchiafava-Bignami disease), chemotherapy, or exposure to chemicals such as organophosphates; demyelination due to a dietary deficiency such as vitamin B12 deficiency, vitamin E deficiency and copper deficiency; or demyelination which has unknown causes or multiple causes such as trigeminal neuralgia, Marchiafava-Bignami disease and Bell's palsy. Among these diseases, MS may the most widespread, affecting approximately 2.5 million people worldwide.

Various disease-modifying treatments may be available for MS, including the use of corticosteroids and immunomodulating agents such as interferon beta or Tysabri®. In addition, because of the central role of oligodendrocytes and myelination in MS, there have been efforts to develop therapies to increase oligodendrocyte numbers or survival to enhance myelination. See, e.g., Cohen et al., U.S. Pat. No. 5,574,009; Chang et al., *N. Engl. J. Med.* 346: 165-73 (2002), each of which is incorporated by reference in its entirety. However, there remains an urgent need to devise additional therapies for MS and other demyelination disorders.

A compound of formula (I), or a pharmaceutically acceptable salt thereof, can promote myelination or remyelination. A method can include administering a compound of formula (I), or a pharmaceutically acceptable salt thereof, to cells. A method of promoting oligodendrocyte survival can include administering a compound of formula (I), or a pharmaceutically acceptable salt thereof, to cells. A method of treating multiple sclerosis can include administering a compound of formula (I), or a pharmaceutically acceptable salt thereof, to a subject.

The S1P receptor modulating agents (e.g., S1P5 modulating agents) of formula (I) can be used to prevent, treat, or reduce symptoms of various forms of MS including relapsing-remitting, secondary-progressive, primary-progressive, and progressive-relapsing forms. In addition, SIP receptor modulating agents (e.g., S1P5 modulating agents) of formula (I) can be used alone or in conjunction with other agents to treat or prevent MS. In a preferred embodiment, the compounds of formula (I) can be used to treat or prevent MS in combination with an immunomodulating therapy such as corticosteroids, beta interferon-1a (such as Avonex® or Rebif®), beta interferon-1b (Betaseron®), natalizumab (Tysabri®), glatiramer, and mitoxantrone.

Moreover, altered sphingolipid metabolism has been shown to play a role in cognitive and neurodegenerative diseases. It has been observed that the brains of patients with Alzheimer's disease, ALS and AIDS dementia have been shown to have elevated ceramide and sphingosine and low S1P compared to cognitively normal individuals indicating that such a profile is characteristic of neurodegenerative disease. (Mielke, M. M. and Lyketsos, C. G., *Neuromolecular Med.* (2010), 12(4):331-340). Since ceramide has been shown to be pro-apoptotic, whereas the binding of S1P to S1P receptors has been linked to resistance to apoptosis, increased cell migration and division, and oligodendrocyte differentiation and survival, compounds which could either shift the balance of ceramide/S1P in favor of S1P-mediated survival and away from ceramide-mediated cell death are expected to be of benefit in treating neurodegenerative and cognitive disorders.

Therefore, the compounds of the invention, and pharmaceutically acceptable salts thereof, are expected to be useful in treating or preventing neurodegenerative and cognitive diseases. In one embodiment, the neurodegenerative or cognitive disease is selected from the group consisting of Alzheimer's disease, Parkinson's disease, dementia with Lewy bodies, multiple system atrophy, Huntington's disease, spinocerebellar ataxias (e.g., SCA1, SCA2, SCA3, SCA6, SCAT, and SCA17), spinobulbar muscular atrophy (SBMA) or Kennedy disease, dentatorubropallidoluysian atrophy (DRPLA), ALS, and AIDS dementia. In another embodiment, the neurodegenerative or cognitive disease is selected from the group consisting of Alzheimer's disease, ALS and AIDS dementia. In another embodiment, the neurodegenerative disease is a disease that affects cognition (e.g., Alzheimer's disease, demential with Lewy bodies, frontotemporal dementia, corticobasal ganglionic degeneration, progressive supranuclear palsy, Creutzfeldt-Jakob disease, Gerstmann-Sträussler-Scheinker syndrome, and fatal familial insomnia). In another embodiment, the neurodegenerative disease is a disease that effects movement (e.g., Parkinson's disease, demential with Lewy bodies, frontotemporal dementia, corticobasal ganglionic degeneration, progressive supranuclear palsy, Huntington's disease, and multiple system atrophy). In another embodiment, the neurodegenerative disease is a disease that effects strength (e.g., ALS, frontotemporal dementia, and hereditary spastic paraplegia).

Autoimmune Disorders

Natural killer (NK) cells are lymphocytes of the innate immune system that control infections by viruses and intracellular bacteria and parasites. NK cells are developed in the bone marrow then released into circulation in the blood and are found in large numbers in the spleen, liver and lymph nodes. NK cells selectively express S1P5 receptors and recently it has been found that mice deficient in S1P5 receptors have altered distribution of NK cells, showing reduced levels in the blood and spleen and increased levels in the bone marrow and lymph nodes (see Jenne, et al., JEM (2009), 206:2469-2481). This observation lead to the hypothesis that S1P5 receptors are involved in mediating egress of NK cells from the lymph node and bone marrow into the circulation. Thus, modulators of S1P5 receptors would be expected to alter the activity of NK cells.

In patients with multiple sclerosis enrichment of NK cells has been shown to ameliorate the disease, whereas selective blockade of NK cell homing to the CNS has been shown to result in disease exacerbation (see Hao, et al., *J. of Exp. Medicine* (2010), 207(9):1907-1921). In clinical trials, treatment of MS patients with Daclizumab therapy resulted in a gradual expansion of a subset of NK cells, $CD56^{bright}$ NK cells, in the CNS which strongly correlated with decreased brain inflammatory activity. The expansion of $CD56^{bright}$ NK cells limited the survival of activated T cells, and NK cells isolated from patients treated with Daclizumab were directly cytotoxic to autologous activated T cells. This cytotoxicity of NK cells to activated T cells suggests that NK cells may be involved in terminating an adaptive immune response and may play a critical role in controlling the magnitude of CNS inflammation in MS (see Bielekova, et al., *PNAS* (2006), 103(15):5941-5946).

In contrast, NK cells are thought to play a role in promoting or exacerbating the pathology of a number of autoimmune disorders. For example, it has been demonstrated that a subset of NK cells, $CD56^{bright}$ NK cells, is greatly expanded in synovial fluid of patients with inflammatory arthritis (rheumatoid arthritis, psoriatic arthritis, ankylosing spondylitis, gout and juvenile idiopathic arthritis), and that NK cells at inflammatory sites produce more IFN-γ than peripheral NK cells. NK cells can be divided into $CD56^{dim}$ subset and $CD56^{bright}$ subset. $CD56^{bright}$ NK cells account for about 10% of circulating NK cells but are the dominant subset of NK cells in the lymph nodes. $CD56^{bright}$ NK cells have a greater ability to produce proinflammatory cytokines on exposure to low concentrations of monokines and are likely to be important in maintaining the chronic inflammation seen in inflammatory arthritis (see Dalbeth, et al., *J. of Immunology* (2004), 173:6418-6426).

Type 1 diabetes is an autoimmune disease in which insulin-producing beta cells in pancreatic islets are destroyed by autoreactive T cells. However, NK cells are thought to play a critical role in the disease development. Research indicates that depletion of NK cells inhibits the development of diabetes in non-obese diabetic (NOD) mice (see Alba, et al., Clinical and Exp. Immunology (2008), 151:467-475). Moreover, natural cyctotoxic receptor, NKp46, on the surface of NK cells has been shown to recognize and bind to human ligands on pancreatic beta cells leading to degranulation of the NK cells. In NOD mice that were injected with streptozotocin to induce onset of diabetes, injection of soluble NKp46 receptor provided almost complete protection from the onset of diabetes. Thus, NK cells with functional NKp46 receptors are thought to be essential for the development of type 1 diabetes (see Gur, et al., Nature Immunology (2010), 11(2):121-129).

Thus, S1P5 modulators that modulate the expansion or honing of NK cells, or a subset of NK cells such as $CD56^{bright}$ NK cells, may be useful in treating autoimmune disorders such as MS, inflammatory arthritis, and diabetes.

Pain Mediation

Pain experienced by mammals can be divided into two main categories: acute pain (or nociceptive) and chronic pain which can be subdivided into chronic inflammatory pain and chronic neuropathic pain. Acute pain is a response to stimulus that causes tissue injury and is a signal to move away from the stimulus to minimize tissue damage. Chronic pain, on the other hand, serves no biological function and develops as a result of inflammation caused by tissue damage (inflammatory pain) or by damage to the nervous system such as demyelination (neuropathic pain). Chronic pain is generally characterized by stimulus-independent, persistent pain or by abnormal pain perception triggered by innocuous stimuli.

FTY720 which is an S1P1, S1P3, S1P4 and S1P5 agonist has been found to decrease response to nociceptive and neuropathic pain in mammals. In a spinal nerve injury modes for neuropathic pain FTY720 decreased nociceptive behavior similar to gabapentin, a commonly used drug for the treatment of neuropathic pain. However, SEW2871 a selected S1P1 agonist did not influence pain behavior (Coste, et el., J. of Cell. Mol. Med. (2008), 12:995-1004). These results coupled with the high expression of S1P5 in the central nervous system (CNS) suggest that S1P5 receptors mediate the effects of FTY720 on pain. Thus, the compounds of the invention, or a pharmaceutically acceptable salt thereof, which modulate S1P5 receptor activity and promote remyelination, are expected to be useful in treating or preventing pain such as nociceptive or chronic pain (inflammatory pain and neuropathic pain) in mammals.

In cases where a compound of formula (I) can be sufficiently basic or acidic to form stable nontoxic acid or base salts, preparation and administration of the compounds as pharmaceutically acceptable salts may be appropriate. Examples of pharmaceutically acceptable salts can be organic acid addition salts formed with acids which form a physiological acceptable anion, for example, tosylate, methanesulfonate, acetate, citrate, malonate, tartarate, succinate, benzoate, ascorbate, α-ketoglutarate, or α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, can include but are not limited to, sodium, potassium, lithium, ammonium, calcium or magnesium salts. Salts derived from organic bases can include, but are not limited to, salts of primary, secondary or tertiary amines, such as alkyl amines, dialkyl amines, trialkyl amines, substituted alkyl amines, di(substituted alkyl)amines, tri(substituted alkyl)amines, alkenyl amines, dialkenyl amines, trialkenyl amines, substituted alkenyl amines, di(substituted alkenyl)amines, tri(substituted alkenyl)amines, cycloalkyl amines, di(cycloalkyl)amines, tri(cycloalkyl) amines, substituted cycloalkyl amines, disubstituted cycloalkyl amine, trisubstituted cycloalkyl amines, cycloalkenyl amines, di(cycloalkenyl)amines, tri(cycloalkyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, or mixed di- and tri-amines where at least two of the substituents on the amine can be different and can be alkyl, substituted alkyl, alkenyl, substituted alkenyl, cycloalkyl, substituted cycloalkyl, cycloalkenyl, substituted cycloalkenyl, aryl, heteroaryl, or heterocyclic and the like. Also included can be amines where the two or three substituents, together with the amino nitrogen, form a heterocyclic or heteroaryl group. Nonlimiting examples of amines can include, isopropylamine, trimethyl amine, diethyl amine, tri(iso-propyl)amine, tri(n-propyl)amine, ethanolamine, 2-dimethyl-aminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, or N-ethylpiperidine, and the like. Other carboxylic acid derivatives can be useful, for example, carboxylic acid amides, including carboxamides, lower alkyl carboxamides, or dialkyl carboxamides, and the like.

Pharmaceutical compositions can include a compound of formula (I), or a pharmaceutically acceptable salt thereof. More particularly, such compounds can be formulated as pharmaceutical compositions using standard pharmaceutically acceptable carriers, fillers, solubilizing agents and stabilizers known to those skilled in the art. For example, a pharmaceutical composition including a compound of formula (I), or a salt, analog, derivative, or modification thereof, as described herein, is used to administer the appropriate compound to a subject.

The compounds of formula (I), or a pharmaceutically acceptable salt thereof, are useful for treating a disease or disorder associated with S1P receptor activity. In one embodiment, a therapeutically effective amount of a compound of formula (I), or a pharmaceutically acceptable salt thereof, is administered to a subject in need thereof. In another embodiment, a pharmaceutical composition comprising a therapeutically effective amount of a compound of formula (I), or a pharmaceutically acceptable salt thereof, and a pharmaceutically-acceptable carrier is administered to a subject in need thereof.

The compounds of formula (I) can be used in combination with at least one further active ingredient, such as a medicament used in the treatment of multiple sclerosis such as Tysabri®, dimethyl fumarate, an interferon (such as pegylated or non-pegylated interferons, preferably interferon β-1a or pegylated interferon β-1a), glatiramer acetate, a compound improving vascular function, an immunomodulating agent (such as Fingolimod, cyclosporins, rapamycins or ascomycins, or their immunosuppressive analogs, e.g. cyclosporine A, cyclosporine G, FK-506, ABT-281, ASM981, rapamycin, 40-O-(2-hydroxyl)ethyl-rapamycin etc.); corticosteroids; cyclophosphamide; azathioprine; mitoxanthrone, methotrexate; leflunomide; mizoribine; mycophenolic add; mycophenolate mofetil; 15-deoxyspergualine; diflucortolone valerate; difluprednate; Alclometasone dipropionate; amcinonide; amsacrine; asparaginase; azathioprine; basiliximab; beclometasone dipropionate; betamethasone; betamethasone dipropionate; betamethasone phosphate sodique; betamethasone valerate; budesonide; captopril; chlormethine chlorhydrate; clobetasol propionate; cortisone acetate; cortivazol; cyclophosphamide; cytarabine; daclizumab; dactinomycine; desonide; desoximetasone; dexamethasone; dexamethasone acetate; dexamethasone isonicotinate; dexamethasone metasulfobenzoate sodique; dexamethasonephosphate; dexamethasone tebutate; dichlorisone acetate; doxorubicinee chlorhydrate; epirubicine chlorhydrate; fluclorolone acetonide; fludrocortisone acetate; fludroxycortide; flumetasone pivalate; flunisolide; fluocinolone acetonide; fluocinonide; fluocortolone; fluocortolone hexanoate; fluocortolone pivalate; fluorometholone; fluprednidene acetate; fluticasone propionate; gemcitabine chlorhydrate; halcinonide; hydrocortisone; hydrocortisone acetate; hydrocortisone butyrate; hydrocortisone hemisuccinate; melphalan; meprednisone; mercaptopurine; methylprednisolone; methylprednisolone acetate; methylprednisolone hemisuccinate; misoprostol; muromonab-cd3; mycophenolate mofetil; paramethansone acetate; prednazoline, prednisolone; prednisolone acetate; prednisolone caproate; prednisolone metasulfobenzoate sodique; prednisolone phosphate sodique; prednisone; prednylidene; rifampicine; rifampicine sodique; tacrolimus; teriflunomide; thalidomide; thiotepa; tixocortol pivalate; triamcinolone; triamcinolone acetonide hemisuccinate; triamcinolone benetonide; triamcinolone diacetate; triamcinolone hexacetonide; immunosuppressive monoclonal antibodies, e.g., monoclonal antibodies to leukocyte receptors, e.g., MHC, CD2, CD3, CD4, CD7, CD20 (e.g., rituximab and ocrelizumab), CD25, CD28, B7, CD40, CD45, CD56 (e.g., daclizumab), or CD58 or their ligands; or other immunomodulating agenty compounds, e.g. CTLA41g, or other adhesion molecule inhibitors, e.g. mAbs or low molecular weight inhibitors including Selectin antagonists and VLA-4 antagonists (such as Tysabri®); remyelinating agents such as BIIB033. Compounds of formula (I) can also be used in combination with agents which treat the symptoms of multiple sclerosis such as fampridine.

The dose of a compound of formula (I), or a pharmaceutically acceptable salt thereof, administered to a subject can be less than 10 μg, less than 25 μg, less than 50 μg, less than 75 μg, less than 0.10 mg, less than 0.25 mg, less than 0.5 mg, less than 1 mg, less than 2.5 mg, less than 5 mg, less than 10 mg, less than 15 mg, less than 20 mg, less than 50 mg, less than 75 mg, less than 100 mg, or less than 500 mg.

Administering can include administering by topical, enteral, parenteral, transdermal, transmucosal, inhalational, intracisternal, epidural, intravaginal, intravenous, intramuscular, subcutaneous, intradermal or intravitreal administration.

The duration of administering can be less than 30 seconds, less than 1 minute, about 1 minute, between 1 minute and 5 minutes, between 5 minutes and 10 minutes, between 10 minutes and 20 minutes, between 20 minutes and 30 minutes, between 30 minutes and 1 hour, between 1 hour and 3 hours, between 3 hours and 6 hours, between 6 hours and 12 hours, between 12 hours and 24 hours or for more than 24 hours.

Administering the inhibitor or compound can include multiple administrations. The duration between administrations can be less than 30 seconds, less than 1 minute, about 1 minute, between 1 minute and 5 minutes, between 5 minutes and 10 minutes, between 10 minutes and 20 minutes, between 20 minutes and 30 minutes, between 30 minutes and 1 hour, between 1 hour and 3 hours, between 3 hours and 6 hours, between 6 hours and 12 hours, between 12 hours and 24 hours or for more than 24 hours.

The duration between successive administrations can be less than 30 seconds, less than 1 minute, about 1 minute, between 1 minute and 5 minutes, between 5 minutes and 10 minutes, between 10 minutes and 20 minutes, between 20 minutes and 30 minutes, between 30 minutes and 1 hour, between 1 hour and 3 hours, between 3 hours and 6 hours, between 6 hours and 12 hours, between 12 hours and 24 hours, between 24 hours and 48 hours, between 48 hours and 72 hours, between 72 hours and 1 week or between 1 week and 2 weeks.

Administering an inhibitor or compound to cells can include cells of an in vitro or in vivo system or model. The cells can be part of a cell line. The cell line can be a primary or secondary cell line. The cell line can be an immortal cell line. The cells can be ruptured and be in the form of a cell lysate. The cells can be part of a living organism, i.e., a subject, for example, a mammal. A mammal can include a rat, a mouse, a gerbil, a hamster, a rabbit or a human. The human can be a subject or a patient.

A method can further include monitoring a property of a sample or a subject. A sample can be removed from a subject. For instance, a sample can include a sample of cells or a tissue from a subject. A sample can include blood, plasma, or neuronal tissue including neurons or glial cells. A sample can also remain in the subject. For example, a sample can be a tissue or cells that are observed within the patient.

A method can further include providing untreated control cells, sample or subject and measuring a property of a sample of the untreated control cells, sample or subject.

A property can include the presence or absence of a molecule, the concentration of a molecule, for example myelin basic protein, myelin associated glycoprotein or myelin oligodendrocyte glycoprotein. In some embodiments, determining the presence of a molecule can include determining the concentration of the molecule, determining the purity of the molecule or determining the quantity of the molecule.

A property can be the conductivity of a tissue or cell. A property can be an emission, for example, electromagnetic radiation.

Monitoring a property can include observing the property of the sample or subject alone. Monitoring a property can include monitoring the property before the sample or subject has been administered a compound of formula (I). Monitoring a property can include monitoring the property after the sample or subject has been administered a compound. Monitoring a property can include monitoring a property after the sample or subject has been administered a known concentration of a compound.

Monitoring a property of a sample or subject can include observing the property through a microscope. Monitoring a property of the composition can include measuring the property using a microscope. Monitoring a property of the composition can include monitoring the property using still photography or movies. The photography or movies can be on film media or digital form. Monitoring a property can include taking a scan, for example, an MRI or CT scan.

Promoting myelination, remyelination or oligodendrocyte progenitor cell differentiation can prevent or can treat a pathological condition or symptom in a mammal. A number of diseases or disorders involve demyelination of the central or peripheral nervous system which can occur for a number of reasons such as immune dysfunction as in multiple sclerosis, encephalomyelitis, Guillain-Barre Syndrome, chronic inflammatory demyelinating polyneuropathy (CIDP), transverse myelitis, and optic neuritis; demyelination due to injury such as spinal cord injury, traumatic brain injury, stroke, acute ischemic optic neuropathy, or other ischemia, cerebral palsy, neuropathy (e.g. neuropathy due to diabetes, chronic renal failure, hypothyroidism, liver failure, or compression of the nerve), post radiation injury, and central pontine myelolysis (CPM); inherited conditions such as Charcot-Marie-Tooth disease (CMT), Sjogren-Larsson syndrome, Refsum disease, Krabbe disease, Canavan disease, Alexander disease, Friedreich's ataxia, Pelizaeus-Merzbacher disease, Bassen-Kornzweig syndrome, metachromatic leukodystrophy (MLD), adrenoleukodystrophy, and nerve damage due to pernicious anemia; viral infection such as progressive multifocal leukoencephalopathy (PML), Lyme disease, or tabes dorsalis due to untreated syphilis; toxic exposure due to chronic alcoholism (which is a possible cause of Marchiafava-Bignami disease), chemotherapy, or exposure to chemicals such as organophosphates; or dietary deficiencies such as vitamin B12 deficiency, vitamin E deficiency, and copper deficiency. Some demyelination disorders can have unknown or multiple causes such as trigeminal neuralgia, Marchiafava-Bignami disease and Bell's palsy. In addition, demyelination can contribute to neuropathic pain. Compounds of formula (I) are expected to be useful in treating demyelination disorders.

A compound of formula (I), or a pharmaceutically acceptable salt thereof, formulated as a pharmaceutical composition and administered to a mammalian host, such as a human patient in a variety of forms adapted to the chosen route of administration, e.g., orally or parenterally, as eyedrops, by intravenous, intramuscular, topical or subcutaneous routes.

Thus, compound of formula (I), or a pharmaceutically acceptable salt thereof, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, or wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions can be such that an effective dosage level will be obtained.

The tablets, troches, pills, capsules, and the like can include the following: binders such as gum tragacanth, acacia, corn starch or gelatin; excipients such as dicalcium phosphate; a disintegrating agent such as corn starch, potato starch, alginic acid and the like; a lubricant such as magnesium stearate; or a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl or propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, or nontoxic glyceryl esters, and mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, or thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate or gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation can be vacuum drying and the freeze drying techniques, which can yield a powder of the active ingredient plus any additional desired ingredient present in the previously sterile-filtered solutions.

For topical administration, a compound of formula (I) may be applied in pure form, e.g., when they are liquids. However, it can be generally be desirable to administer them to the skin as compositions or formulations, in combination with a dermatologically acceptable carrier, which may be a solid or a liquid.

Exemplary solid carriers can include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts or esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula (I) to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), each of which is incorporated by reference in its entirety.

Useful dosages of the compounds of formula (I) can be determined by comparing their in vitro activity, and in vivo activity in animal models. Methods for the extrapolation of effective dosages in mice, and other animals, to humans are known to the art; for example, see U.S. Pat. No. 4,938,949, which is incorporated by reference in its entirety.

Generally, the concentration of the compound(s) of formula (I) in a liquid composition, such as a lotion, can be from about 0.1 to about 25 weight percent, preferably from about 0.5-10 weight percent. The concentration in a semi-solid or solid composition such as a gel or a powder can be about 0.1-5 wt-%, preferably about 0.5-2.5 weight percent based on the total weight of the composition.

The amount of the compound, or an active salt or derivative thereof, required for use in treatment can vary not only with the particular salt selected but also with the route of administration, the nature of the condition being treated and the age and condition of the patient and can be ultimately at the discretion of the attendant physician or clinician. In general, however, a dose can be in the range of from about 0.1 to about 10 mg/kg of body weight per day.

The compound can be conveniently administered in unit dosage form; for example, containing 0.01 to 10 mg, or 0.05 to 1 mg, of active ingredient per unit dosage form. In some embodiments, a dose of 5 mg/kg or less can be suitable.

The active ingredient can be administered so as to achieve a desired peak plasma concentration of the active compound. The desired peak plasma concentration can be from about 0.5 µM to about 75 µM, preferably, about 1 µM to 50 µM, or about 2 µM to about 30 µM. This may be achieved, for example, by the intravenous injection of a 0.05 to 5% solution of the active ingredient, optionally in saline, or orally administered as a bolus containing between about 1 mg to about 100 mg of the active ingredient.

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations; such as multiple inhalations from an insufflator or by application of a plurality of drops into the eye.

The disclosed method can include a kit comprising a compound of formula (I) and instructional material which can describe administering the compound or a composition comprising the compound to a cell or a subject. This should be construed to include other embodiments of kits that are known to those skilled in the art, such as a kit comprising a (preferably sterile) solvent for dissolving or suspending the compound or composition prior to administering the compound or composition to a cell or a subject. Preferably, the subject can be a human.

In accordance with the disclosed methods, as described above or as discussed in the Examples below, there can be employed conventional chemical, cellular, histochemical, biochemical, molecular biology, microbiology, and in vivo techniques which are known to those of skill in the art. Such techniques are explained fully in the literature.

EXAMPLES

Example 1: 2-(((2-(((trans)-4-(tert-butyl)cyclohexyl)oxy)-4-methylnaphthalen-1-yl)methyl)amino)acetic acid Step 1: 4-methoxypent-3-en-2-one

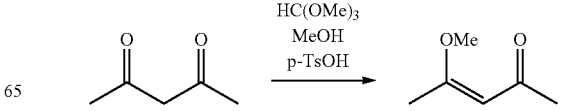

A solution of 2,4-pentanedione (100 g, 1 mol), trimethyl orthoformate (106 g, 1 mol), p-TsOH.H₂O (2.16 g, 11.4 mmol) in MeOH (248 mL) was heated at 55° C. for 5 hrs. The mixture was cooled to room temperature and concentrated. The residue was diluted with CCl₄ (100 mL) and the mixture was concentrated again to give the crude product as a dark-brown oil (~100 g). This residue was subjected to vacuum distillation to give colorless oil (58.0 g, yield: 50%). by 32-33° C./3 torr).

Step 2: 3-methoxy-1-methylnaphthalene

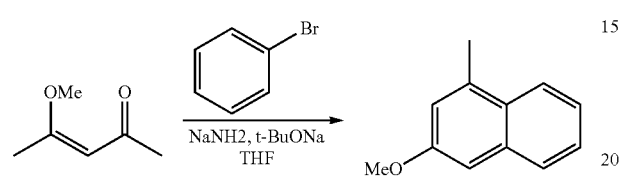

A solution of t-BuOH (44.5 g, 600 mmol) in dry THF (240 mL) was added dropwise to a suspension of NaNH₂ (84.4 g, 2.2 mmol) in dry THF (480 mL) under nitrogen. The resulting mixture was heated for 2 h at 40-45° C. After the mixture was cooled, a solution of 4-methoxypent-3-en-2-one (68.5 g, 600 mmol) in dry THF (480 mL) was added dropwise at 30-40° C. The resulting mixture was stirred at 45° C. for 2 h. A solution of bromobenzene (47.1 g, 300 mmol) in dry THF (240 mL) was added and the mixture was stirred at 55° C. for 6 h. The mixture was allowed to cool to room temperature overnight. The mixture was poured into ice, acidified with an aqueous 3 M HCl solution to pH 4-5 and extracted with EtOAc. The combined organic extracts were concentrated under reduced pressure, and the residue was diluted with acetone (480 mL) and stirred with conc. HCl solution (24 mL) for 10 min. The mixture was diluted with EtOAc (200 mL) and washed with saturated brine (200 mL). The aqueous layer was extracted with EtOAc, and the combined organic layers were dried over sodium sulfate, filtered, and concentrated. The residue was subjected to flash chromatography (700 g silica gel with dry-loading, eluting by 2% EtOAc in heptanes to give orange oil (19 g, yield: 37%).

Step 3: 4-Methylnaphthalen-2-ol

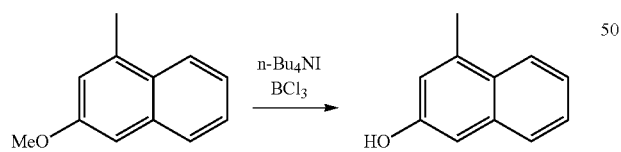

A solution of 4-methylnaphthalen-2-ol compound (22 g, 128 mmol) and n-Bu₄I (52 g, 141 mmol) in dry dichloromethane (650 mL) was added 1.0 M solution of BCl₃ in dichloromethane (192 mL, 192 mmol) at −78° C. under nitrogen. After 5 min, the solution was allowed to warm to 0° C. and stirred for 1 h. The reaction was quenched with cold water (200 mL) and extracted with dichloromethane. The combined extracts were washed with saturated brine, dried over sodium sulfate, filtered, and concentrated. The residue was subjected to flash chromatography, eluting with a gradient of 10% to 50% EtOAc in heptanes to give brown solid product (16 g, yield: 79%).

Step 4: 3-(4-tert-butyl-cyclohexyloxy)-1-methyl-naphthalene

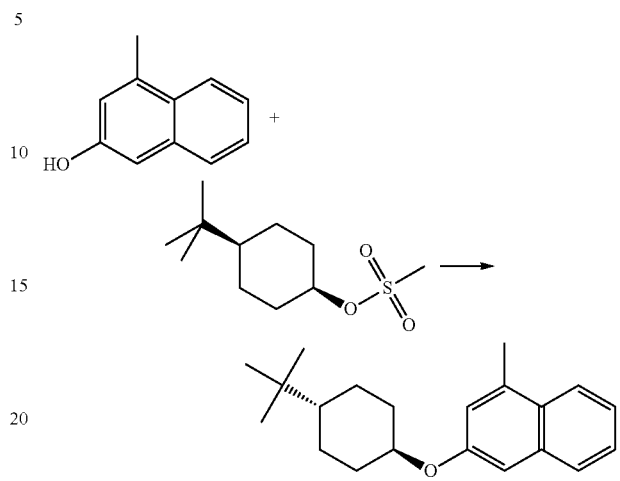

A mixture of 4-methyl-naphthalen-2-ol (0.60 g, 3.8 mmol), methanesulfonic acid 4-tert-butyl-cyclohexyl ester (1.9 g, 7.6 mmol) and cesium carbonate (3.7 g, 11 mmol) in t-BuOH (10 mL) and 2-butanone (7 mL) was heated at 80° C. overnight. After cooled to room temperature, the mixture was treated with water and ether. The organic phase was dried over MgSO₄, filtered and concentrated. The crude was treated with methanol to give solid product (0.55 g, yield: 48%). ESI-MS: 297.20 (M+H)⁺.

Step 5: 2-(((trans)-4-(tert-butyl)cyclohexyl)oxy)-4-methyl-1-naphthaldehyde

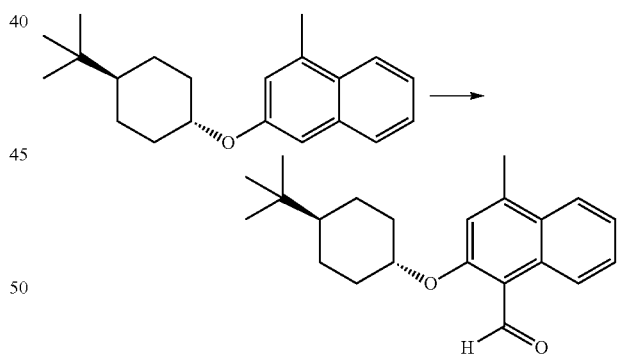

To a mixture of 3-(4-tert-butyl-cyclohexyloxy)-1-methyl-naphthalene (450 mg, 1.5 mmol) in 1,2-dichloroethane (9 mL) was added tin tetrachloride (236 uL, 2 mmol) at 0° C. After stirred at 0° C. for 1 hr, dichloromethyl methyl ether (183 uL, 2 mmol) was added. The solution was stirred at 0° C. for 1 hr and then warmed to room temperature. The mixture was added ice water and stirred for 1 hr, then the dark solution was diluted with dichloromethane and washed with water. The organic phase was washed with sodium bicarbonate aqueous, and dried over MgSO₄. The drying agent was filtered off and the solvent was concentrated to dryness to give dark solid product (0.48 g, yield: 97%). ESI-MS: 325.20 (M+H)⁺.

Step 6: methyl 2-(((2-(((trans)-4-(tert-butyl)cyclohexyl)oxy)-4-methylnaphthalen-1-yl)methyl)amino)acetate

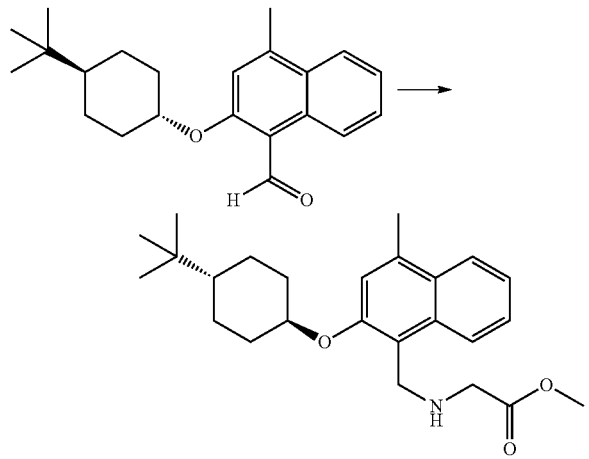

A solution of 2-(((trans)-4-(tert-butyl)cyclohexyl)oxy)-4-methyl-1-naphthaldehyde (50 mg, 0.15 mmol), glycine methyl ester, hydrochloride (27 mg, 0.22 mmol) and N,N-diisopropylethylamine (DIEA) (34 uL) in 1,2-dichloroethane (2 mL) was stirred for 1 hour at room temperature. Then sodium triacetoxyborohydride (52 mg, 0.25 mmol) was added and stirred for 3 hrs. The reaction was diluted with methylene chloride and washed with saturated sodium bicarbonate aqueous, dried over MgSO$_4$, filtered, and concentrated. The crude was purified via silica gel column chromatography eluted 0-5% MeOH in methylene chloride to give the light brown solid (53 mg, yield: 86%). ESI-MS: 420.30 (M+23)$^+$.

Step 7: 2-(((2-(((trans)-4-(tert-butyl)cyclohexyl)oxy)-4-methylnaphthalen-1-yl)methyl)amino)acetic acid

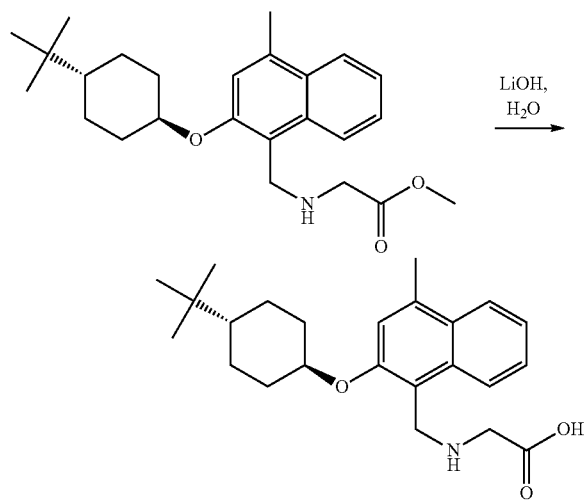

A solution of methyl 2-(((2-(((trans)-4-(tert-butyl)cyclohexyl)oxy)-4-methylnaphthalen-1-yl)methyl)amino)acetate (40 mg, 0.1 mmol) and lithium hydroxide (16 mg, 0.67 mmol) in THF (1.4 mL) and water (0.5) was stirred at 22° C. overnight. After the solvent was concentrated, the residue was treated with water. The resulting solid was filtered and washed with water and purified via HPLC to give white precipitate as TFA salt (24 mg, yield: 48%). ESI-MS: 406.30 (M+23)$^+$; $^1$H NMR (400 MHz, MeOD) δ=8.075 (d, 1H), 8.065 (d, 1H), 7.62 (t, 1H), 7.48 (dd, 1H), 7.38 (s, 1H), 4.78 (s, 2H), 4.52 (m, 1H), 3.86 (s, 1H), 2.75 (s, 3H), 2.66 (s, 1H), 2.27 (d, 2H), 1.926 (d, 2H), 1.557 (m, 2H), 1.256 (m, 2H), 1.152 (m, 1H), 0.92 (s, 9H).

Example 2: 4-(((2-(((trans)-4-(tert-butyl)cyclohexyl)oxy)-4-methylnaphthalen-1-yl)methyl)amino)butanoic acid

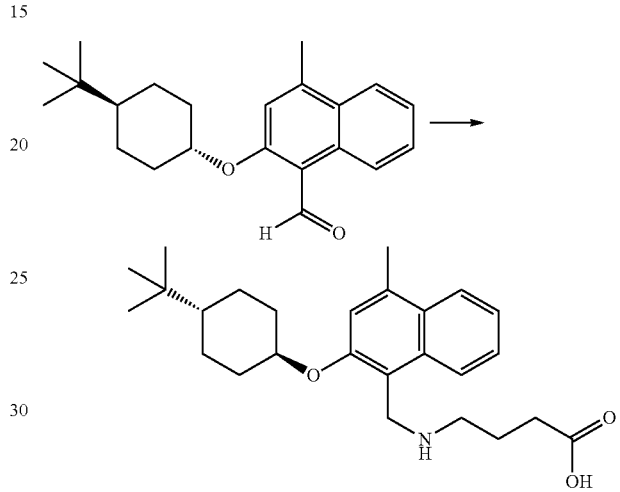

A solution of 2-(((trans)-4-(tert-butyl)cyclohexyl)oxy)-4-methyl-1-naphthaldehyde (50 mg, 0.15 mmol) and 4-aminobutanoic acid (20 mg, 0.19 mmol) in ethanol (0.5 mL) was heated to reflux for 2 hrs. The yellow solution was cooled to room temperature and sodium cyanoborohydride (52 mg) was added. The mixture was heated at 50° C. overnight. The crude product was purified via HPLC to give white solid as TFA salt (9 mg, yield: 11%). ESI-MS: 412.30 (M+H)$^+$; $^1$H NMR (400 MHz, MeOD) δ 8.06 (d, 1H), 8.03 (d, 1H), 7.58-7.65 (m, 1H), 7.48 (t, J=7.15 Hz, 1H), 7.38 (s, 1H), 4.68 (s, 2H), 4.53 (m, 1H), 3.20 (t, 2H), 2.75 (s, 3H), 2.48 (t, J=6.90 Hz, 2H), 2.29 (d, J=10.54 Hz, 2H), 2.04 (quin, J=7.34 Hz, 2H), 1.94 (d, 2H), 1.54 (m, 2H), 1.28 (m, 2H), 1.16 (m, 1H), 0.93 (s, 9H).

Example 3: 1-((2-(((trans)-4-(tert-butyl)cyclohexyl)oxy)-4-methylnaphthalen-1-yl)methyl)azetidine-3-carboxylic acid

Step 1: methyl 1-((2-(((trans)-4-(tert-butyl)cyclohexyl)oxy)-4-methylnaphthalen-1-yl)methyl)azetidine-3-carboxylate

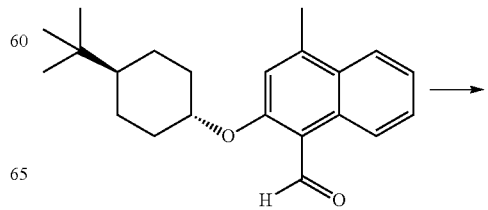

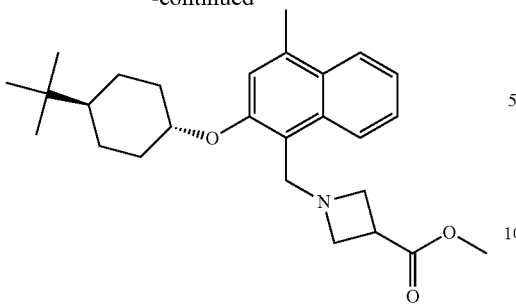

Synthesis was performed as described for methyl 2-(((2-(((trans)-4-(tert-butyl)cyclohexyl)oxy)-4-methylnaphthalen-1-yl)methyl)amino)acetate (40 mg, yield: 51%). ESI-MS: 424.30 (M+H)$^+$.

Step 2: 1-((2-(((trans)-4-(tert-butyl)cyclohexyl)oxy)-4-methylnaphthalen-1-yl)methyl)azetidine-3-carboxylic acid

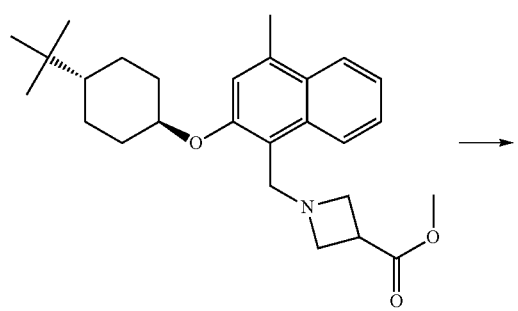

Synthesis was performed as described for 2-(((2-(((trans)-4-(tert-butyl)cyclohexyl)oxy)-4-methylnaphthalen-1-yl)methyl)amino)acetic acid. The product was treated with 1N HCl aqueous gave light yellow solid as HCl salt (30 mg, yield: 86%). ESI-MS: 410.30 (M+H)$^+$. $^1$H NMR (400 MHz, DMSO) δ 8.10 (d, 1H), 7.97 (d, 1H), 7.55 (t, 1H), 7.47-7.41 (m, 2H), 4.60-4.45 (m, 2H), 3.97 (s, 3H), 3.50-3.33 (m, 2H), 2.68 (s, 3H), 2.16 (d, 2H), 1.81 (d, 2H), 1.47 (quin, 2H), 1.20 (quin, 2H), 1.09 (m, 2H), 0.88 (s, 9H).

Example 4: 3-(((2-(((trans)-4-(tert-butyl)cyclohexyl)oxy)-4-methylnaphthalen-1-yl)methyl)amino)propanoic acid Step 1: ethyl 3-(((2-(((trans)-4-(tert-butyl)cyclohexyl)oxy)-4-methylnaphthalen-1-yl)methyl)amino)propanoate

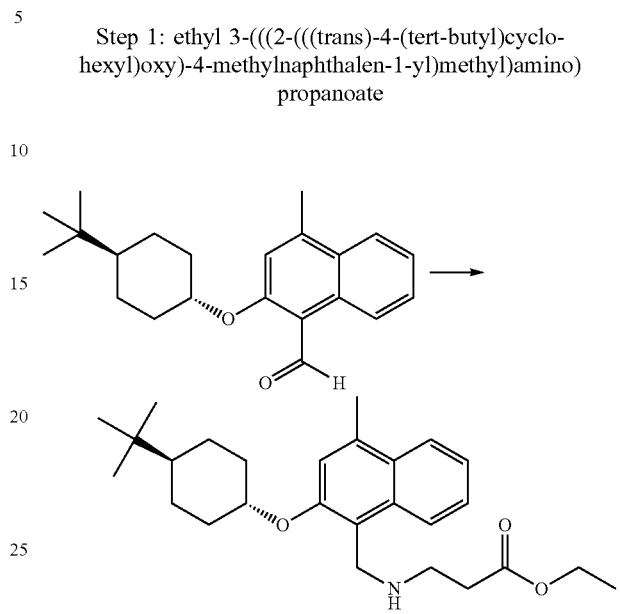

Synthesis was performed as described for methyl 2-(((2-(((trans)-4-(tert-butyl)cyclohexyl)oxy)-4-methylnaphthalen-1-yl)methyl)amino)acetate (38 mg, yield: 41%). ESI-MS: 426.30 (M+H)$^+$.

Step 2: 3-(((2-(((trans)-4-(tert-butyl)cyclohexyl)oxy)-4-methylnaphthalen-1-yl)methyl)amino)propanoic acid

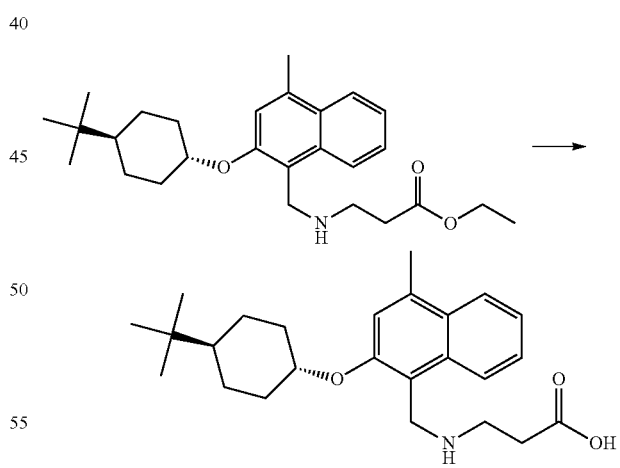

Synthesis was performed as described for 2-(((2-(((trans)-4-(tert-butyl)cyclohexyl)oxy)-4-methylnaphthalen-1-yl)methyl)amino)acetic acid. The crude was purified via HPLC to give white solid as TFA salt (22 mg, yield: 48%). ESI-MS: 398.20 (M+H)$^+$. $^1$H NMR (400 MHz, CDCl$_3$) δ 8.89 (s, 2H), 7.95 (d, 1H), 7.91 (d, 1H), 7.52 (m, 1H), 7.41 (t, 1H), 7.13 (s, 1H), 4.64 (s, 2H), 4.35 (m, 1H), 3.14 (s, 2H), 2.74-2.65 (m, 5H), 2.18 (d, 2H), 1.85 (d, 2H), 1.47 (m, 2H), 1.20-1.02 (m, 3H), 0.88 (s, 9H).

Example 5: 1-((2-(((trans)-4-(tert-butyl)cyclohexyl)oxy)-4-methylnaphthalen-1-yl)methyl)pyrrolidine-3-carboxylic acid

Step 1: methyl 1-((2-(((trans)-4-(tert-butyl)cyclohexyl)oxy)-4-methylnaphthalen-1-yl)methyl)pyrrolidine-3-carboxylate

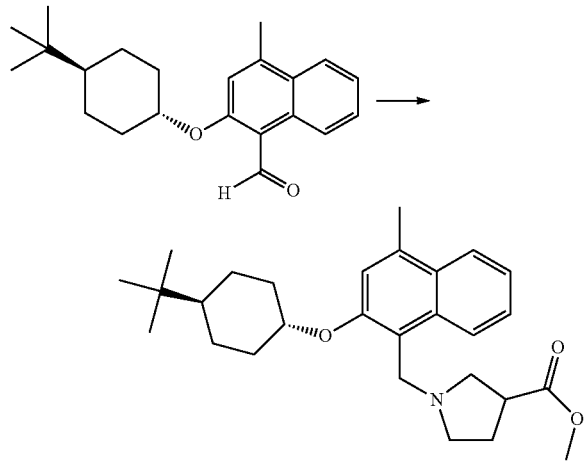

Synthesis was performed as described for 2-(((2-(((trans)-4-(tert-butyl)cyclohexyl)oxy)-4-methylnaphthalen-1-yl)methyl)amino)acetate as sticky oil (57 mg, yield: 70%). ESI-MS: 438.30 (M+H)$^+$.

Step 2: 1-((2-(((trans)-4-(tert-butyl)cyclohexyl)oxy)-4-methylnaphthalen-1-yl)methyl)pyrrolidine-3-carboxylic acid

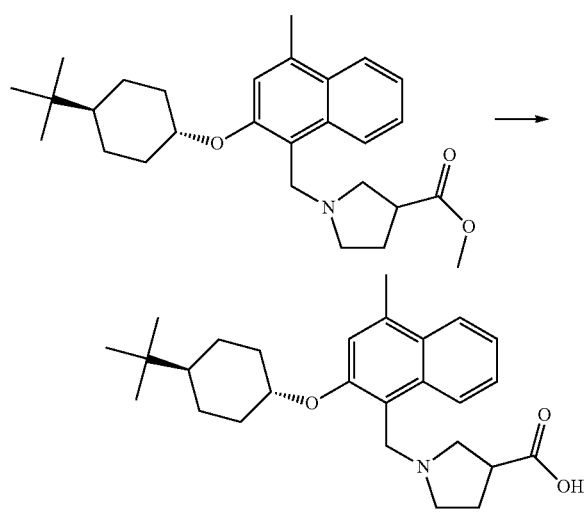

Synthesis was performed as described for 2-(((2-(((trans)-4-(tert-butyl)cyclohexyl)oxy)-4-methylnaphthalen-1-yl)methyl)amino)acetic acid. (36 mg, yield: 69%). ESI-MS: 424.30 (M+H)$^+$. $^1$H NMR (400 MHz, DMSO) δ 8.14 (d, 1H), 7.88 (d, 1H), 7.44 (t, 1H), 7.35 (m, 1H), 7.27 (s, 1H), 4.31 (m, 1H), 3.89 (s, 2H), 2.73 (t, 1H), 2.62 (s, 3H), 2.53 (m, 3H), 2.36 (m, 1H), 2.12 (d, 2H), 1.90 (m, 1H), 1.78 (d, 2H), 1.64 (m, 1H), 1.36 (m, 2H), 1.20-1.00 (m, 3H), 0.85 (s, 9H).

Example 6: 3-(((2-(((trans)-4-(tert-butyl)cyclohexyl)oxy)-4-iodonaphthalen-1-yl)methyl)amino)propanoic acid

Step 1: 3-(4-tert-butyl-cyclohexyloxy)-1-iodo-naphthalene

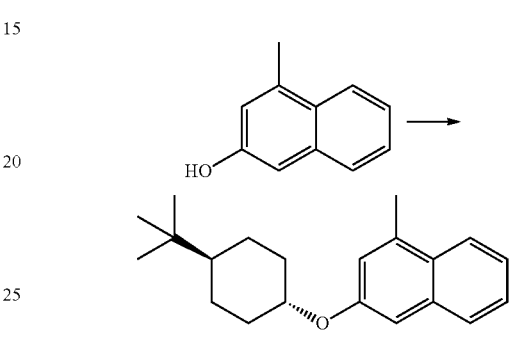

A mixture of 4-iodo-naphthalen-2-ol (1.0 g, 3.7 mmol) (Ref: a. Australian Journal of Chemistry (1963), 16 401-10. b. Journal of the Chemical Society (1943), 468-9, each of which is incorporated by reference in its entirety), methanesulfonic acid 4-tert-butyl-cyclohexyl ester (1.8 g, 7.4 mmol) and cesium carbonate (3.6 g, 11 mmol) in tert-butyl alcohol (10 mL) and 2-butanone (7 mL) was heated in a sealed vial at 100° C. for 4 hrs. The mixture was partitioned between water and dichloromethane. The organic phase was washed with brine, dried over MgSO$_4$, filtered and concentrated. The residue was purified via a silica gel column eluted with EtOAc in hexanes from 0 to 30% to give light yellow precipitate (1.10 g, yield: 73%). ESI-MS: 409.10 (M+H)$^+$.

Step 2: 2-(((trans)-4-(tert-butyl)cyclohexyl)oxy)-4-iodo-1-naphthaldehyde

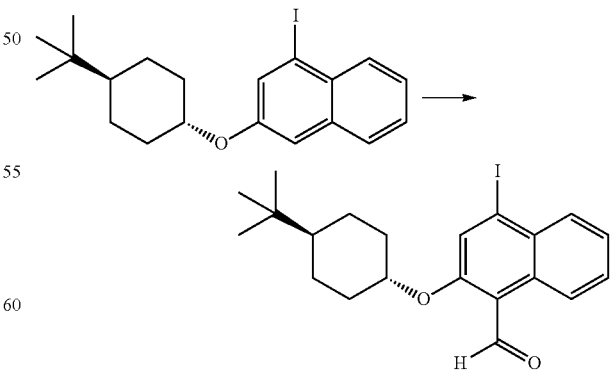

Synthesis was performed as described for 2-(((trans)-4-(tert-butyl)cyclohexyl)oxy)-4-methyl-1-naphthaldehyde (sticky oil, 700 mg, yield: 98%). ESI-MS: 437.10 (M+H)$^+$.

Step 3: ethyl 3-(((2-(((trans)-4-(tert-butyl)cyclohexyl)oxy)-4-iodonaphthalen-1-yl)methyl)amino)propanoate

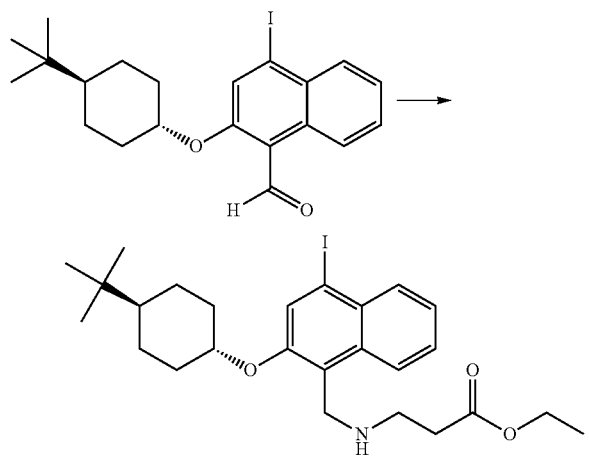

Synthesis was performed as described for 2-(((2-(((trans)-4-(tert-butyl)cyclohexyl)oxy)-4-methylnaphthalen-1-yl)methyl)amino)acetate (light brown solid, 110 mg, yield: 40%). ESI-MS: 538.20 (M+H)+.

Step 4: 3-(((2-(((trans)-4-(tert-butyl)cyclohexyl)oxy)-4-iodonaphthalen-1-yl)methyl)amino)propanoic acid

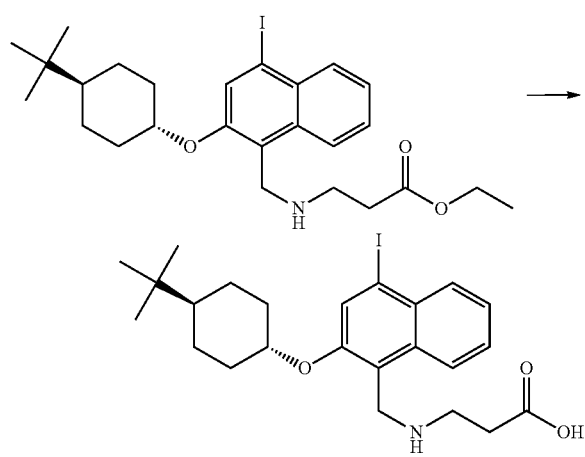

Synthesis was performed as described for 2-(((2-(((trans)-4-(tert-butyl)cyclohexyl)oxy)-4-methylnaphthalen-1-yl)methyl)amino)acetic acid. The crude was purified via HPLC to give white solid as TFA salt (7 mg, yield: 30%). ESI-MS: 510.20 (M+H)+. $^1$H NMR (400 MHz, MeOD) δ 8.13 (d, 1H), 8.12 (s, 1H), 8.05 (d, 1H), 7.66 (m, 1H), 7.54 (m, 1H), 4.72 (s, 2H), 4.54 (m, 1H), 3.14 (t, 2H), 2.81 (t, 1H), 2.66 (s, 1H), 2.28 (d, 2H), 1.94 (d, 2H), 1.60 (m, 2H), 1.30 (m, 2H), 1.16 (m, 1H), 0.93 (s, 9H).

Example 7: 1-((2-(trans-4-tert-butylcyclohexyloxy)-4-methylnaphthalen-1-yl)methyl)-4-methylpiperidine-4-carboxylic acid

Step 1: 2-(cis-4-tert-Butylcyclohexyloxy)-4-methyl-1-naphthaldehyde

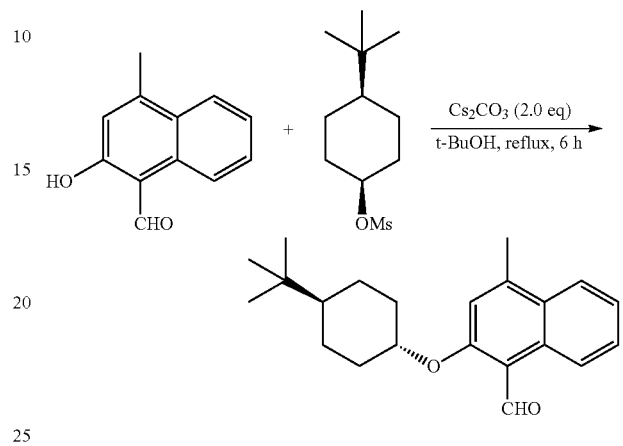

A mixture of 2-hydroxy-4-methyl-1-naphthaldehyde (4.0 g, 21.5 mmol, 1.0 eq), cis-4-tert-butylcyclohexyl methanesulfonate (10.06 g, 43 mmol, 2.0 eq) and Cs$_2$CO$_3$ (14.0 g, 43 mmol, 2.0 eq) in t-BuOH (60 mL) was heated to reflux and stirred for 6 h. After cooling down to room temperature, the reaction mixture was diluted with H$_2$O (100 mL) and extracted with EtOAc (200 mL×3). The combined organic layers were washed with brine (100 mL), dried over anhydrous Na$_2$SO$_4$, filtrated, and concentrated in vacuo. The residue was purified by column chromatography on silica gel (petroleum ether/EtOAc=10/1) to furnish the title compound (1.8 g, 26% yield) as a light yellow solid. LCMS m/z 325.2 [M+H]+.

Step 2: ethyl 1-((2-((trans)-4-tert-butylcyclohexyloxy)-4-methylnaphthalen-1-yl)methyl)-4-methylpiperidine-4-carboxylate

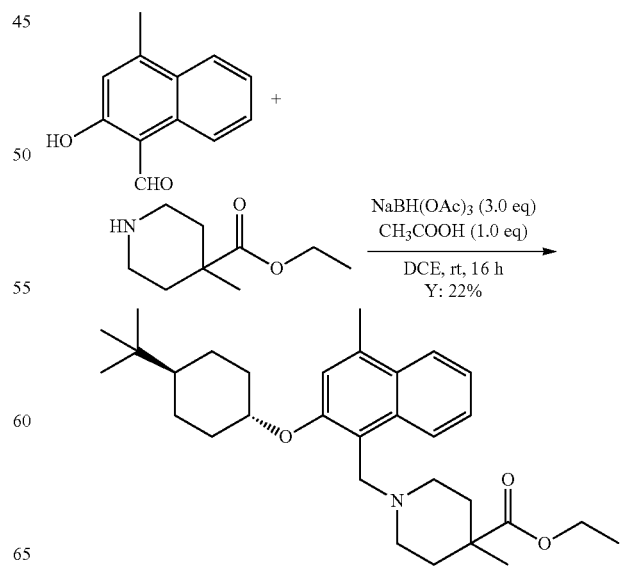

A mixture of 2-(cis-4-tert-butylcyclohexyloxy)-4-methyl-1-naphthaldehyde (150 mg, 0.46 mmol, 1.0 eq), ethyl 4-methylpiperidine-4-carboxylate (95 mg, 0.56 mmol, 1.2 eq), NaBH(OAc)$_3$ (293 mg, 1.4 mmol, 3.0 eq) and CH$_3$COOH (28 mg, 0.46 mmol, 1.0 eq) in DCE (1 mL) was stirred at room temperature for 16 h under N$_2$. The resulting mixture was then diluted with water (5 mL) and extracted with DCM (5 mL×3). The combined organic layers were washed with brine (10 mL), dried over anhydrous Na$_2$SO$_4$ and filtered. The solvent was evaporated under reduced pressure to give the residue, which was purified by column chromatography on silica gel (petroleum ether/EtOAc) to yield the title compound (50 mg, 22% yield) as a yellow oil. LCMS m/z 480.3 [M+H]$^+$;

Step 3: 1-((2-(trans-4-tert-butylcyclohexyloxy)-4-methylnaphthalen-1-yl)methyl)-4-methylpiperidine-4-carboxylic acid

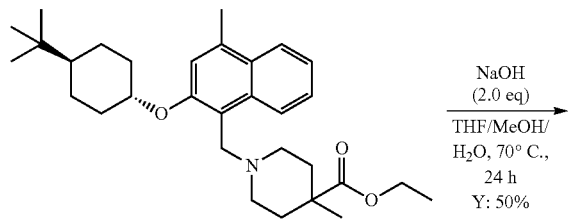

To a mixture of ethyl 1-((2-((trans)-4-tert-butylcyclohexyloxy)-4-methylnaphthalen-1-yl)methyl)-4-methylpiperidine-4-carboxylate (30 mg, 0.06 mmol, 1.0 eq) in mixed solvents (THF/MeOH/H$_2$O, 5/2/1, 1 mL) was added NaOH (5 mg, 0.12 mmol, 2.0 eq), the resulting mixture was stirred at 70° C. for 24 h, and then cooled down to room temperature. The reaction mixture was adjusted to pH=6 with dilute aq. HCl (2 M). The resulting suspension was concentrated under reduced pressure and purified by column chromatography on silica gel (DCM/MeOH=20/1) to yield the title compound (14 mg, 50% yield) as a white solid. LCMS m/z 452.2 [M+H]$^+$; $^1$H NMR (400 MHz, CD$_3$OD) δ: 8.04-7.98 (m, 2H), 7.63-7.59 (m, 1H), 7.48-7.44 (m, 1H), 7.32 (s, 1H), 4.68 (s, 2H), 4.51-4.46 (m, 1H), 3.48-3.37 (m, 2H), 3.28-3.13 (m, 2H), 2.74 (s, 3H), 2.28-2.19 (m, 4H), 1.94-1.88 (m, 2H), 1.56-1.47 (m, 2H), 1.31-1.11 (m, 8H), 0.91 (s, 9H).

Example 8: 4-(((2-((trans-4-(tert-butyl)cyclohexyl)oxy)-4-methylnaphthalen-1-yl)methyl)amino)bicyclo[2.2.2]octane-1-carboxylic acid

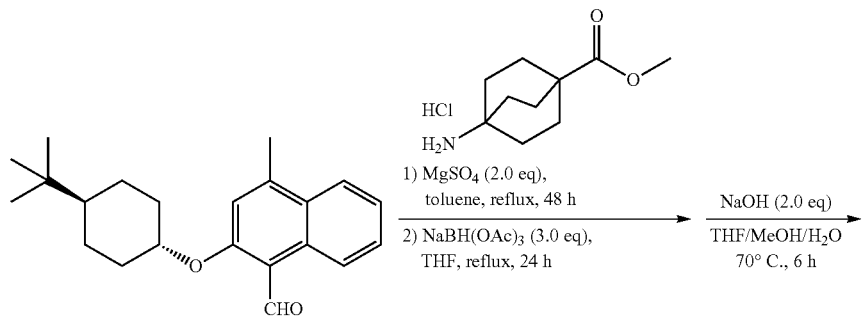

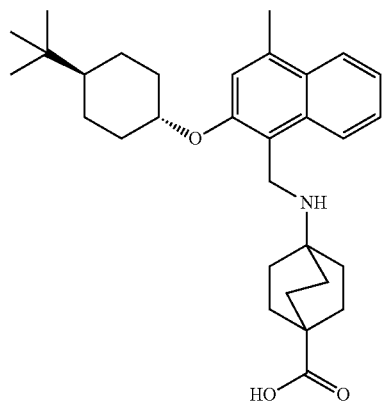

To a mixture of 2-(cis-4-tert-butylcyclohexyloxy)-4-methyl-1-naphthaldehyde (100 mg, 0.31 mmol, 1.0 eq) in toluene (1 mL) were added methyl 4-aminobicyclo[2.2.2]octane-1-carboxylate hydrochloride (81 mg, 0.37 mmol, 1.2 eq) and MgSO$_4$ (74 mg, 0.62 mmol, 2.0 eq). The resulting mixture was heated to reflux and stirred for 48 h. After being concentrated under reduced pressure, the residue was dissolved in THF (1 mL). NaBH(OAc)$_3$ (196 mg, 0.93 mmol, 3.0 eq) was added and the mixture was heated to reflux and stirred for 24 h. After cooling down to room temperature, the residue was diluted with EtOAc (5 mL). The suspension was filtered and the filtrate was concentrated under reduced pressure to give the residue, which was purified by column chromatography on silica gel (petroleum ether/EtOAc=1/1) to yield the target ester (35 mg, 23% yield) as a yellow oil. LCMS m/z 492.4 [M+H]$^+$.

Hydrolysis following standard condition gave the title compound as a white solid (20 mg, 69% yield). LCMS m/z 478.3 [M+H]$^+$; $^1$H NMR (400 MHz, CD$_3$OD) δ: 8.06-8.01 (m, 2H), 7.61-7.59 (m, 1H), 7.49-7.47 (m, 1H), 7.36 (s, 1H), 4.54 (bs, 3H), 2.74 (s, 3H), 2.32-2.29 (m, 2H), 2.16 (bs, 12H), 1.99-1.94 (m, 2H), 1.54-1.51 (m, 2H), 1.34-1.24 (m, 2H), 1.20-1.14 (m, 1H), 0.91 (s, 9H).

Example 9: 3-(((2-((trans-4-(tert-butyl)cyclohexyl)oxy)-4-methylnaphthalen-1-yl)methyl)amino)cyclobutanecarboxylic acid Using the same condition as that of ethyl 1-((2-((trans)-4-tert-butylcyclohexyloxy)-4-methylnaphthalen-1-yl)methyl)-4-methylpiperidine-4-carboxylate, ethyl 3-(((2-((trans-4-(tert-butyl)cyclohexyl)oxy)-4-methylnaphthalen-1-yl)methyl)amino)cyclobutanecarboxylate was prepared as a yellow solid (100 mg, 72% yield). LCMS m/z 452.3 [M+H]$^+$.

Hydrolysis following standard condition gave the title compound as a white solid (50 mg, 53% yield). LCMS m/z 424.3 [M+H]$^+$; $^1$H NMR (400 MHz, CD$_3$OD) δ: 8.06-8.02 (m, 2H), 7.64-7.60 (m, 1H), 7.49-7.45 (m, 1H), 7.36 (s, 1H), 4.55-4.51 (m, 3H), 3.76-3.72 (m, 1H), 2.87-2.83 (m, 1H), 2.75 (s, 3H), 2.67-2.60 (m, 2H), 2.35-2.28 (m, 4H), 1.95-1.92 (m, 2H), 1.57-1.53 (m, 2H), 1.30-1.27 (m, 2H), 1.19-1.16 (m, 1H), 0.93 (s, 9H).

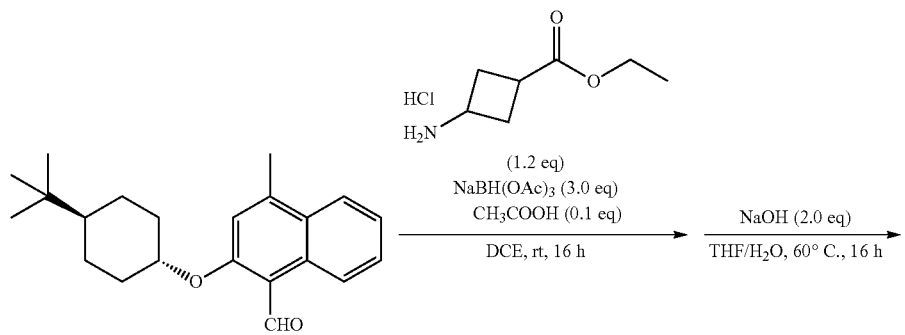

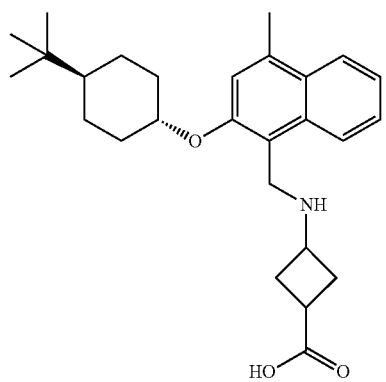

Example 10: 4-(((2-((trans-4-(tert-butyl)cyclohexyl)oxy)-4-methylnaphthalen-1-yl)methyl)amino)cyclohexanecarboxylic acid

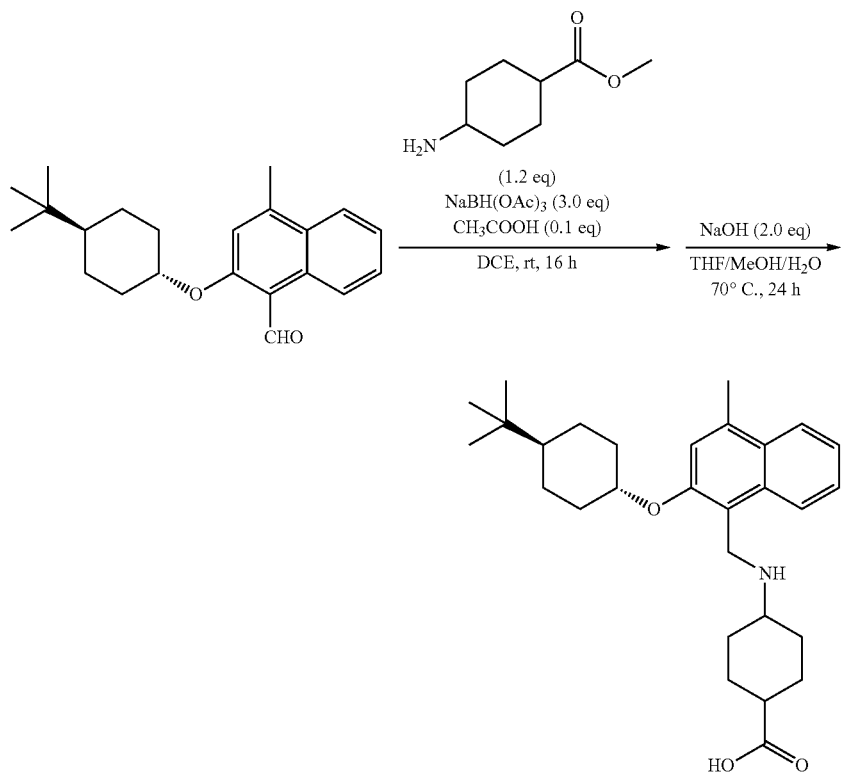

Using the same condition as that of ethyl 1-((2-((trans)-4-tert-butylcyclohexyloxy)-4-methylnaphthalen-1-yl)methyl)-4-methylpiperidine-4-carboxylate, ethyl 4-(((2-((trans-4-(tert-butyl)cyclohexyl)oxy)-4-methylnaphthalen-1-yl)methyl)amino)cyclohexanecarboxylate was prepared as a white solid (50 mg, 20% yield). LCMS m/z 480.4 [M+H]$^+$.

Hydrolysis following standard condition gave the title compound as a white solid (32 mg, 68% yield). LCMS m/z 452.3 [M+H]$^+$; $^1$H NMR (400 MHz, CD$_3$OD) δ: 8.05-8.02 (m, 2H), 7.61-7.58 (m, 1H), 7.47-7.44 (m, 1H), 7.31 (s, 1H), 4.62 (s, 2H), 4.50-4.48 (m, 1H), 3.21 (bs, 1H), 2.75 (s, 3H), 2.45 (bs, 1H), 2.31-2.19 (m, 4H), 2.02-1.79 (m, 6H), 1.59-1.48 (m, 4H), 1.33-1.15 (m, 3H), 0.92 (s, 9H).

Example 11: 3-(((2-((trans-4-(tert-butyl)cyclohexyl)oxy)-4-methylnaphthalen-1-yl)methyl)amino)cyclopentanecarboxylic acid

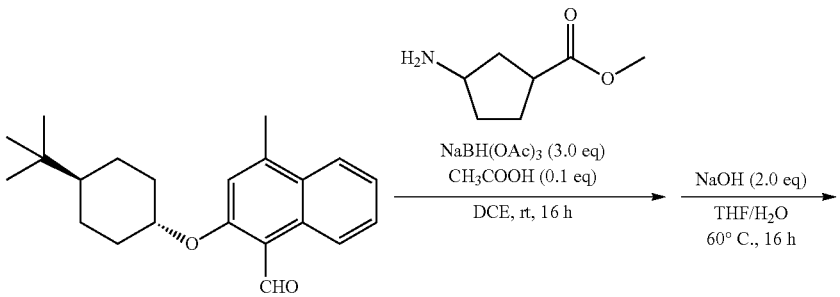

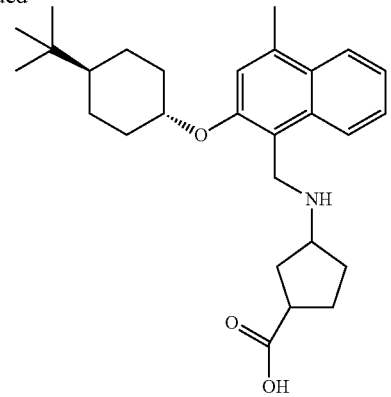

Using the same condition as that of ethyl 1-((2-((trans)-4-tert-butylcyclohexyloxy)-4-methylnaphthalen-1-yl)methyl)-4-methylpiperidine-4-carboxylate, ethyl 3-(((2-((trans-4-(tert-butyl)cyclohexyl)oxy)-4-methylnaphthalen-1-yl)methyl)amino)cyclopentanecarboxylate was obtained as a white solid (50 mg, 34% yield). LCMS m/z 466.3 [M+H]$^+$.

Hydrolysis following standard condition gave the title compound as a white solid (25 mg, 53% yield). LCMS m/z 438.3 [M+H]$^+$; $^1$H NMR (400 MHz, CD$_3$OD) δ: 8.04-8.00 (m, 2H), 7.61-7.58 (m, 1H), 7.46-7.42 (m, 1H), 7.28 (s, 1H), 4.59 (s, 2H), 4.49-4.44 (m, 1H), 3.75 (bs, 1H), 2.90 (bs, 1H), 2.73 (s, 3H), 2.33-2.26 (m, 3H), 2.16-1.87 (m, 5H), 1.99-1.91 (m, 2H), 1.56-1.47 (m, 2H), 1.31-1.12 (m, 3H), 0.92 (s, 9H).

Example 12: 2-(1-((2-((trans-4-(tert-Butyl)cyclohexyl)oxy)-4-methylnaphthalen-1-yl)methyl)piperidin-4-yl)acetic acid

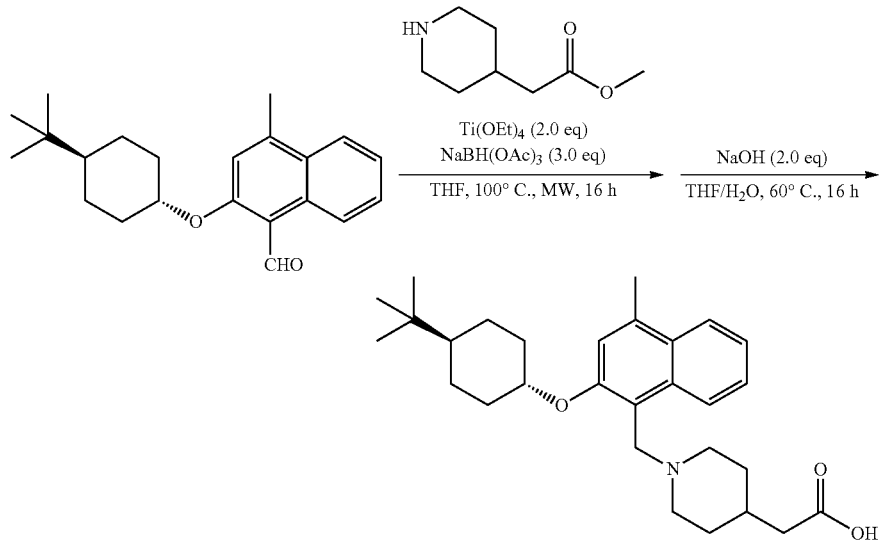

To a mixture of 2-(cis-4-tert-butylcyclohexyloxy)-4-methyl-1-naphthaldehyde (150 mg, 0.46 mmol, 1.0 eq) in THF (2.0 mL) were added methyl 2-(piperidin-4-yl)acetate (87 mg, 0.56 mmol, 1.2 eq) and Ti(OEt)$_4$ (210 mg, 0.92 mmol, 2.0 eq). The mixture was stirred at 100° C. for 16 h under microwave. After cooling down to room temperature, NaBH(OAc)$_3$ (293 mg, 1.38 mmol, 3.0 eq) was added, and the mixture was stirred at 100° C. for additional 1 h under microwave. The mixture was then diluted with water (5 mL) and Celite were added. The resulting suspension was filtered through Celite and washed with EtOAc (5 mL). The filtrate was separated, and the aqueous layer was extracted with EtOAc (5 mL×3). The combined organic phase was washed with brine (10 mL), dried over anhydrous Na$_2$SO$_4$ and concentrated in vacuo. The residue was purified by column chromatography on silica gel (petroleum ether/EtOAc=1:1) to furnish methyl 2-(1-((2-((trans-4-(tert-butyl)cyclohexyl)oxy)-4-methylnaphthalen-1-yl)methyl)piperidin-4-yl)acetate as a yellow oil (120 mg, 56% yield). LCMS m/z 480.4 [M-OMe+OEt+H]$^+$.

Hydrolysis following standard condition gave the title compound as a yellow oil (40 mg, 70% yield) LCMS m/z 452.2 [M+H]$^+$; $^1$H NMR (400 MHz, CD$_3$OD) δ: 8.06-8.04 (m, 2H), 7.64-7.60 (m, 1H), 7.49-7.45 (m, 1H), 7.37 (s, 1H), 4.68 (s, 2H), 4.47-4.48 (m, 1H), 3.53-3.47 (m, 2H), 3.16-3.10 (m, 2H), 2.75 (s, 3H), 2.28-2.25 (m, 2H), 2.76-2.11 (m, 2H), 1.95-1.91 (m, 3H), 1.55-1.49 (m, 4H), 1.38-1.26 (m, 4H), 1.18-1.15 (s, 1H), 0.93 (s, 9H).

Example 13: 2-(1-((2-((trans-4-(tert-butyl)cyclohexyl)oxy)-4-methylnaphthalen-1-yl)methyl)azetidin-3-yl)acetic acid

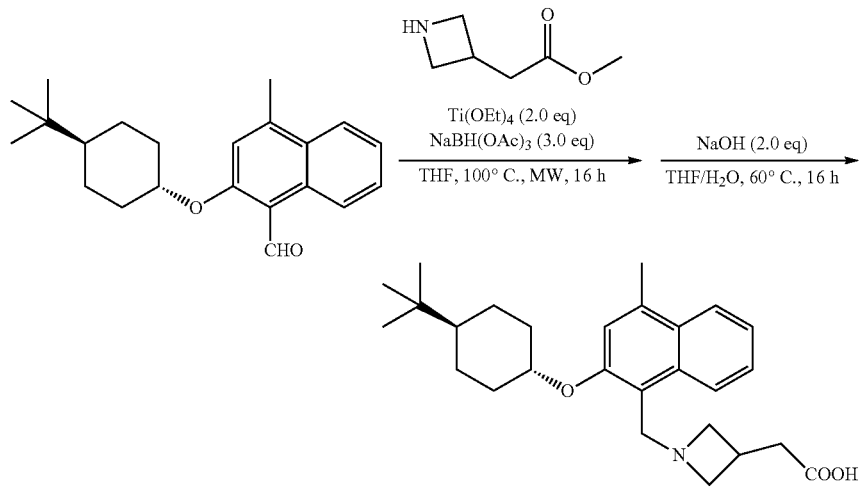

Using the same condition as that of methyl 2-(1-((2-((trans-4-(tert-butyl)cyclohexyl)oxy)-4-methylnaphthalen-1-yl)methyl)piperidin-4-yl)acetate, ethyl 2-(1-((2-((trans-4-(tert-butyl)cyclohexyl)oxy)-4-methylnaphthalen-1-yl)methyl)azetidin-3-yl)acetate was obtained as a yellow oil (50 mg, 35% yield). LCMS m/z 452.3 [M+H]$^+$.

Hydrolysis following standard condition gave the title compound as a yellow oil (25 mg, 53% yield). LCMS m/z 424.2 [M+H]$^+$; $^1$H NMR (400 MHz, CD$_3$OD) δ: 8.04-8.01 (m, 1H), 7.96-7.94 (m, 1H), 7.47-7.43 (m, 1H), 7.39-7.35 (m, 1H), 7.25 (s, 1H), 4.92 (s, 2H), 4.38-4.36 (m, 1H), 3.35-3.32 (m, 1H), 3.27-3.22 (m, 2H), 2.97-2.93 (m, 1H), 2.68 (s, 3H), 2.53-2.46 (m, 1H), 2.36 (bs, 1H), 2.23-2.18 (m, 3H), 1.89-1.86 (m, 2H), 1.47-1.40 (m, 2H), 1.27-1.10 (m, 3H), 0.90 (s, 9H).

Example 14: 2-(1-((2-((trans-4-(tert-butyl)cyclohexyl)oxy)-4-methylnaphthalen-1-yl)methyl)pyrrolidin-3-yl)acetic acid

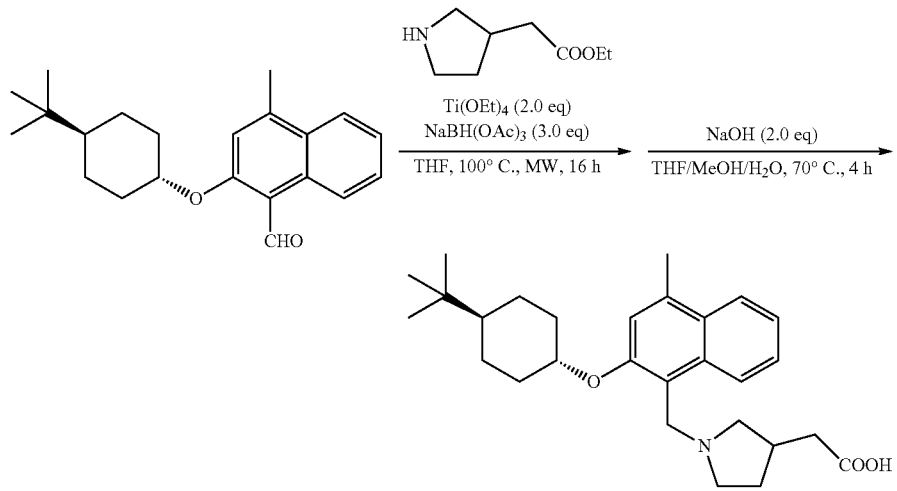

Using the same condition as that of methyl 2-(1-((2-((trans-4-(tert-butyl)cyclohexyl)oxy)-4-methylnaphthalen-1-yl)methyl)piperidin-4-yl)acetate, ethyl 2-(1-((2-((trans-4-(tert-butyl)cyclohexyl)oxy)-4-methylnaphthalen-1-yl)methyl)pyrrolidin-3-yl)acetate was obtained as a white solid (60 mg, 41% yield). LCMS m/z 466.3 [M+H]$^+$.

Hydrolysis following standard condition gave the title compound as a yellow solid (20 mg, 53% yield). LCMS m/z 438.3 [M+H]$^+$; $^1$H NMR (400 MHz, CD$_3$OD) δ: 8.03-8.01 (m, 2H), 7.61-7.57 (m, 1H), 7.47-7.43 (m, 1H), 7.30 (s, 1H), 4.75 (s, 2H), 4.49 (bs, 1H), 3.51-3.46 (m, 2H), 3.29-3.20 (m, 2H), 2.74-2.70 (m, 4H), 2.38-2.27 (m, 5H), 1.94-1.91 (m, 2H), 1.81-1.76 (m, 1H), 1.55-1.49 (m, 2H), 1.31-1.12 (m, 3H), 0.92 (s, 9H).

Example 15: 1-((2-(cyclohexyloxy)-4-methylnaph-thalen-1-yl)methyl)piperidine-4-carboxylic acid Step 1: ethyl 1-((2-hydroxy-4-methylnaphthalen-1-yl)methyl)piperidine-4-carboxylate

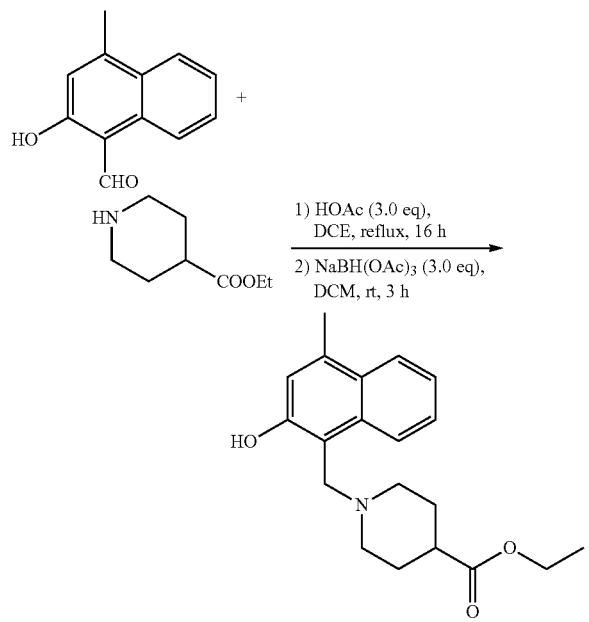

A mixture of 2-(cis-4-tert-butylcyclohexyloxy)-4-methyl-1-naphthaldehyde (3.3 g, 16 mmol, 1.0 eq), ethyl piperidine-4-carboxylate (3.77 g 24 mmol, 1.5 eq) and HOAc (2.88 g, 48 mmol, 3 eq) in DCE (30 mL) was stirred at 80° C. for 16 h. After the mixture was cooled to room temperature, NaBH(OAc)₃ (10.2 g, 48 mmol, 3 eq) was added. The mixture was stirred at room temperature, for 3 h. Then, 100 mL EtOAc was added and the organic layer was washed with NaHCO₃ (aq., sat.). After filtration, the organic solvent was removed in vacuo and the residue was purified by column chromatography on silica gel (petroleum ether/EtOAc=20:1) to give ethyl 1-((2-hydroxy-4-methylnaphtha-len-1-yl)methyl)piperidine-4-carboxylate as a yellow solid (1.05 g, 20% yield). LCMS m/z 328.2 [M+H]⁺.

Step 2: 1-((2-(cyclohexyloxy)-4-methylnaphthalen-1-yl)methyl)piperidine-4-carboxylic acid

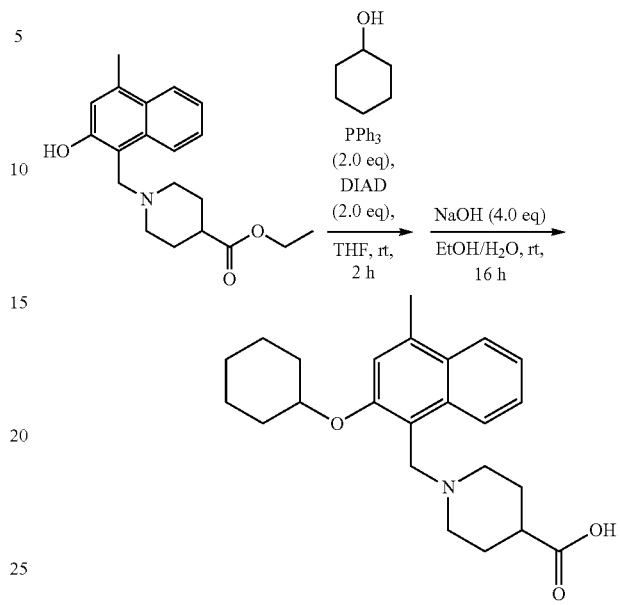

A mixture of ethyl 1-((2-hydroxy-4-methylnaphthalen-1-yl)methyl)piperidine-4-carboxylate (200 mg, 0.61 mmol, 1.0 eq), cyclohexanol (120 mg, 1.22 mmol, 2 eq) and PPh₃ (320 mg, 1.22 mmol, 2 eq) in THF (0.3 mL) was stirred at rt. Then DIAD (247 mg, 1.22 mmol, 2 eq) was added, and the mixture was stirred at room temperature for 2 h. The organic solvent was removed in vacuo and the residue was purified by column chromatography on silica gel (petroleum ether/EtOAc=5/1) to give ethyl 1-((2-(cyclohexyloxy)-4-methylnaphthalen-1-yl)methyl)piperidine-4-carboxylate as a yellow oil (90 mg, 35% yield). LCMS m/z 409.9 [M+H]⁺.

Hydrolysis following standard condition gave the title as a white solid (80 mg, 78% yield). LCMS m/z 498.1 [M+H]⁺; ¹H NMR (400 MHz, DMSO-d₆) δ: 8.12 (d, J=8.4 Hz, 1H), 7.89 (d, J=8.0 Hz, 1H), 7.47 (t, J=8.0 Hz, 1H), 7.37 (t, J=8.0 Hz, 1H), 7.26 (s, 1H), 4.50-4.46 (m, 1H), 3.82 (s, 2H), 2.82-2.79 (m, 2H), 2.63 (s, 3H), 2.21-2.15 (m, 1H), 2.08 (t, J=10.4 Hz, 2H), 1.91-1.88 (m, 2H), 1.73-1.71 (m, 4H), 1.56-1.51 (m, 4H), 1.46-1.31 (m, 4H).

Example 16: 1-((4-methyl-2-((trans-4-(tert-pentyl)cyclohexyl)oxy)naphthalen-1-yl)methyl)piperidine-4-carboxylic acid

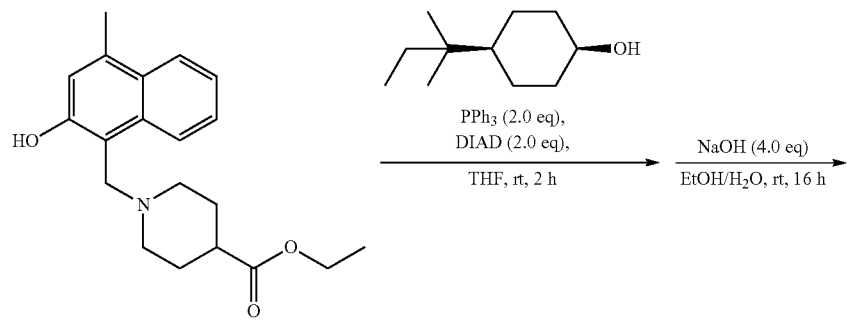

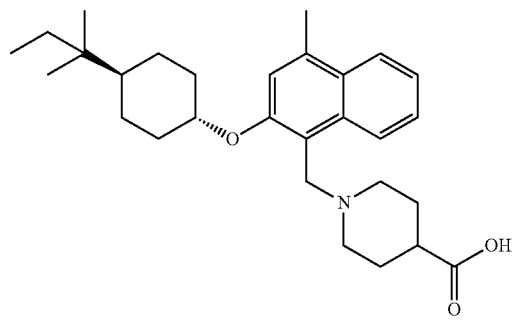

Using the same condition as that of ethyl 1-((2-(cyclohexyloxy)-4-methylnaphthalen-1-yl)methyl)piperidine-4-carboxylate, ethyl 1-((4-methyl-2-((trans-4-(tert-pentyl)cyclohexyl)oxy)naphthalen-1-yl)methyl)piperidine-4-carboxylate was obtained as a yellow oil. (70 mg, 23% yield). LCMS m/z 480.4 [M+H]⁺.

Hydrolysis following standard condition gave the title compound as a white solid (60 mg, 91% yield). LCMS m/z 458.9 [M+H]⁺; ¹H NMR (400 MHz, CD₃OD) δ: 8.05 (t, J=8.0 Hz, 2H), 7.63 (t, J=7.6 Hz, 1H), 7.48 (t, J=7.6 Hz, 1H), 7.38 (s, 1H), 4.71 (s, 2H), 4.56-4.49 (m, 1H), 3.54-3.51 (m, 2H), 3.23-3.16 (m, 2H), 2.76 (s, 3H), 2.43-2.36 (m, 1H), 2.29-2.26 (m, 2H), 2.07-1.87 (m, 6H), 1.58-1.50 (m, 2H), 1.38-1.29 (m, 5H), 0.87-0.84 (m, 9H).

Example 17: 1-((4-methyl-2-((trans-4-phenylcyclohexyl)oxy)naphthalen-1-yl)methyl)piperidine-4-carboxylic acid Using the same condition as that of ethyl 1-((2-(cyclohexyloxy)-4-methylnaphthalen-1-yl)methyl)piperidine-4-carboxylate, ethyl 1-((4-methyl-2-((trans-4-phenylcyclohexyl)oxy)naphthalen-1-yl)methyl)piperidine-4-carboxylate was obtained as a yellow oil (40 mg, 13% yield). LCMS m/z 486.3 [M+H]⁺.

Hydrolysis following standard condition gave the title compound as a white solid (23 mg, 61% yield). LCMS m/z 458.3 [M+H]⁺; ¹H NMR (400 MHz, CDCl₃) δ: 8.28 (d, J=8.8 Hz, 1H), 7.91 (d, J=8.4 Hz, 1H), 7.49 (t, J=7.6 Hz, 1H), 7.39-7.29 (m, 3H), 7.24-7.19 (m, 3H), 7.15 (s, 1H), 4.58 (s, 2H), 4.47-4.41 (m, 1H), 3.45-3.42 (m, 2H), 2.71 (s, 3H), 2.64-2.48 (m, 3H), 2.26-2.13 (m, 3H), 2.03-1.86 (m, 6H), 1.70-1.51 (m, 4H).

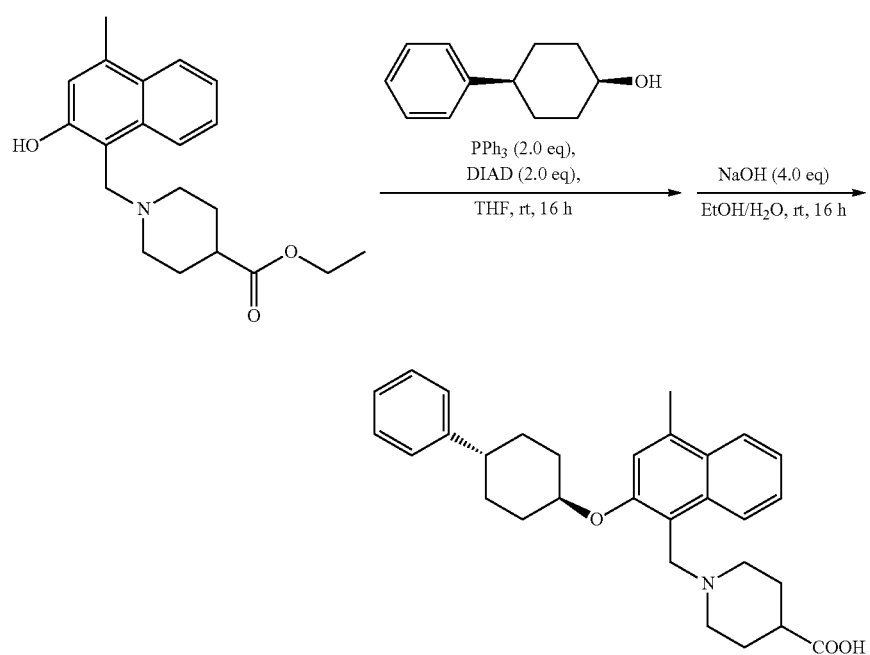

Example 18: 1-((4-methyl-2-(spiro[4.5]decan-8-yloxy)naphthalen-1-yl)methyl)piperidine-4-carboxylic acid

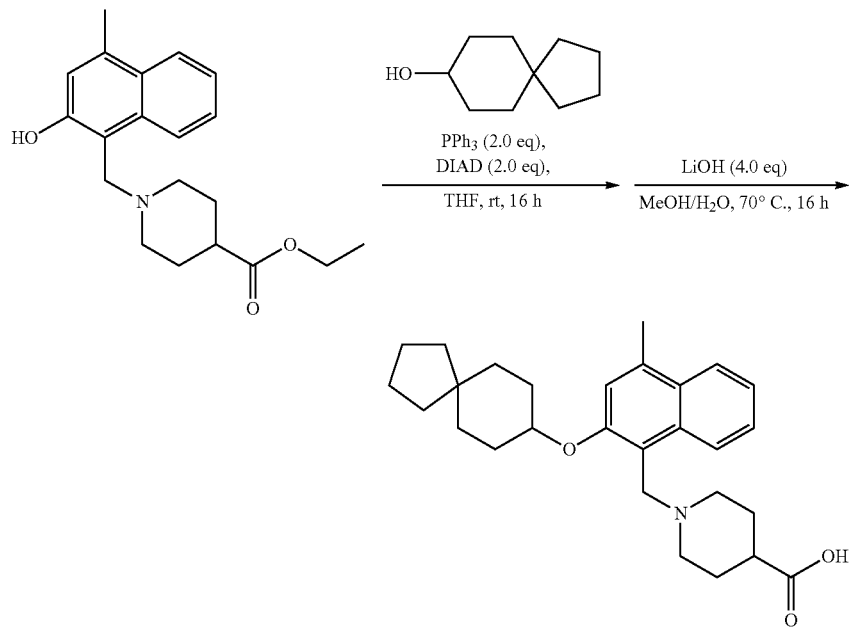

Using the same condition as that of ethyl 1-((2-(cyclohexyloxy)-4-methylnaphthalen-1-yl)methyl)piperidine-4-carboxylate, ethyl 1-((4-methyl-2-(spiro[4.5]decan-8-yloxy)naphthalen-1-yl)methyl)piperidine-4-carboxylate was obtained as a yellow oil (60 mg, 28% yield). LCMS m/z 464.1 [M+H]$^+$.

Hydrolysis following standard condition gave the title compound as a yellow oil (30 mg, 54% yield). LCMS m/z 436.2 [M+H]$^+$; $^1$H NMR (400 MHz, CD$_3$OD) δ: 8.05 (d, J=9.2 Hz, 2H), 7.62 (t, J=8.0 Hz, 1H), 7.48 (t, J=8.0 Hz, 1H), 7.37 (s, 1H), 4.71 (s, 2H), 4.66-4.63 (m, 1H), 3.54-3.51 (m, 2H), 3.20-3.15 (m, 2H), 2.75 (s, 3H), 2.39-2.37 (m, 1H), 2.07-1.92 (m, 6H), 1.79-1.43 (m, 14H).

Example 19: 1-((4-methyl-2-(spiro[5.5]undecan-3-yloxy)naphthalen-1-yl)methyl)piperidine-4-carboxylic acid

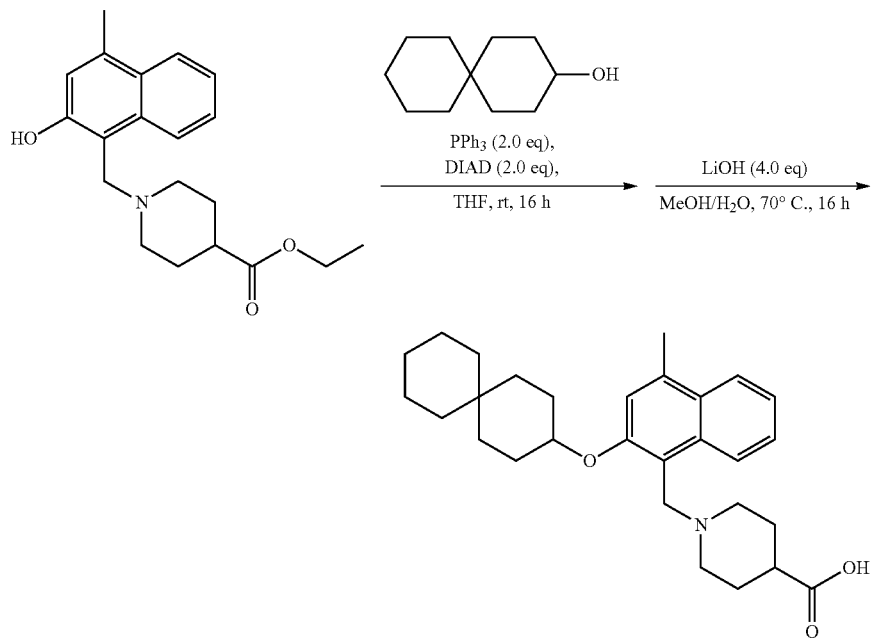

Using the same condition as that of ethyl 1-((2-(cyclohexyloxy)-4-methylnaphthalen-1-yl)methyl)piperidine-4-carboxylate, ethyl 1-((4-methyl-2-(spiro[5.5]undecan-3-yloxy)naphthalen-1-yl)methyl)piperidine-4-carboxylate was obtained as a yellow oil (150 mg, 34% yield). LCMS m/z 478.1 [M+H]⁺;

Hydrolysis following standard condition gave the title compound as a white solid (50 mg, 53% yield). LCMS m/z 450.1 [M+H]⁺; ¹H NMR (400 MHz, CD₃OD) δ: 7.95 (t, J=7.6 Hz, 2H), 7.52 (t, J=7.6 Hz, 1H), 7.38 (t, J=7.6 Hz, 1H), 7.27 (s, 1H), 4.62 (s, 2H), 4.54 (bs, 1H), 3.42 (bs, 2H), 3.10 (bs, 2H), 2.65 (s, 3H), 2.28 (bs, 1H), 1.93-1.62 (m, 10H), 1.40-1.22 (m, 12H).

Example 20: 1-((2-((cis-4-(tert-Butyl)cyclohexyl)oxy)-4-methylnaphthalen-1-yl)methyl)piperidine-4-carboxylic acid carboxylate, ethyl 1-((2-((cis-4-(tert-butyl)cyclohexyl)oxy)-4-methylnaphthalen-1-yl)methyl)piperidine-4-carboxylate was obtained as a yellow oil (40 mg, 10% yield). LCMS m/z 466.1 [M+H]⁺.

Hydrolysis following standard condition gave the title compound as a yellow solid (20 mg, 54% yield). LCMS m/z 438.2 [M+H]⁺; ¹H NMR (400 MHz, CD₃OD) δ: 7.95 (t, J=9.2 Hz, 2H), 7.51 (t, J=7.6 Hz, 1H), 7.36 (t, J=7.6 Hz, 1H), 7.25 (s, 1H), 4.82 (bs, 1H), 4.64 (s, 2H), 3.45-3.42 (m, 1H), 3.08-3.03 (m, 2H), 2.63 (s, 3H), 2.27 (bs, 1H), 2.10-1.83 (m, 6H), 1.58-1.06 (m, 8H), 0.83 (s, 9H).

Example 21: 1-((4-methyl-2-((cis-4-methylcyclohexyl)oxy)naphthalen-1-yl)methyl)piperidine-4-carboxylic acid

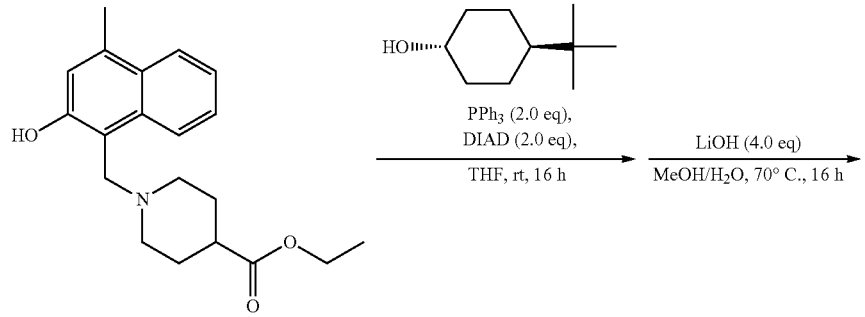

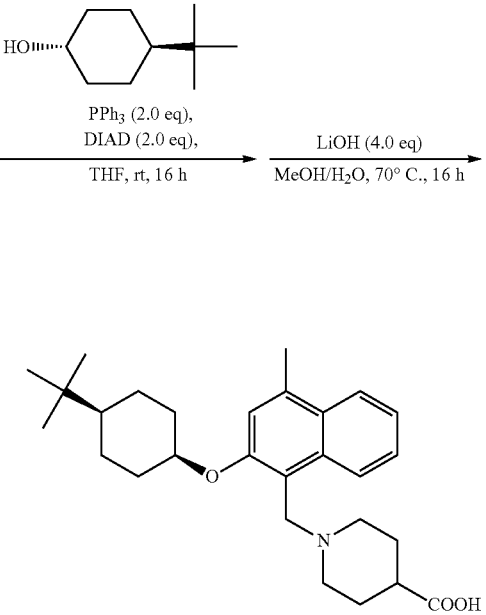

Using the same condition as that of ethyl 1-((2-(cyclohexyloxy)-4-methylnaphthalen-1-yl)methyl)piperidine-4-

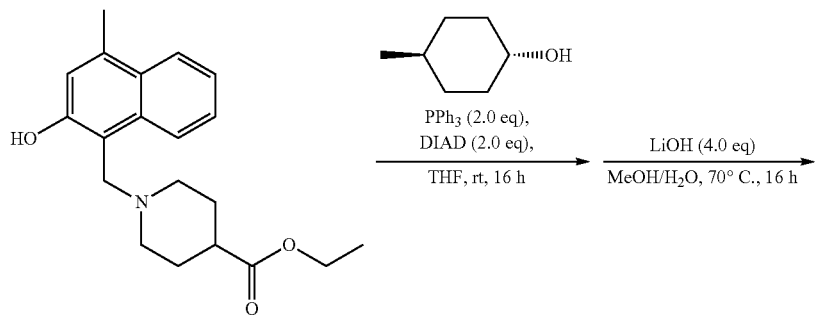

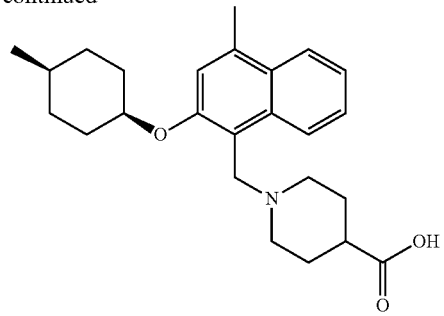

Using the same condition as that of ethyl 1-((2-(cyclohexyloxy)-4-methylnaphthalen-1-yl)methyl)piperidine-4-carboxylate, ethyl 1-((4-methyl-2-((cis-4-methylcyclohexyl)oxy)naphthalen-1-yl)methyl)piperidine-4-carboxylate was obtained as a yellow oil (30 mg, 8%). LCMS m/z 424.2 [M+H]+.

Hydrolysis following standard condition gave the title compound as a white solid (5 mg, 38% yield). LCMS m/z 396.1 [M+H]+; 1H NMR (400 MHz, CD3OD) δ: 8.11 (d, J=8.4 Hz, 1H), 7.90 (d, J=8.4 Hz, 1H), 7.47-7.34 (m, 2H), 7.25 (s, 1H), 4.75 (bs, 1H), 3.85 (s, 2H), 2.85-2.82 (m, 2H), 2.63 (s, 3H), 2.11-2.06 (m, 3H), 1.93-1.89 (m, 2H), 1.73-1.70 (m, 2H), 1.62-1.55 (m, 2H), 1.50-1.36 (m, 7H), 0.92 (d, J=5.2 Hz, 3H).

Example 22: 1-((2-((cis-4-Ethylcyclohexyl)oxy)-4-methylnaphthalen-1-yl)methyl)piperidine-4-carboxylic acid Using the same condition as that of ethyl 1-((2-(cyclohexyloxy)-4-methylnaphthalen-1-yl)methyl)piperidine-4-carboxylate, ethyl 1-((2-((cis-4-ethylcyclohexyl)oxy)-4-methylnaphthalen-1-yl)methyl)piperidine-4-carboxylate was obtained as a yellow oil (60 mg, 30% yield). LCMS m/z 438.2 [M+H]+.

Hydrolysis following standard condition gave the title compound as a yellow solid (40 mg, 71% yield). LCMS m/z 410.3 [M+H]+; 1H NMR (400 MHz, CD3OD) δ: 8.06 (d, J=8.8 Hz, 2H), 7.63 (t, J=8.0 Hz, 1H), 7.48 (t, J=8.0 Hz, 1H), 7.37 (s, 1H), 4.92 (bs, 1H), 4.73 (s, 2H), 3.55-3.52 (m, 2H), 3.20-3.15 (m, 2H), 2.75 (s, 3H), 2.41-2.36 (m, 1H), 2.31-1.69 (m, 10H), 1.41-1.37 (m, 5H), 0.96 (t, J=7.0 Hz, 3H).

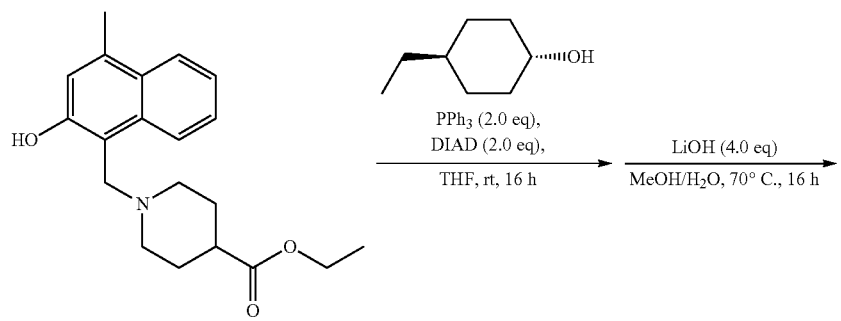

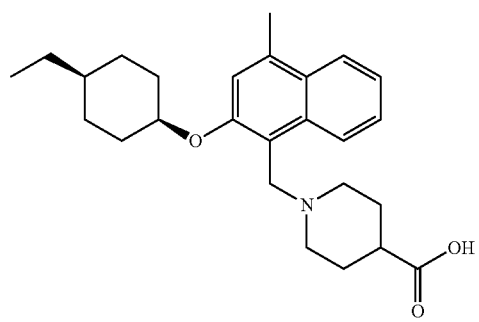

Example 23: 1-((4-Methyl-2-((cis-4-phenylcyclohexyl)oxy)naphthalen-1-yl)methyl)piperidine-4-carboxylic acid

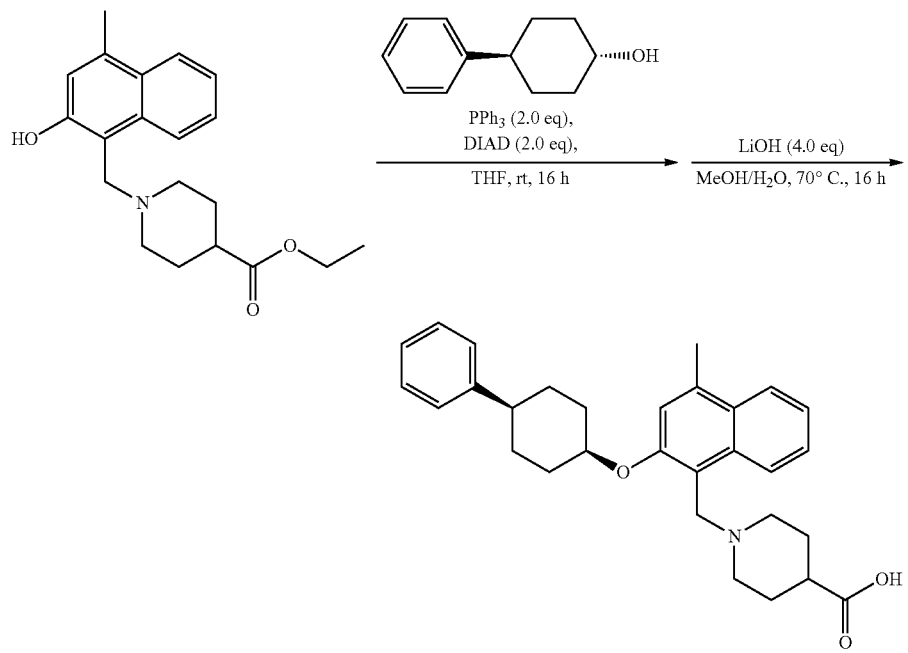

Using the same condition as that of ethyl 1-((2-(cyclohexyloxy)-4-methylnaphthalen-1-yl)methyl)piperidine-4-carboxylate, ethyl 1-((4-methyl-2-((cis-4-phenylcyclohexyl)oxy)naphthalen-1-yl)methyl)piperidine-4-carboxylate was obtained, as a yellow oil (40 mg, 18% yield). LCMS m/z 486.3 [M+H]$^+$.

Hydrolysis following standard condition gave the title compound as a yellow oil (20 mg, 53% yield). LCMS m/z 458.3 [M+H]$^+$; $^1$H NMR (400 MHz, CDCl$_3$) δ: 8.33 (d, J=8.8 Hz, 1H), 7.88 (d, J=8.4 Hz, 1H), 7.46 (t, J=7.6 Hz, 1H), 7.36-7.14 (m, 6H), 7.11 (s, 1H), 4.81 (bs, 1H), 4.56 (s, 2H), 3.39-3.36 (m, 2H), 2.69 (s, 3H), 2.65-2.43 (m, 3H), 2.19-2.12 (m, 3H), 1.96-1.71 (m, 10H).

Example 24: 1-((4-methyl-2-((trans-4-(trimethylsilyl)cyclohexyl)oxy)naphthalen-1-yl)methyl)piperidine-4-carboxylic acid

Step 1: (4-Methoxyphenyl)trimethylsilane

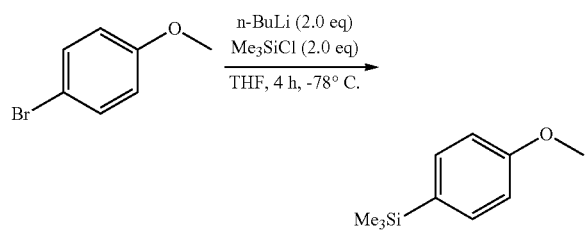

4-Bromoanisole (9.35 g, 50.0 mmol, 1.0 eq) was dissolved in anhydrous THF (200 mL). Me$_3$SiCl (12.7 mL, 100.0 mmol, 2.0 eq) was added at 0° C. followed by n-BuLi (2.5 M in hexanes, 40 mL, 100.0 mmol, 2.0 eq). The reaction mixture was stirred at room temperature for 1 h. Water (150 mL) was then added, the organic layer was separated and the aqueous layer was extracted with Et$_2$O (150 mL×2). The combined organic extracts were dried over anhydrous Na$_2$SO$_4$, filtered and concentrated in vacuo to give (4-methoxyphenyl)trimethylsilane as a light yellow oil (8.1 g, 90% yield). $^1$H NMR (300 MHz, CDCl$_3$) δ: 7.48 (d, J=11.2 Hz, 2H), 6.95 (d, J=11.2 Hz, 2H), 3.84 (s, 3H), 0.27 (s, 9H).

Step 2: 4-(Trimethylsilyl)cyclohexanone

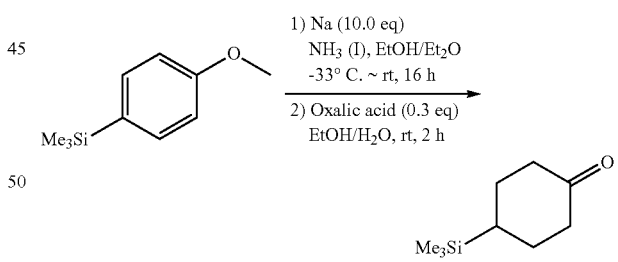

Ammonia (100 mL) was condensed at −78° C. (4-methoxyphenyl)trimethylsilane (18.0 g, 0.1 mol, 1.0 eq) in anhydrous Et$_2$O (110 mL) was added followed by EtOH (80 mL) and sodium (23.0 g, 1.0 mol, 10.0 eq) portionwise at −33° C. Additional EtOH ((50 mL) was added and ammonia was allowed to evaporated over 16 h. The water (250 mL) was added to the residue and the mixture was extracted with Et$_2$O (250 mL×3). The combined organic extracts were dried over anhydrous Na$_2$SO$_4$, filtered and concentrated in vacuo. The crude product was dissolved in EtOH (20 mL) and H$_2$O (20 mL) and oxalic acid (2.71 g, 0.03 mol, 0.3 eq) was then added. The resulting colorless solution was stirred at room temperature for 2 h. Water (100 mL) was then added and the mixture was extracted with Et₂O (100 mL×3). The combined organic extracts were washed with brine, dried over anhydrous Na₂SO₄, filtered and concentrated in vacuo. The residue was purified by column chromatography on silica gel (petroleum ether/EtOAc=10:1) to furnish 4-(trimethylsilyl)cyclohexanone as a light yellow oil (14.0 g, 72% yield). ¹H NMR (300 MHz, CDCl₃) δ: 2.44-2.39 (m, 2H), 2.33-2.22 (m, 2H), 2.11-2.05 (m, 2H), 1.53-1.47 (m, 2H), 0.96-0.87 (m, 1H), 0.00 (s, 9H).

Step 3: Cis-4-(trimethylsilyl)cyclohexanol

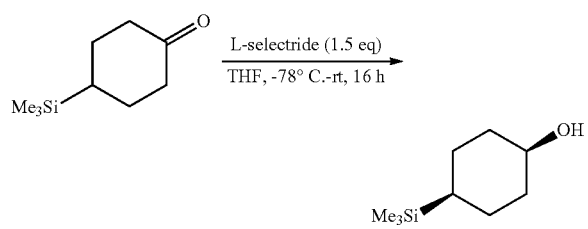

To a solution of L-selectride (165 mL, 0.165 mol, 1.5 eq) in anhydrous THF (200 mL) at −78° C. was added dropwise a solution of 4-(trimethylsilyl)cyclohexanone (20 g, 0.11 mol, 1.0 eq) in anhydrous THF (100 mL). The temperature was maintained for 3 h, and then the reaction mixture was stirred at room temperature for 16 h. Then the mixture was cooled to 0° C. before being quenched with water. The resulting mixture was warmed up to room temperature, and then sodium hydroxide aqueous solution (80 mL, 3 M) was added, followed by hydrogen peroxide (80 mL, 30%). After being stirred for 3 h, the mixture was extracted with EtOAc (300 mL×3), and the combined organic layers were washed with H₂O and brine, dried over Na₂SO₄, concentrated to give a residue which was purified by column chromatography on silica gel (petroleum ether/EtOAc=10:1) to obtain the product cis-4-(trimethylsilyl)cyclohexanol as a white solid (10.0 g, 51% yield). ¹H NMR (300 MHz, CDCl₃) δ: 4.05 (s, 1H), 1.75 (bs, 2H), 1.58-1.43 (m, 7H), 0.55 (bs, 1H), 0.00 (s, 9H).

Step 4: (trans)-4-(trimethylsilyl)cyclohexanol

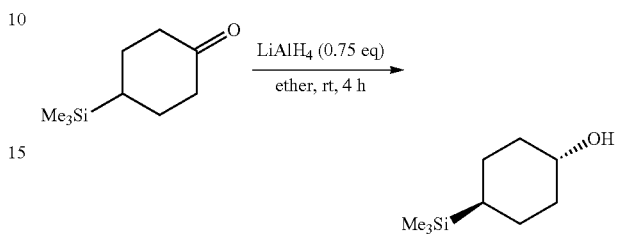

A 500-ml round-bottomed flask was placed with LiAlH₄ (1.8 g, 50 mmol, 0.75 eq) and anhydrous ether (150 mL). To this mixture was added dropwise a solution of 4-(trimethylsilyl)cyclohexanone (11.3 g, 66 mmol, 1.0 eq) in ether (75 mL). After the addition, the mixture was stirred at room temperature for 4 h; then the reaction was quenched carefully with dilute hydrochloric acid (2 M). The aqueous layer was extracted with ether (3×250 mL), the combined ether solutions were dried over magnesium sulfate, and the ether was removed under reduced pressure to give the residue, which was purified by column chromatogram (Petroleum ether/EtOAc=10:1) to obtain the title compound as a white solid (9.2 g, 45% yield). ¹H NMR (300 MHz, CDCl₃) δ: 3.58-3.52 (m, 1H), 2.09-2.06 (m, 2H), 1.83-1.79 (m, 2H), 1.29-1.13 (m, 5H), 0.50-0.42 (m, 1H), 0.00 (s, 9H).

Step 5: 1-((4-methyl-2-((trans-4-(trimethylsilyl)cyclohexyl)oxy)naphthalen-1-yl)methyl)piperidine-4-carboxylic acid

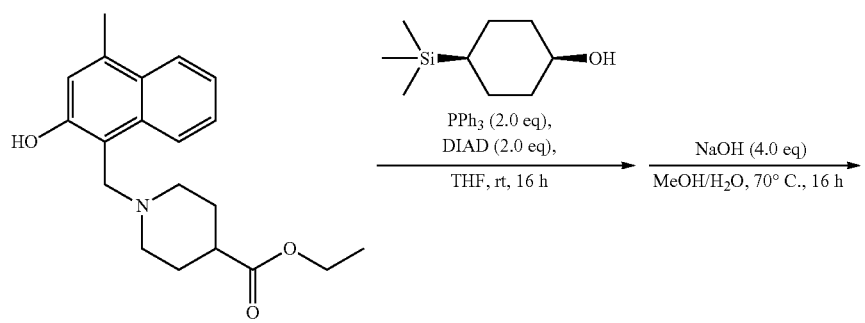

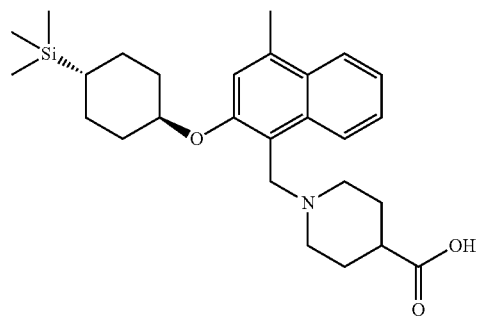

Using the same condition as that of ethyl 1-((2-(cyclohexyloxy)-4-methylnaphthalen-1-yl)methyl)piperidine-4-carboxylate, ethyl 1-((4-methyl-2-((trans-4-(trimethylsilyl)cyclohexyl)oxy)naphthalen-1-yl)methyl)piperidine-4-carboxylate was obtained as a yellow oil (60 mg, 26% yield). LCMS m/z 482.0 [M+H]⁺.

Hydrolysis following standard condition gave the title compound as a white solid (40 mg, 70% yield). LCMS m/z 498.1 [M+H]⁺; ¹H NMR (400 MHz, CDCl₃) δ: 8.03 (t, J=7.2 Hz, 2H), 7.61 (t, J=7.6 Hz, 1H), 7.45 (t, J=7.6 Hz, 1H), 7.37 (s, 1H), 4.69 (s, 2H), 4.56-4.48 (m, 1H), 3.52-3.49 (m, 2H), 3.20-3.14 (m, 2H), 2.74 (s, 3H), 2.40-2.35 (m, 1H), 2.28-2.25 (m, 2H), 2.05-1.87 (m, 6H), 1.54-1.44 (m, 2H), 1.39-1.29 (m, 2H), 0.64-0.56 (m, 1H), 0.00 (m, 9H).

Example 25: 1-((4-methyl-2-((cis-4-(trimethylsilyl)cyclohexyl)oxy)naphthalen-1-yl)methyl)piperidine-4-carboxylic acid

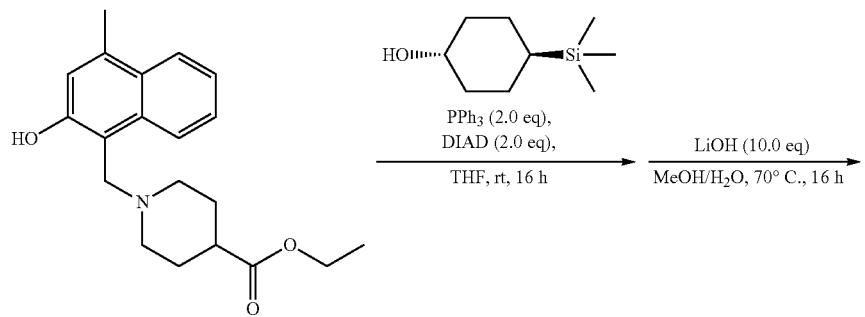

Using the same condition as that of ethyl 1-((2-(cyclohexyloxy)-4-methylnaphthalen-1-yl)methyl)piperidine-4-carboxylate, ethyl 1-((4-methyl-2-((cis-4-(trimethylsilyl)cyclohexyl)oxy)naphthalen-1-yl)methyl)piperidine-4-carboxylate was obtained, as a yellow oil (45 mg, 11% yield). LCMS m/z 482.0 [M+H]⁺.

Hydrolysis following standard condition gave the title compound as a white solid (20 mg, 48% yield).

¹H NMR (400 MHz, CD₃OD) δ: 8.04-8.01 (m, 2H), 7.60 (t, J=5.6 Hz, 1H), 7.46-7.43 (m, 1H), 7.32 (s, 1H), 4.97 (bs, 1H), 4.70 (s, 2H), 3.51-3.49 (m, 2H), 3.11 (bs, 2H), 2.71 (s, 3H), 2.37-2.32 (m, 1H), 2.13-1.84 (m, 6H), 1.71-1.48 (m, 6H), 0.75-0.69 (m, 1H), 0.00 (m, 9H). LCMS m/z 454.2 [M+H]⁺

Example 26: 1-((2-(((trans)-4-(tert-butyl)cyclohexyl)oxy)-4-(trifluoromethyl)naphthalen-1-yl)methyl)piperidine-4-carboxylic acid Step 1: 3-(((trans)-4-(tert-Butyl)cyclohexyl)oxy)-1-iodonaphthalene

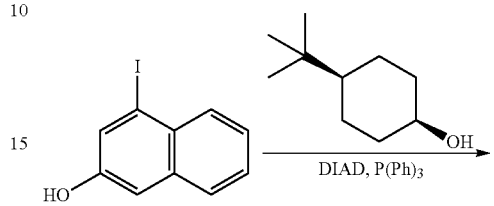

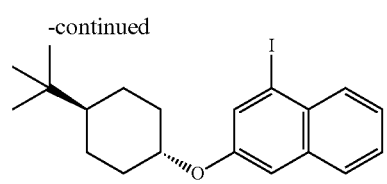

To a solution of 4-iodo-2-naphthol (5.4 g, 20 mmol, 1.0 equiv) and cis-4-tert-butyl-1-cyclohexanol (3.75 g, 24 mmol, 1.2 equiv) in anhydrous toluene (100 mL) was added triphenylphosphine (7.87 g, 30 mmol, 2.0 equiv), followed by the addition of diisopropyl azodicarboxylate (5.91 mL, 30 mmol, 2.0 equiv) dropwise at room temperature. The resulting mixture was refluxed for 6 h. After cooling to room temperature, the mixture was washed with water, and the aqueous layer was back-extracted with ethyl acetate (2×200 mL). The combined organic layers were washed with saturated brine, dried over sodium sulfate and concentrated under reduced pressure. The residue was purified on an AnaLogix (65-400 g) column, eluting with a gradient of 0 to 5% ethyl acetate in heptanes to give the title compound (3.6 g, 44% yield) as a pale-yellow solid.

$^1$H NMR (300 MHz, CDCl$_3$) δ ppm 7.95 (d, 1H), 7.78 (s, 1H), 7.61 (d, 1H), 7.41 (m, 2H), 7.16 (s, 1H), 4.22 (m, 1H), 2.23 (m, 2H), 1.87 (m, 2H), 1.42 (m, 2H), 1.18 (m, 3H), 0.88 (s, 9H).

Step 2: 2-(((trans)-4-(tert-butyl)cyclohexyl)oxy)-4-iodo-1-naphthaldehyde

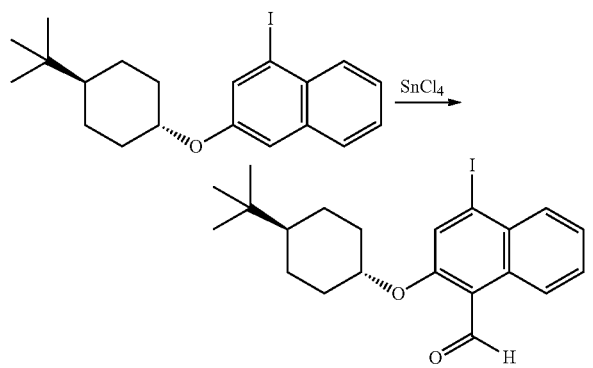

Tin(IV) chloride (0.79 mL, 6.75 mmol, 1.35 equiv) was added dropwise at 0-5° C. to a solution of 3-(((1r,4r)-4-(tert-butyl)cyclohexyl)oxy)-1-iodonaphthalene (2.04 g, 5 mmol, 1.0 equiv) in dry dichloromethane (50 mL). The mixture was stirred at 0-5° C. for 1 h. Dichloromethylmethyl ether (0.61 mL, 6.75 mmol, 1.35 equiv) was added dropwise at 0-5° C. The mixture was then stirred at 0-5° C. for 1 h before it was warmed to room temperature and stirred an additional 1 h. The reaction was quenched with the addition of ice-water (200 mL) and the mixture was stirred at room temperature for 1 h. The mixture was extracted with dichloromethane (3×100 mL). The combined organic layers were washed with saturated brine (200 mL), dried over sodium sulfate, filtered, and concentrated under reduced pressure. The residue was purified on an AnaLogix (25-40 g) column, eluting with a gradient of 0-10% ethyl acetate in heptanes to give the title compound (2.0 g, 92% yield) as a yellow solid.

$^1$H NMR (300 MHz, CDCl$_3$) δ ppm 10.83 (s, 1H), 9.23 (d, 1H), 8.05 (d, 1H), 7.93 (s, 1H), 7.61 (dd, 1H), 7.28 (dd, 1H), 4.36 (m, 1H), 2.24 (m, 2H), 1.86 (m, 2H), 1.53 (m, 2H), 1.21 (m, 3H), 0.89 (s, 9H); LCMS m/z 437.1 [M+1]$^+$.

Step 3: 2-(((trans)-4-(tert-butyl)cyclohexyl)oxy)-4-(trifluoromethyl)-1-naphthaldehyde

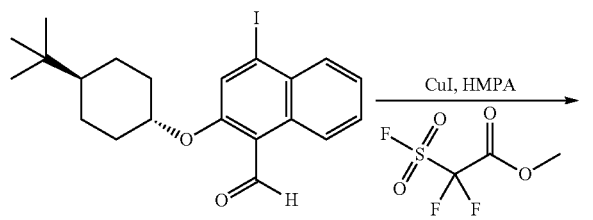

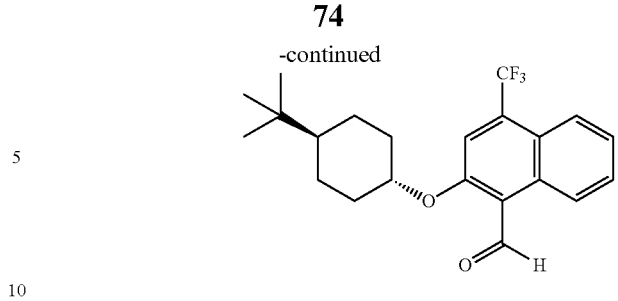

A stream of nitrogen was bubbled through a solution of 2-(((trans)-4-(tert-butyl)cyclohexyl)oxy)-4-iodo-1-naphthaldehyde (1.0 g, 2.29 mmol, 1.0 equiv) and hexamethylphosphoramide (HMPA, 2.0 mL, 11.46 mmol, 5 equiv) in anhydrous DMF (300 mL) for 10 min. Copper (I) iodide (0.74 g, 3.90 mmol, 1.7 equiv) and methyl fluorosulfonyldifluoroacetate (1.46 mL, 11.46 mmol, 5 equiv) were added to the mixture. A stream of nitrogen was bubbled through the reaction for an additional 5 min. The resulting mixture was then stirred at 80° C. for 4 h, at which point LCMS indicated that the reaction was complete. The reaction was cooled to room temperature and the mixture was diluted with water (100 mL). Saturated sodium bicarbonate solution was added until pH was between 9-10. The mixture was extracted with ethyl acetate (3×100 mL). The combined organic layers were washed with saturated brine, dried over sodium sulfate, filtered, and concentrated under reduced pressure. The residue was purified on an AnaLogix (25-40 g) column, eluting with straight heptanes to give the title compound (0.79 g, 90% yield) as a pale-yellow solid.

$^1$H NMR (300 MHz, CDCl$_3$) δ ppm 10.86 (s, 1H), 9.26 (d, 1H), 8.12 (d, 1H), 7.68 (s, 1H), 7.65 (dd, 1H), 7.56 (dd, 1H), 4.41 (m, 1H), 2.23 (m, 2H), 1.92 (m, 2H), 1.55 (m, 2H), 1.21 (m, 3H), 0.89 (s, 9H); LCMS m/z 379.2 [M+1]$^+$.

Step 4: ethyl 1-((2-(((trans)-4-(tert-butyl)cyclohexyl)oxy)-4-(trifluoromethyl)naphthalen-1-yl)methyl)piperidine-4-carboxylate

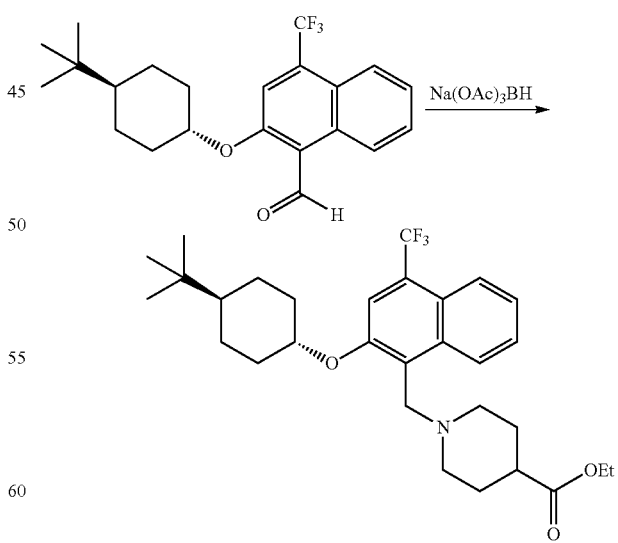

To a solution of 2-(((trans)-4-(tert-butyl)cyclohexyl)oxy)-4-(trifluoromethyl)-1-naphthaldehyde (0.79 g, 2.087 mmol, 1.0 equiv) in anhydrous ethyl acetate (20 mL) was added ethyl isonipecotate (0.32 mL, 2.087 mmol, 1.0 equiv) at room temperature. The mixture was stirred at 40° C. for 4 h. The mixture was cooled to room temperature and sodium triacetoxyborohydride (0.66 g, 3.131 mmol, 1.5 equiv) was added in portions at room temperature. The mixture was stirred at room temperature overnight. The reaction mixture was diluted with ethyl acetate (100 mL), washed with water (50 mL), saturated brine, dried over sodium sulfate, filtered, and concentrated under reduced pressure. The residue was purified on an AnaLogix (25-40 g) column, eluting with a gradient of 0% to 50% ethyl acetate in heptanes to give the title compound (1.0 g, ~80% purity) as a pale-yellow oil. This material contained an unidentified by-product and was used in the next step without further purification.

$^1$H NMR (300 MHz, CDCl$_3$) δ ppm 8.35 (d, 1H), 8.05 (d, 1H), 7.60 (s, 1H), 7.47 (m, 2H), 4.23 (m, 1H), 4.16 (q, 2H), 3.83 (s, 2H), 2.87 (m, 2H), 2.25 (m, 4H), 1.86 (m, 4H), 1.66 (m, 3H), 1.45 (m, 2H), 1.32-1.12 (m, 6H), 0.89 (s, 9H); LCMS m/z 520.2 [M+1]$^+$.

Step 5: 1-((2-(((trans)-4-(tert-butyl)cyclohexyl)oxy)-4-(trifluoromethyl)naphthalen-1-yl)methyl)piperidine-4-carboxylic acid

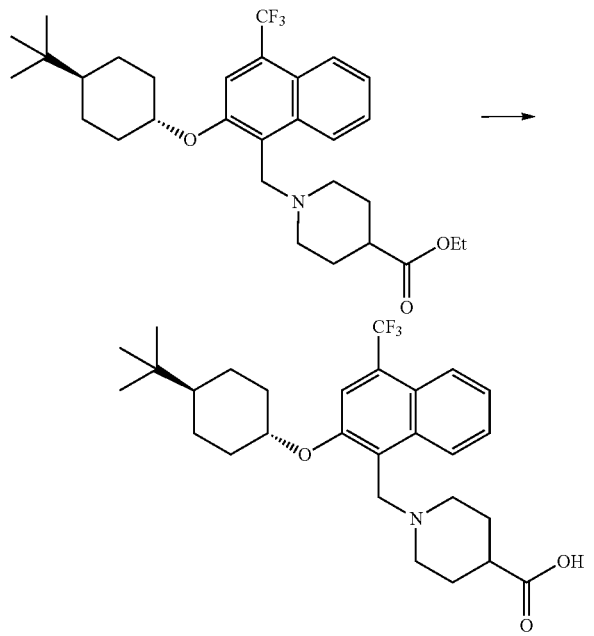

A 1.0 M aqueous NaOH solution (7.7 mL, 7.7 mmol, 4.0 equiv) was added to a solution of ethyl 1-((2-(((trans)-4-(tert-butyl)cyclohexyl)oxy)-4-(trifluoromethyl)naphthalen-1-yl)methyl)piperidine-4-carboxylate (1.0 g, 1.92 mmol, 1.0 equiv) in ethanol (20 mL) at room temperature. The resulting mixture was heated at reflux overnight at which point LCMS indicated that the hydrolysis was not complete. Additional NaOH solution (8 ml, 8 mmol, 4.0 equiv) was added, and the mixture was heated at reflux for 2 h at which point LCMS indicated that the hydrolysis was complete. The reaction was cooled to room temperature and the mixture was concentrated under reduced pressure to remove most of ethanol. The residue was diluted with water (50 mL), acidified with 2 M HCl solution to pH 3-4, and extracted with ethyl acetate (3×50 mL). The combined organic layers were washed with saturated brine, dried over sodium sulfate, filtered, and concentrated under reduced pressure. The residue was purified on an AnaLogix (15-24 g) column, eluting with a gradient of 0-100% ethyl acetate in heptanes to give the title compound (0.55 g, 54% overall yield for two steps) as a white solid.

$^1$H NMR (300 MHz, CDCl$_3$) δ ppm 8.36 (d, 1H), 8.07 (d, 1H), 7.60 (s, 1H), 7.52 (dd, 1H), 7.48 (dd, 1H), 4.31 (s, 2H), 4.26 (m, 1H), 3.21 (m, 2H), 2.34 (m, 2H), 2.16 (m, 3H), 1.89 (m, 4H), 1.74 (m, 2H), 1.46 (m, 2H), 1.11 (m, 3H), 0.89 (s, 9H); $^{19}$F NMR □ ppm −59.57; LCMS m/z 492.3 [M+1]$^+$.

Example 27: 1-((2-(((trans)-4-(tert-butyl)cyclohexyl)oxy)-4-iodonaphthalen-1-yl)methyl)piperidine-4-carboxylic acid Step 1: ethyl 1-((2-(((trans)-4-(tert-butyl)cyclohexyl)oxy)-4-iodonaphthalen-1-yl)methyl)piperidine-4-carboxylate

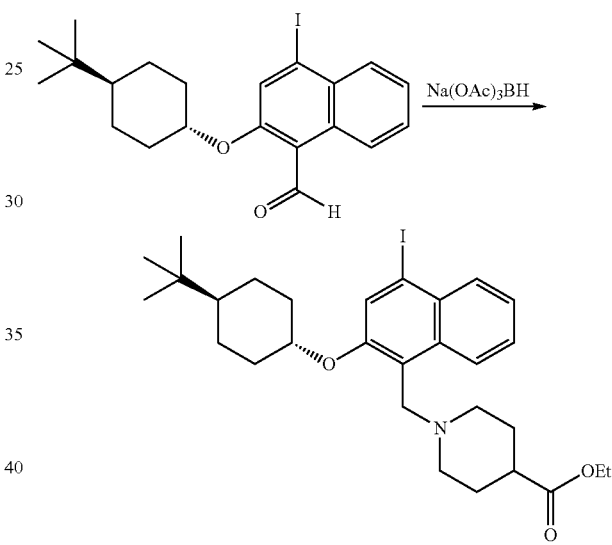

Ethyl isonipecotate (0.71 mL, 4.58 mmol, 1.0 equiv) was added at room temperature to a solution of 2-(((trans)-4-(tert-butyl)cyclohexyl)oxy)-4-iodo-1-naphthaldehyde (2.0 g, 4.58 mmol, 1.0 equiv) in anhydrous ethyl acetate (40 mL). The mixture was stirred at 40° C. for 4 h. The mixture was cooled to room temperature and sodium triacetoxyborohydride (1.46 g, 6.87 mmol, 1.5 equiv) was added in portions. The mixture was stirred at room temperature overnight. The reaction mixture was diluted with ethyl acetate (100 mL), washed with water (50 mL), saturated brine, dried over sodium sulfate, filtered, and concentrated under reduced pressure. The residue was purified on an AnaLogix (25-80 g) column, eluting with a gradient of 0% to 40% ethyl acetate in heptanes to give the title compound (2.1 g, 79% yield) as a pale-yellow oil.

$^1$H NMR (300 MHz, CDCl$_3$) δ ppm 8.09 (d, 1H), 7.98 (d, 1H), 7.82 (s, 1H), 7.41 (m, 2H), 4.18 (m, 1H), 4.16 (q, 2H), 3.83 (s, 2H), 2.85 (m, 2H), 2.18 (m, 4H), 1.84 (m, 4H), 1.66 (m, 3H), 1.42 (m, 2H), 1.32-1.12 (m, 3H), 1.22 (t, 3H), 0.89 (s, 9H); LCMS m/z 578.3 [M+1]$^+$.

Step 2: 1-((2-(((trans)-4-(tert-butyl)cyclohexyl)oxy)-4-iodonaphthalen-1-yl)methyl)piperidine-4-carboxylic acid

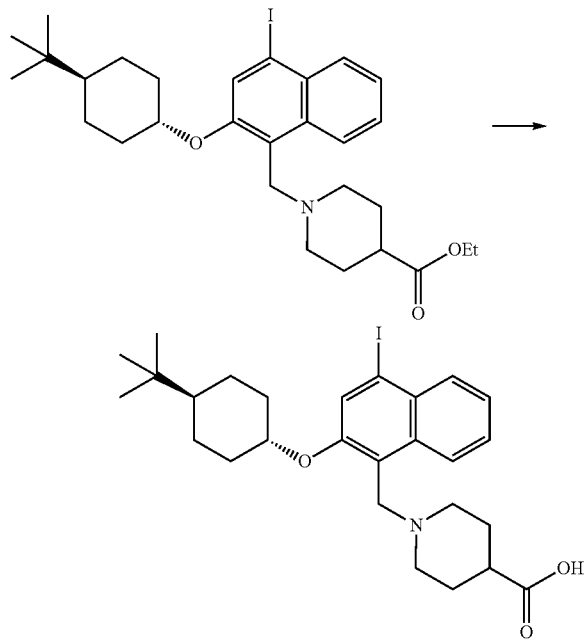

A 3.0 M aqueous NaOH solution was added to a solution of ethyl 1-((2-(((trans)-4-(tert-butyl)cyclohexyl)oxy)-4-iodonaphthalen-1-yl)methyl)piperidine-4-carboxylate (0.18 g, 0.31 mmol, 1.0 equiv) in ethanol (20 mL) at room temperature. The resulting mixture was refluxed until LCMS indicated that the hydrolysis was complete. The reaction was cooled to room temperature and the mixture was concentrated under reduced pressure to remove most of ethanol. The residue was diluted with water (50 mL), acidified with 2 M HCl to pH 3-4 and extracted with ethyl acetate (3×50 mL). The combined organic layers were washed with saturated brine, dried over sodium sulfate, filtered, and concentrated under reduced pressure to give the title compound (0.17 g, 99% yield) as a yellow solid.

$^1$H NMR (300 MHz, CDCl$_3$) δ ppm 8.22 (d, 1H), 8.00 (d, 1H), 7.85 (s, 1H), 7.49 (dd, 1H), 7.41 (dd, 1H), 4.38 (s, 2H), 4.25 (m, 1H), 3.29 (m, 2H), 2.43 (m, 2H), 2.19 (m, 3H), 1.87 (m, 6H), 1.45 (m, 2H), 1.14 (m, 3H), 0.89 (s, 9H); LCMS m/z 550.2 [M+1]$^+$.

Example 28: 1-((2-(((trans)-4-(tert-butyl)cyclohexyl)oxy)-4-chloronaphthalen-1-yl)methyl)piperidine-4-carboxylic acid

Step 1: ethyl 1-((2-(((trans)-4-(tert-butyl)cyclohexyl)oxy)-4-chloronaphthalen-1-yl)methyl)piperidine-4-carboxylate

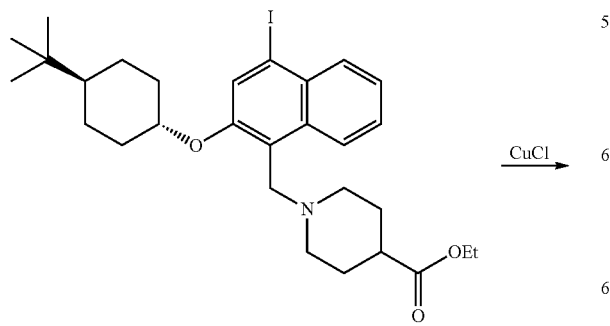

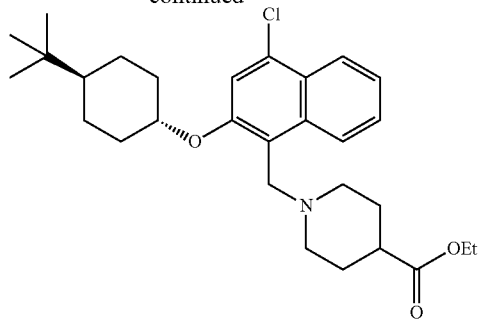

Copper(I) chloride (75 mg, 0.75 mmol, 1.5 equiv) was added at room temperature to a solution of ethyl 1-((2-(((trans)-4-(tert-butyl)cyclohexyl)oxy)-4-iodonaphthalen-1-yl)methyl)piperidine-4-carboxylate (0.29 g, 0.5 mmol, 1.0 equiv) in 2-picoline (10 mL). The mixture was refluxed (128° C.) for one day, at which point LCMS indicated that a mixture of desired product and un-reacted starting material were present. Addition of more CuCl and longer reaction time did not improve the reaction. The reaction mixture was concentrated under reduced pressure and the residue was diluted with THF. The mixture was filtered through celite and the pad was washed with ethyl acetate (50 mL). The filtrate was concentrated under reduced pressure to give a crude mixture (0.30 g) of the title compound and starting material which was not separable by flash chromatography. LCMS m/z 486.1

Step 2: 1-((2-(((trans)-4-(tert-butyl)cyclohexyl)oxy)-4-chloronaphthalen-1-yl)methyl)piperidine-4-carboxylic acid

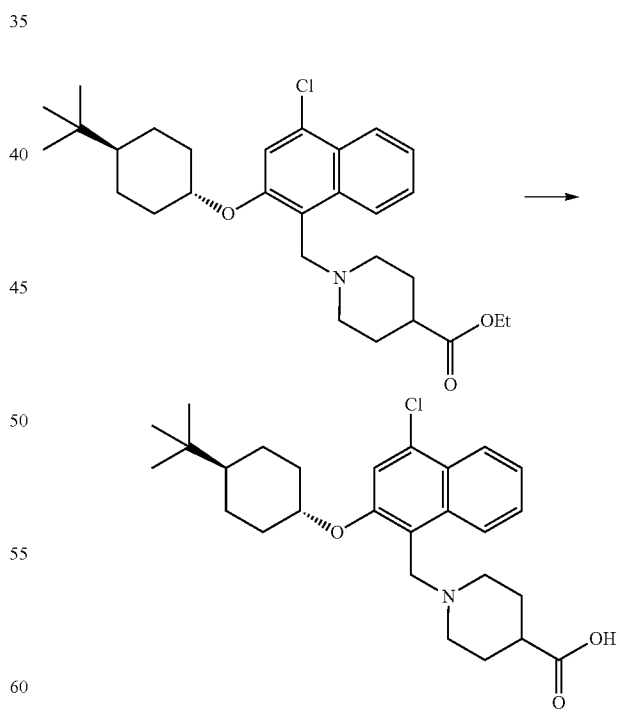

A 3.0 M aqueous NaOH solution (1.7 mL, 5 mmol, 10 equiv) was added at room temperature to a mixture of ethyl 1-((2-(((trans)-4-(tert-butyl)cyclohexyl)oxy)-4-chloronaphthalen-1-yl)methyl)piperidine-4-carboxylate and ethyl 1-((2-(((trans)-4-(tert-butyl)cyclohexyl)oxy)-4-iodonaphthalen-1-yl)methyl)piperidine-4-carboxylate (0.30 g, ~0.5 mmol, 1.0 equiv) in ethanol (20 mL). The resulting mixture was refluxed until LCMS indicated that the hydrolysis was complete. The reaction was cooled to room temperature and concentrated under reduced pressure to remove most of ethanol. The residue was diluted with water (50 mL), acidified with 2 M HCl solution to pH 3-4 and extracted with ethyl acetate (3×50 mL). The combined organic layers were washed with brine, dried over sodium sulfate, filtered, and concentrated under reduced pressure. The residue was purified on an AnaLogix (15-24 g) column, eluting with a gradient of 0-100% ethyl acetate in heptane to give 1 to 1.1 mixture (by NMR), 0.11 g) of the iodo/chloro mixture as a yellow solid (0.11 g). A mixture (~1:1) of 1-((2-(((trans)-4-(tert-butyl)cyclohexyl)oxy)-4-chloronaphthalen-1-yl) methyl)piperidine-4-carboxylic acid (52 mg, 0.11 mmol) and its 4-iodide analog was separated under SFC (using IC (2×15 cm) under 30% methanol (0.1% DEA)/CO2, 100 bar) to give pure 1-[6-(4-tert-Butyl-cyclohexyloxy)-8-chloro-naphthalen-2-ylmethyl]-piperidine-4-carboxylic acid (19 mg; Yield=36%). Lyopholization gave a white powder (19 mg). LCMS Rt=1.67 min, m/z=458.20. ([M]+, 100%).

¹H NMR (400 MHz, METHANOL-d₄) δ 8.19 (td, J=1.81, 8.55 Hz, 2H), 7.57 (ddd, J=1.29, 6.98, 8.49 Hz, 1H), 7.54 (s, 1H), 7.48 (ddd, J=1.04, 6.96, 8.31 Hz, 1H), 4.36 (tt, J=4.27, 10.75 Hz, 1H), 4.14 (s, 2H), 3.11 (d, J=11.92 Hz, 2H), 2.96 (q, J=7.28 Hz, 4H), 2.47 (t, J=11.42 Hz, 2H), 1.41-2.30 (m, 12H), 1.24-1.31 (m, 6H), 1.05-1.23 (m, 2H), 0.91 (s, 9H)

Example 29: (R)-1-((6-(((trans-4-(tert-Butyl)cyclo-hexyl)oxy)-8-methylnaphthalen-2-yl)methyl)pyrrolidine-3-carboxylic acid Step 1: 3-(((trans)-4-(tert-Butyl)cyclohexyl)oxy)-1-methylnaphthalene

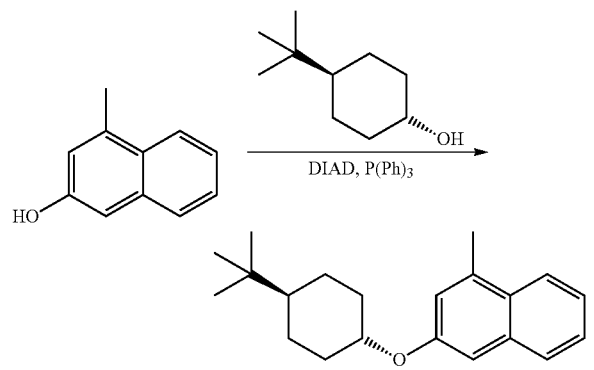

To a stirred solution of 4-methylnaphthalen-2-ol (31.64 g, 200 mmol, 1.0 equiv) and cis-4-tert-butylcyclohexanol (37.50 g, 240 mmol, 1.2 equiv) in dry toluene (600 mL) was added triphenylphosphine (78.69 g, 300 mmol, 1.5 equiv) and diisopropyl azodicarboxylate (59.01 mL, 300 mmol, 1.5 equiv) at room temperature. The resulting mixture was refluxed overnight. The reaction was quenched with water (300 mL) and the layers were separated. The aqueous layer was extracted with ethyl acetate (3×300 mL). The combined organic layers were washed with brine, dried over sodium sulfate, and concentrated under reduced pressure. The residue was purified on a Biogen-75 column, eluting with heptanes to give the title compound (50 g, contained some impurities) as a brown oil. This material was treated with cold heptanes to give the title compound (24.0 g) as an off-white solid. The mother liquor was purified on an AnaLogix (65-400 g) column, eluting with a gradient of 0-10% ethyl acetate in heptanes to give more title compound (7.3 g) as an off-white solid. In addition some mixed fractions were also obtained.

¹H NMR (300 MHz, CDCl₃) δ ppm 7.88 (d, 1H), 7.69 (d, 1H), 7.44 (m, 1H), 7.38 (m, 1H), 7.01 (m, 2H), 4.26 (m, 1H), 2.64 (s, 3H), 2.29 (m, 2H), 1.90 (m, 2H), 1.45-1.36 (m, 2H), 1.28-1.09 (m, 3H), 0.90 (s, 9H); LCMS m/z 297.3 [M+1]⁺.

Step 2: 2-(((trans)-4-(tert-butyl)cyclohexyl)oxy)-4-methyl-1-naphthaldehyde

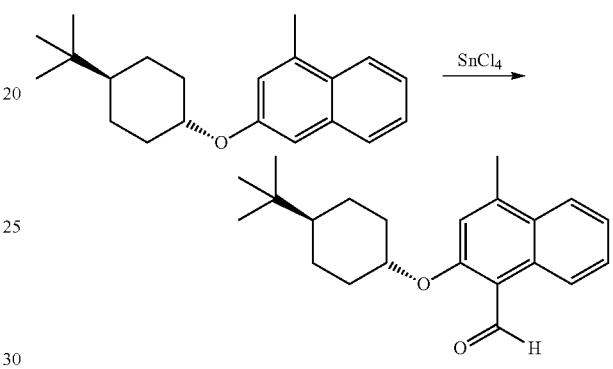

To a solution of 3-(((trans)-4-(tert-butyl)cyclohexyl)oxy)-1-methylnaphthalene (37.8 g, 127.5 mmol, 1.0 equiv) in dry dichloromethane (1000 mL) was added SnCl₄ (20.15 mL, 172.1 mmol, 1.35 equiv) dropwise at 0-5° C. and the mixture was stirred at 0-5° C. for 1 h. Dichloromethylmethyl ether (15.57 mL, 172.1 mmol, 1.35 equiv) was added dropwise at 0-5° C., and the mixture was stirred at 0-5° C. for 1 h before warming to room temperature and stirring for an additional 1 h. The reaction was quenched by the addition of ice-water (200 mL) and the mixture was stirred at room temperature for 1 h. The mixture was extracted with dichloromethane (3×200 mL). The combined organic layers were washed with saturated brine (200 mL), dried over sodium sulfate, filtered, and concentrated under reduced pressure. The residue was purified on an AnaLogix (65-400 g) column, eluting with a gradient of 0-20% ethyl acetate in heptanes to give the title compound (35.0 g) as a yellow solid. This material was further purified by a trituration with 10% ethyl acetate in heptanes to give the title compound (31.0 g, 75% yield) as an off-white solid.

¹H NMR (300 MHz, CDCl₃) δ ppm 10.82 (s, 1H), 9.35 (d, 1H), 7.93 (d, 1H), 7.60 (m, 1H), 7.45 (m, 1H), 7.15 (s, 1H), 4.37 (m, 1H), 2.74 (s, 3H), 2.23 (m, 2H), 1.88 (m, 2H), 1.49 (m, 2H), 1.12 (m, 3H), 0.90 (s, 9H); LCMS m/z 325.2 [M+1]⁺.

Step 3: (R)-3-Benzyl 1-tert-butyl pyrrolidine-1,3-dicarboxylate

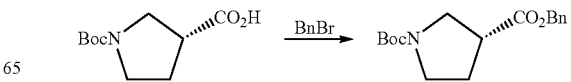

DBU (16.25 mL, 108.71 mmol, 1.5 equiv) and benzyl bromide (9.48 mL, 79.72 mmol, 1.1 equiv) were added to a solution of (R)-1-(tert-butoxycarbonyl)pyrrolidine-3-carboxylic acid (15.6 g, 72.47 mmol, 1.0 equiv) in dry toluene (300 mL) at room temperature. The resulting mixture was stirred at room temperature overnight. The reaction was quenched with water (200 mL) and the layers were separated. The aqueous layer was extracted with ethyl acetate (3×200 mL). The combined organic layers were washed with saturated brine (200 mL), dried over sodium sulfate, filtered, and concentrated under reduced pressure. The residue was purified on an AnaLogix (65-600 g) column, eluting with a gradient of 0-50% ethyl acetate in heptanes to give the title compound (19.2 g, 87% yield) as a colorless oil.

$^1$H NMR (300 MHz, CDCl$_3$) δ ppm 7.17 (m, 5H), 5.16 (s, 2H), 3.57 (m, 3H), 3.35 (m, 1H), 3.08 (m, 1H), 2.15 (m, 2H), 1.46 (s, 9H); LCMS m/z 328.2 [M+Na]$^+$.

Step 4: (R)-Benzyl pyrrolidine-3-carboxylate trifluoroacetic acid salt

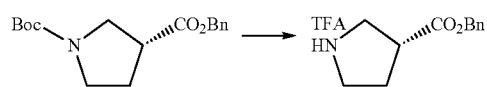

Trifluoroacetic acid (60 mL) was added to a solution of ((R)-3-benzyl 1-tert-butyl pyrrolidine-1,3-dicarboxylate (19.2 g, 62.87 mmol, 1.0 equiv) in dichloromethane (600 mL) at room temperature. The resulting mixture was stirred at room temperature for 4 h. The reaction mixture was concentrated under reduced pressure to give the title compound (33.37 g, >100% yield with extra TFA remaining) as a colorless oil.

$^1$H NMR (300 MHz, CDCl$_3$) δ ppm 11.39 (s, 2H), 8.70 (br s, 1H), 8.18 (br s, 1H), 7.17 (m, 5H), 5.16 (s, 2H), 3.75-3.30 (m, 3H), 2.41-2.22 (m, 2H); LCMS m/z 206.1 [M+1]$^+$.

Step 5: (R)-benzyl 1-((2-(((trans)-4-(tert-butyl)cyclohexyl)oxy)-4-methylnaphthalen-1-yl)methyl)pyrrolidine-3-carboxylate

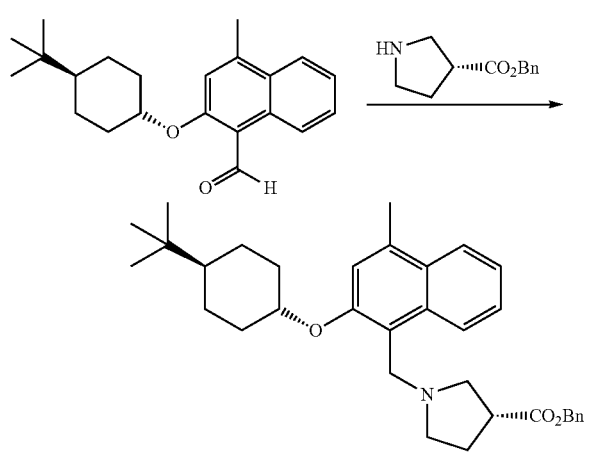

Diisopropylethylamine was added to a solution of (R)-benzyl pyrrolidine-3-carboxylate trifluoroacetic acid salt (33.37 g, ~62.87 mmol, 1.0 equiv) in anhydrous ethyl acetate (600 mL). The mixture was stirred at room temperature for 1 h. The mixture was washed with water (100 mL), and the aqueous layer was extracted with ethyl acetate (2×100 mL). The combined organic layers were washed with saturated brine, dried over sodium sulfate, filtered, and concentrated under reduced pressure to give the free amine of compound.

To a solution of 2-(((trans)-4-(tert-butyl)cyclohexyl)oxy)-4-methyl-1-naphthaldehyde (15.30 g, 47.16 mmol, 0.75 equiv) was added a solution of the above compound in anhydrous ethyl acetate (100 mL) at room temperature. The resulting mixture was stirred at 40° C. for 4 h. After the mixture was cooled to room temperature, sodium triacetoxyborohydride (19.99 g, 94.31 mmol, 1.5 equiv) was added and the resulting mixture was stirred at 40° C. overnight. The reaction was quenched with water (100 mL), and the layers were separated. The aqueous layer was extracted with ethyl acetate (2×200 mL). The combined organic layers were washed with saturated brine, dried over sodium sulfate, and concentrated under reduced pressure. The residue was purified on an AnaLogix (65-600 g) column, eluting with a gradient of 10 to 100% ethyl acetate in heptanes to give the title compound (23.8 g, 74% yield) as a pale-yellow oil.

$^1$H NMR (300 MHz, CDCl$_3$) δ ppm 8.08 (d, 1H), 7.95 (d, 1H), 7.55 (m, 1H), 7.41 (m, 1H), 7.34-7.22 (m, 5H), 7.09 (s, 1H), 5.17 (s, 2H), 4.55 (s, 2H), 4.27 (m, 1H), 3.55 (m, 1H), 3.22 (m, 2H), 2.95 (m, 1H), 2.68 (s, 3H), 2.15 (m, 4H), 1.83 (m, 2H), 1.43 (m, 2H), 1.10 (m, 2H), 0.89 (s, 9H); LCMS m/z 514.2 [M+1]$^+$.

Step 6: (R)-1-((6-((trans-4-(tert-Butyl)cyclohexyl)oxy)-8-methylnaphthalen-2-yl)methyl)pyrrolidine-3-carboxylic acid

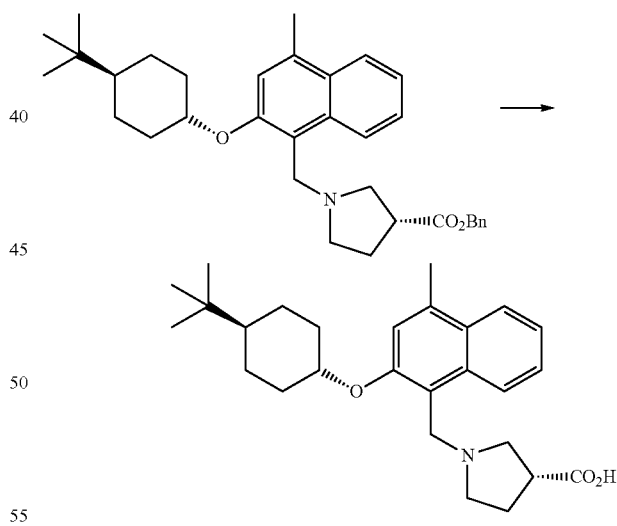

A mixture of (R)-benzyl 1-((6-(((1r,4R)-4-(tert-butyl)cyclohexyl)oxy)-8-methylnaphthalen-2-yl)methyl)pyrrolidine-3-carboxylate (23.8 g, 46.33 mmol) and 10% Pd/C (~50% wet, 2.5 g) in MeOH (1000 mL) was hydrogenated at room temperature @ 45 psi overnight. The mixture was filtered through celite, and the filtrate was concentrated under reduced pressure. The residue was purified on an AnaLogix (65-200 g) column, eluting with a gradient of 0-10% methanol in dichloromethane to give the title compound (6.5 g) as a white solid. [α]$_D$=−11.5 (0.511 g/100 mL CHCl$_3$);

¹H NMR (300 MHz, CDCl₃) δ ppm 7.97 (d, 1H), 7.93 (d, 1H), 7.53 (m, 1H), 7.39 (m, 1H), 7.12 (s, 1H), 4.78 (s, 2H), 4.34 (m, 1H), 3.24 (m, 5H), 2.70 (s, 3H), 2.26-2.18 (m, 4H), 1.87 (m, 2H), 1.48-1.44 (m, 2H), 1.22-1.08 (m, 3H), 0.88 (s, 9H); LCMS m/z 424.2 [M+1]⁺.

Example 30: (S)-1-((2-(((trans)-4-(tert-butyl)cyclohexyl)oxy)-4-methylnaphthalen-1-yl)methyl)pyrrolidine-3-carboxylic acid Step 1: (S)-3-Benzyl 1-tert-butyl pyrrolidine-1,3-dicarboxylate

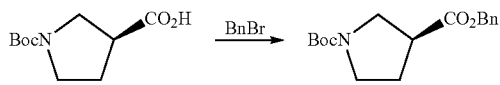 [SMILES: CC(C)(C)OC(=O)N1CC[C@H](C(=O)O)C1 ; "BnBr" ; CC(C)(C)OC(=O)N1CC[C@H](C(=O)OCc2ccccc2)C1]

DBU (15.63 mL, 104.53 mmol, 1.5 equiv) and benzyl bromide (9.12 mL, 76.66 mmol, 1.1 equiv) was added to a solution of (S)-1-(tert-butoxycarbonyl)pyrrolidine-3-carboxylic acid (15.0 g, 69.69 mmol, 1.0 equiv) in dry toluene (300 mL) at room temperature The resulting mixture was stirred at room temperature overnight. The reaction was quenched with water (200 mL, and the layers were separated. The aqueous layer was extracted with ethyl acetate (3×200 mL). The combined organic layers were washed with brine (200 mL), dried over sodium sulfate, filtered, and concentrated under reduced pressure. The residue was purified on an AnaLogix (65-400 g) column, eluting with a gradient of 0-50% ethyl acetate in heptanes to give the title compound (18.72 g, 88% yield) as a colorless oil.

¹H NMR (300 MHz, CDCl₃) δ ppm 7.17 (m, 5H), 5.16 (s, 2H), 3.57 (m, 3H), 3.35 (m, 1H), 3.08 (m, 1H), 2.15 (m, 2H), 1.46 (s, 9H); LCMS m/z 328.2 [M+Na]⁺.

Step 2: (S)-Benzyl pyrrolidine-3-carboxylate trifluoroacetic acid salt

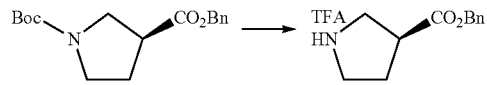 [SMILES: CC(C)(C)OC(=O)N1CC[C@H](C(=O)OCc2ccccc2)C1 ; O=C(OCc1ccccc1)[C@H]1CCNC1]

Trifluoroacetic acid (60 mL) was added to a solution of ((S)-3-benzyl 1-tert-butyl pyrrolidine-1,3-dicarboxylate (18.72 g, 61.30 mmol, 1.0 equiv) in dichloromethane (600 mL) at room temperature. The resulting mixture was stirred at room temperature for 4 h. The reaction mixture was concentrated under reduced pressure to give the title compound (34.4 g, >100% yield with extra TFA remaining) as a colorless oil.

¹H NMR (300 MHz, CDCl₃) δ ppm 11.39 (s, 2H), 8.70 (br s, 1H), 8.18 (br s, 1H), 7.17 (m, 5H), 5.16 (s, 2H), 3.75-3.30 (m, 3H), 2.41-2.22 (m, 2H); LCMS m/z 206.1 [M+1]⁺.

Step 3: (S)-benzyl 1-((2-(((trans)-4-(tert-butyl)cyclohexyl)oxy)-4-methylnaphthalen-1-yl)methyl)pyrrolidine-3-carboxylate

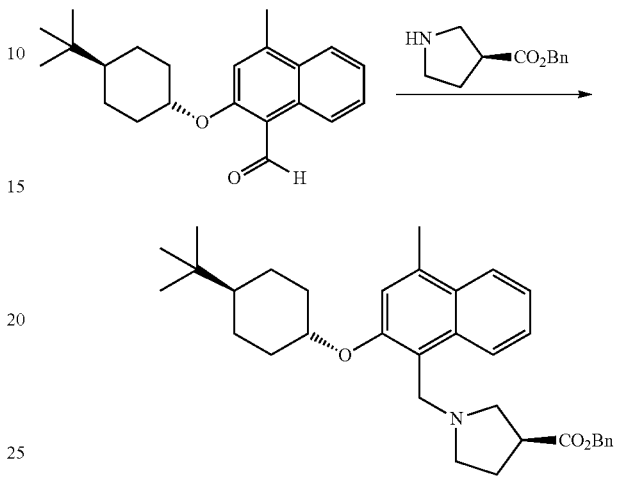

Diisopropylethylamine (49.7 mL, 285.1 mmol, 1.5 equiv) was added to a solution of (S)-benzyl pyrrolidine-3-carboxylate trifluoroacetic acid salt (32.0 g, ~57.0 mmol, 1.0 equiv) in anhydrous ethyl acetate (600 mL) at room temperature. The mixture was stirred at room temperature for 1 h. The mixture was washed with water (100 mL), and the aqueous layer was extracted with ethyl acetate (2×100 mL). The combined organic layers were washed with saturated brine, dried over sodium sulfate, filtered, and concentrated under reduced pressure to give the free amine of compound.

To a solution of 2-(((trans)-4-(tert-butyl)cyclohexyl)oxy)-4-methyl-1-naphthaldehyde (14.0 g, 43.15 mmol, 0.75 equiv) was added a solution of the above free amine in anhydrous ethyl acetate (100 mL) at room temperature. The resulting mixture was stirred at 40° C. for 4 h. After the mixture was cooled to room temperature, sodium triacetoxyborohydride (18.12 g, 85.5 mmol, 1.5 equiv) was added and the resulting mixture was stirred at 40° C. overnight. The reaction was quenched with water (100 mL), and the layers were separated. The aqueous layer was extracted with ethyl acetate (2×200 mL). The combined organic layers were washed with saturated brine, dried over sodium sulfate, and concentrated under reduced pressure. The residue was purified on an AnaLogix (65-600 g) column, eluting with a gradient of 10% 100% ethyl acetate in heptanes to give the title compound (23.7 g, 81% yield) as a pale-yellow oil.

¹H NMR (300 MHz, CDCl₃) δ ppm 8.08 (d, 1H), 7.95 (d, 1H), 7.55 (m, 1H), 7.41 (m, 1H), 7.34-7.22 (m, 5H), 7.09 (s, 1H), 5.17 (s, 2H), 4.55 (s, 2H), 4.27 (m, 1H), 3.55 (m, 1H), 3.22 (m, 2H), 2.95 (m, 1H), 2.68 (s, 3H), 2.15 (m, 4H), 1.83 (m, 2H), 1.43 (m, 2H), 1.10 (m, 2H), 0.89 (s, 9H); LCMS m/z 514.2 [M+1]⁺.

Step 4: (S)-1-((2-(((trans)-4-(tert-butyl)cyclohexyl)oxy)-4-methylnaphthalen-1-yl)methyl)pyrrolidine-3-carboxylic acid

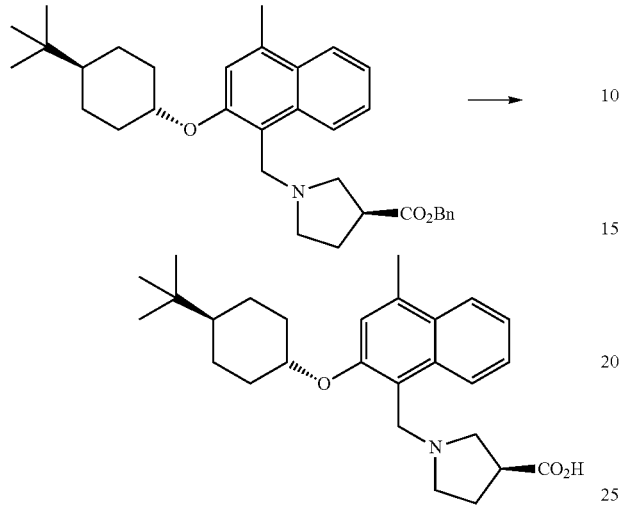

A mixture of (S)-benzyl 1-((6-(((1r,4S)-4-(tert-butyl)cyclohexyl)oxy)-8-methylnaphthalen-2-yl)methyl)pyrrolidine-3-carboxylate (25.6 g, 49.83 mmol) and 10% Pd/C (~50% wet, 2.5 g) in MeOH (1000 mL) was hydrogenated at room temperature @ 45 psi overnight. The mixture was filtered through celite and the filtrate was concentrated under reduced pressure. The residue was purified on an AnaLogix (65-200 g) column, eluting with a gradient of 0-10% methanol in dichloromethane to give the title compound (9.0 g) as a white solid. $[\alpha]_D$=+11.4 (0.494 g/100 mL CHCl$_3$);

$^1$H NMR (300 MHz, CDCl$_3$) δ ppm 7.98 (d, 1H), 7.91 (d, 1H), 7.51 (m, 1H), 7.37 (m, 1H), 7.11 (s, 1H), 4.76 (s, 2H), 4.34 (m, 1H), 3.68-3.21 (m, 5H), 2.70 (s, 3H), 2.26-2.17 (m, 4H), 1.87 (m, 2H), 1.48-1.40 (m, 2H), 1.21-1.07 (m, 3H), 0.87 (s, 9H); LCMS m/z 424.2 [M+1]$^+$.

Example 31: 1-((2-(((trans)-4-(tert-butyl)cyclohexyl)oxy)-4-methylnaphthalen-1-yl)methyl)piperidine-4-carboxylic acid Step 1: 2-((trans-4-(tert-butyl)cyclohexyl)oxy)-4-methyl-1-naphthaldehyde

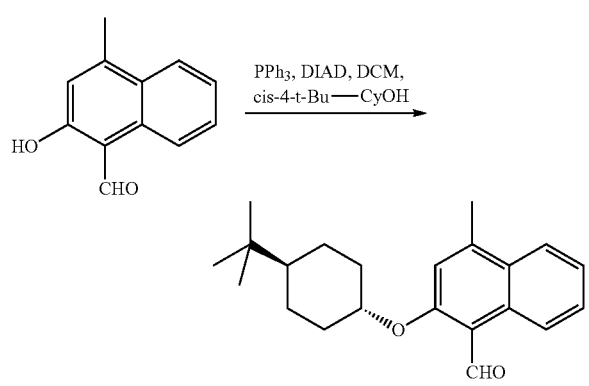

To a mixture of 2-hydroxy-4-methyl-1-naphthaldehyde (0.311 g, 1.67 mmol), cis-4-tert-butyl-cyclohexanol (0.2876 g, 1.840 mmol) and triphenylphosphine (0.8761 g, 3.340 mmol) in methylene chloride (4 mL, 60 mmol) was stirred for 20 min, then, diisopropyl azodicarboxylate (0.42 mL, 2.0 mmol) was added dropwise at 0° C. The mixture became clear. The solution was stirred at rt overnight. The reaction was added silica gel and the solvent was concentrated. The residue was purified with silica gel eluted with EtOAc in hexanes from 0 to 20% to give 2.0 g of white precipitates. TLC showed the compound contained PPh$_3$. The mixture was dissolved with CH$_2$Cl$_2$ and silica gel was added and concentrated. The crude was columned again eluted with 100% hexane to remove PPh$_3$ then, increase the EtOAc from 0 to 30% to give the titled product as an oil (335 mg, 62%). LCMS showed a M+H peak at m/z=325.00, Rt=2.20 min.

Step 2: ethyl 1-((2-(((trans)-4-(tert-butyl)cyclohexyl)oxy)-4-methylnaphthalen-1-yl)methyl)piperidine-4-carboxylate

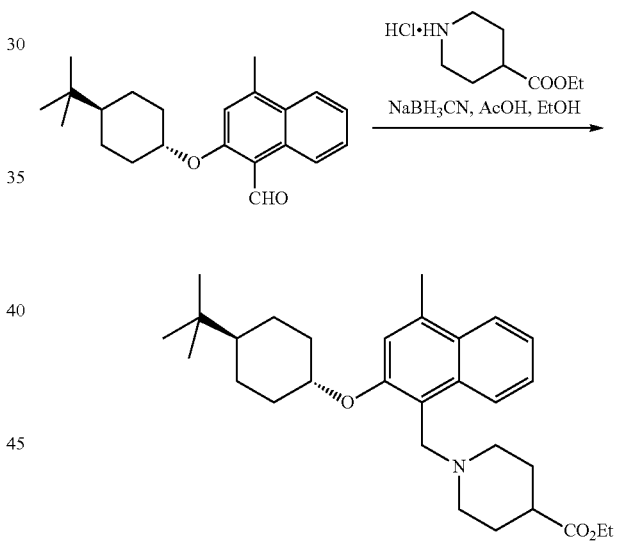

To a solution of 2-(((trans)-4-(tert-butyl)cyclohexyl)oxy)-4-methyl-1-naphthaldehyde (173.6 mg, 0.5350 mmol) and piperidine-4-carboxylic acid ethyl ester (HCl salt, 104 mg, 0.535 mmol) in ethanol (1 mL, 20 mmol) was heated to reflux for 2 h. The yellow solution was cooled to room temperature and sodium cyanoborohydride (40.3 mg, 0.642 mmol) was added and was heated to reflux for overnight. After cooled down to room temperature, and concentrated down. The solid was suspended in water and EtOAc, The organic layer was washed with brine and dry and concentrated. The crude was columned in Si gel with MeOH/DCM yields a solid as the product (48 mg, 19%). LCMS Rt=1.76 min, m/z=466.30 [M+1].

Step 3: 1-((2-(((trans)-4-(tert-butyl)cyclohexyl)oxy)-4-methylnaphthalen-1-yl)methyl)piperidine-4-carboxylic acid

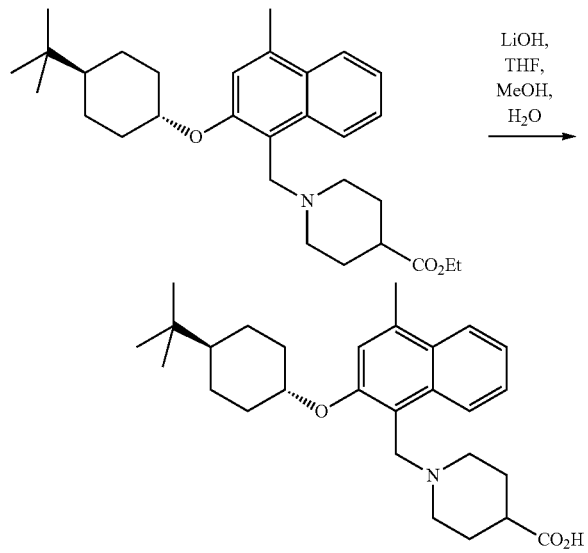

Lithium hydroxide monohydride (0.04543 g, 1.083 mmol) was added to a solution of the ethyl 1-((2-(((trans)-4-(tert-butyl)cyclohexyl)oxy)-4-methylnaphthalen-1-yl)methyl)piperidine-4-carboxylate (48 mg, 0.10 mmol) in tetrahydrofuran (1 mL, 20 mmol), methanol (0.71 mL, 18 mmol) and water (0.5 mL, 30 mmol). The mixture was stirred at rt for 1 h. 1 ml 1M HCl was added and the solvent was concentrated. The residue was taken up in MeOH and after filtration, purification with prep HPLC give the titled product as a white solid (12 mg, 27%). LCMS Rt=1.31 min, m/z=438.10 [M+1].

$^1$H NMR (400 MHz, CD$_3$OD) δ=8.10-8.05 (m, 1H), 8.03 (d, J=8.8 Hz, 1H), 7.64 (ddd, J=1.2, 7.0, 8.3 Hz, 1H), 7.53-7.46 (m, 1H), 7.40 (s, 1H), 4.76 (s, 2H), 4.61-4.49 (m, 1H), 3.65 (d, J=12.5 Hz, 2H), 3.44-3.37 (m, 2H), 2.78-2.73 (m, 3H), 2.32-2.12 (m, 2H), 2.02-1.75 (m, 3H), 1.64-1.03 (m, 9H), 0.92 (s, 9H).

Example 32: 1-((2-((trans-4-(tert-butyl)cyclohexyl)oxy)naphthalen-1-yl)methyl)piperidine-4-carboxylic acid

Step 1: 2-(benzyloxy)-1-naphthaldehyde

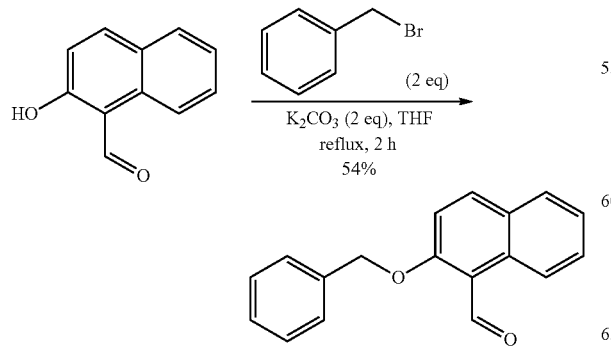

The preparation of 2-(benzyloxy)-1-naphthaldehyde was similar to 2-(cis-4-tert-butylcyclohexyloxy)-4-methyl-1-naphthaldehyde. 500 mg, a brown solid, yield: 54%. ESI-MS (M+H)+: 263.1.

$^1$H NMR (400 MHz, CDCl$_3$) δ: 10.98 (s, 1H), 9.28 (d, J=8.4 Hz, 1H), 8.03 (d, J=8.8 Hz, 1H), 7.77 (d, J=8.0 Hz, 1H), 7.64-7.60 (m, 1H), 7.47-7.33 (m, 7H), 5.34 (s, 2H).

Step 2: ethyl 1-((2-(benzyloxy)naphthalen-1-yl)methyl)piperidine-4-carboxylate

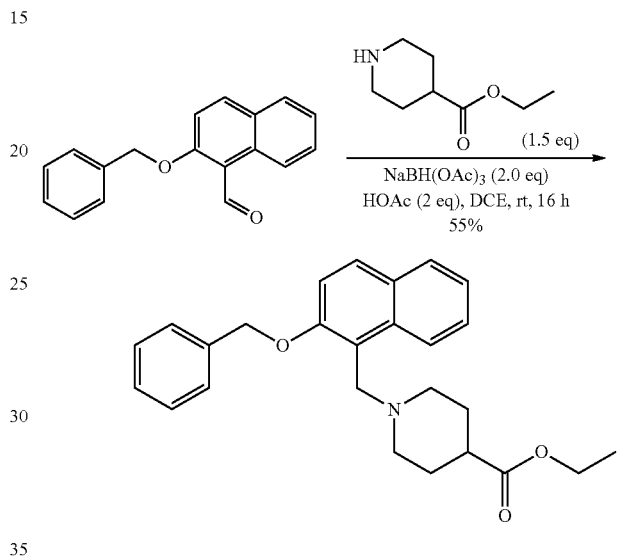

The preparation of ethyl 1-((2-(benzyloxy)naphthalen-1-yl)methyl)piperidine-4-carboxylate was similar to that of ethyl 1-((2-(((trans)-4-(tert-butyl)cyclohexyl)oxy)-4-methylnaphthalen-1-yl)methyl)piperidine-4-carboxylate. 300 mg, a yellow solid, yield: 55%. ESI-MS (M+H)+: 404.2.

$^1$H NMR (400 MHz, CDCl$_3$) δ 8.12 (t, J=8.8 Hz, 1H), 7.95 (t, J=8.8 Hz, 1H), 7.81 (dd, J=7.6, 2.0 Hz, 1H), 7.61-7.57 (m, 1H), 7.44-7.34 (m, 7H), 5.26 (s, 2H), 4.79 (s, 1H), 4.73 (s, 1H), 4.13-4.06 (m, 2H), 3.70-3.67 (m, 1H), 3.50-3.47 (m, 1H), 2.99-2.95 (m, 1H), 2.65-2.60 (m, 1H), 2.27-2.20 (m, 1H), 2.10-2.00 (m, 4H), 1.17 (t, J=7.2 Hz, 3H).

Step 3: ethyl 1-((2-hydroxynaphthalen-1-yl)methyl)piperidine-4-carboxylate

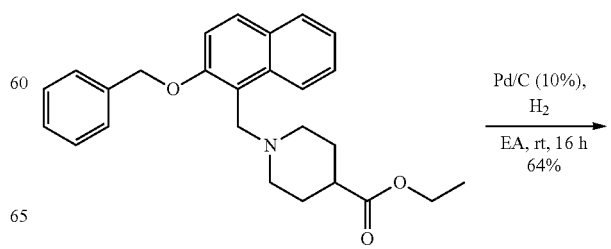

-continued

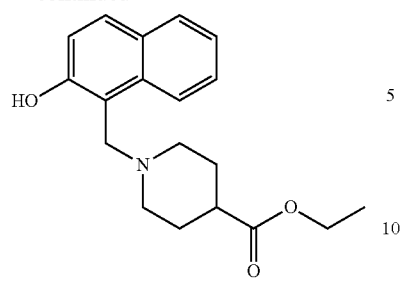

To a solution of ethyl 1-((2-(benzyloxy)naphthalen-1-yl)methyl)piperidine-4-carboxylate (300 mg, 0.74 mmol, 1 eq) in EA (15 mL) was added Pd/C (30 mg, 10% wt). Then the reaction mixture was stirred at room temperature for 16 h under $H_2$. The mixture was filtrated and the filtrate was concentrated to give the titled product as yellow oil (150 mg, yield: 64%). ESI-MS (M+H)+: 314.2.

Step 4: 1-((2-((trans-4-(tert-butyl)cyclohexyl)oxy)naphthalen-1-yl)methyl)piperidine-4-carboxylic acid

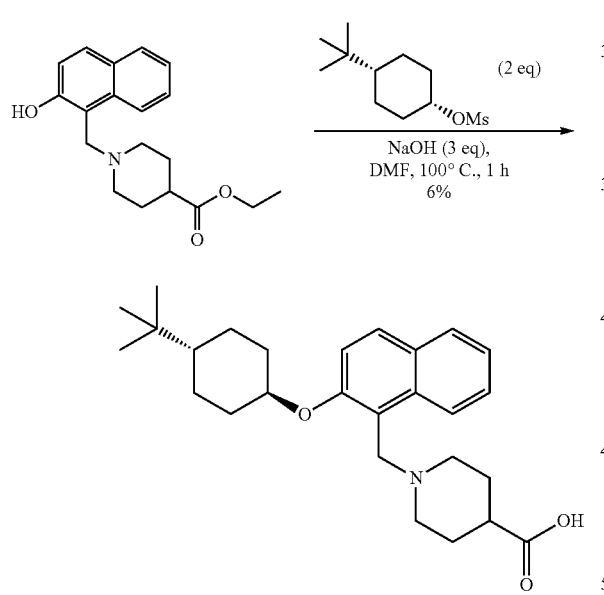

The preparation of 1-((2-(((trans-4-(tert-butyl)cyclohexyl)oxy)naphthalen-1-yl)methyl)piperidine-4-carboxylic acid was similar to that of 2-(cis-4-tert-Butylcyclohexyloxy)-4-methyl-1-naphthaldehyde. 18 mg, a yellow solid, yield: 6%. ESI-MS (M+H)+: 424.3, HPLC: 100%.

$^1$H NMR (400 MHz, $CD_3OD$) δ 8.05 (d, J=9.2 Hz, 2H), 7.90 (d, J=8.0 Hz, 1H), 7.63 (t, J=7.6 Hz, 1H), 7.52 (d, J=9.2 Hz, 1H), 7.45 (t, J=7.6 Hz, 1H), 4.80 (s, 2H), 4.57-4.51 (m, 1H), 3.65-3.58 (m, 2H), 3.30-3.24 (m, 2H), 2.72-2.65 (m, 1H), 2.30-2.18 (m, 4H), 1.95-1.82 (m, 4H), 1.60-1.51 (m, 2H), 1.33-1.23 (m, 2H), 1.19-1.15 (m, 1H), 0.87 (s, 9H).

Example 33: 3-(((2-(hexyloxy)-4-methylnaphthalen-1-yl)methyl)amino)propanoic acid Preparation of the title compound was done utilizing a similar sequence to that of 2-(((2-(((trans)-4-(tert-butyl)cyclohexyl)oxy)-4-methylnaphthalen-1-yl)methyl)amino)acetic acid to give 60 mg of product. Prep. HPLC purification gave 49 mg of white solid (57% yield). LCMS: RT=1.33 min, M+H 344.20.

Example 34: 3-(((4-methyl-2-(octyloxy)naphthalen-1-yl)methyl)amino)propanoic acid Preparation of the title compound was done utilizing a similar sequence to that of 2-(((2-(((trans)-4-(tert-butyl)cyclohexyl)oxy)-4-methylnaphthalen-1-yl)methyl)amino)acetic acid to give 14 mg white precipitate product (30%). LCMS: RT=1.53 min, M+H 372.30.

Example 35: S1P Receptor Activity Assays

Compounds that are not specific for a particular SIP receptor can cause undesirable side effects. Accordingly, compounds are tested to identify those that are specific. Accordingly, the test compounds are tested in a calcium mobilization assay/S1P receptor activity assay. The procedure is essentially as described in Davis et al. (2005) *Journal of Biological Chemistry*, vol. 280, pp. 9833-9841, which is incorporated by reference in its entirety with the following modifications. Calcium mobilization assays are performed in recombinant CHEM cells expressing human $S1P_1$, $S1P_2$, $S1P_3$, $S1P_4$, or $S1P_5$ purchased from Millipore (Billerica, Mass.). To detect free intracellular calcium, $S1P_1$, $S1P_2$, $S1P_3$, $S1P_4$, or $S1P_5$ cells are loaded with FLIPR Calcium 4 dye from Molecular Devices (Sunnyvale, Calif.). Cells are imaged for calcium mobilization using a FLIPR$^{TETRA}$ equipped with a 96-well dispense head.

Agonist percentage activation determinations were obtained by assaying sample compounds and referencing the $E_{max}$ control for each receptor profiled. Antagonist percentage inhibition determinations were obtained by assaying sample compounds and referencing the control $EC_{80}$ wells for each receptor profiled.

Calcium Flux Assay: Agonist Assay Format

Sample compounds were plated in an eight-point, four-fold dilution series in duplicate with a top concentration of 10 µM. The concentrations described here reflect the final concentration of the compounds during the antagonist assay. During the agonist assay the compound concentrations were 1.25 fold higher to allow for the final desired concentration to be achieved with further dilution by $EC_{80}$ of reference agonists during the antagonist assay.

Reference agonists were handled as mentioned above serving as assay control. The reference agonists were handled as described above for $E_{max}$.

Assay was read for 180 seconds using the FLIPR$^{TETRA}$ (This assay run added sample compounds and reference agonist to respective wells). At the completion of the first "Single Addition" assay run, assay plate was removed from the FLIPR$^{TETRA}$ and placed at 25° C. for seven (7) minutes.

Calcium Flux Assay: Antagonist Assay Format

Using the $EC_{80}$ values determined during the agonist assay, stimulated all pre-incubated sample compound and reference antagonist (if applicable) wells with $EC_{80}$ of reference agonist. Read for 180 seconds using the FLIPR$^{TETRA}$ (This assay added reference agonist to respective wells—then fluorescence measurements were collected to calculate percentage inhibition values).

With regard to S1P5 antagonist activity, the compounds of examples 9, 18, 19, 20, 25, and 31 had $IC_{50}$ values of no greater than 100 nm.

With regard to S1P5 antagonist activity, the compounds of examples 10, 29, and 30 had $IC_{50}$ values of no greater than 500 nm.

OPC Differentiation Assay

Enriched populations of oligodendrocytes were grown from post-natal day 2 (P2) female Sprague Dawley rats. The forebrain was dissected out and placed in Hank's buffered saline solution (HBSS; Invitrogen, Grand Island, N.Y.). The tissue was cut into 1 mm fragments and incubated at 37° C. for 15 minutes in 0.01% trypsin and 10 µg/mL DNase. Dissociated cells were plated on poly-L-lysine-coated T75 tissue culture flasks and grown at 37° C. for 10 days in Dulbecco's modified Eagle's medium (DMEM) with 20% fetal calf serum (Invitrogen). A2B5$^+$ OPCs were collected by shaking the flask overnight at 200 rpm and 37° C., resulting in a 95% pure population.

For the differentiation assay, 2 µM and 20 µM antagonist or the same concentrations of vehicle (DMSO) were applied to OPCs cultured in CNTF/T3 containing media. After a 3-day incubation, cells were lysed in 80 µL lysis buffer (50 mM HEPES [4-(2-hydroxyethyl)-1-piperazineethanesulfonic acid], pH 7.5, 150 mM NaCl, 1.5 mM $MgCl_2$, 1 mM ethylene glycol tetraacetic acid [EGTA], 1% Triton X-100 and 10% glycerol) for 30 minutes at 4° C. After centrifugation at 14,000 g for 15 minutes, the supernatants were boiled in Laemmli sample buffer, subjected to 4-20% SDS-PAGE, and analyzed by Western blotting with anti-MBP, anti-myelin-associated glycoprotein (MAG), or anti-beta actin antibodies. The secondary antibodies used were anti-mouse IgG-HRP (horseradish peroxidase) and anti-rabbit IgG-HRP respectively.

DRG-OPC Myelination Assay

Embryonic neocortical neurons are dissected from embryonic day 18 (E18) Sprague Dawley rats, and then plated on poly-D-lysine (100 µg/mL)-coated cover slips and grown in neurobasal medium supplemented with B27 (Invitrogen) for one week. A2B5$^+$ OPCs are prepared as described above and then added into the cultured neocortical neurons. One day later, different concentrations of an S1P4 receptor antagonist and control reagents are applied into the co-cultures. Fresh media containing the different concentrations of an S1P4 receptor antagonist or control compounds are supplied every three days. After ten days, co-cultures are subjected to sodium dodecyl sulfate polyacrylamide gel electrophoresis (SDS-PAGE)/Western blot analyses to quantify MAG, MBP, and MOG.

Remyelination Assay in Brain Slice Culture

Approximately three to four consecutive 300 µm slices are taken from the junction of the corpus callosum to the hippocampus in post-natal, day 17 Sprague Dawley rats (Charles River, Willmington, Mass.). Slices are cultured in basal DMEM supplemented with 25% horse serum for three days, before being treated with 6 mg/mL LPC (Sigma L-4129) for a further three days. The medium is then changed, and slices incubated with medium containing an S1P4 receptor antagonist or vehicle control for a final period of three days, after which myelination is visualized by black gold staining (Millipore, Bedford, Mass.) following the manufacture's protocol. Images are acquired using a Leica M420 microscope (Bannockburn, Ill.) and the staining intensity of corpus callosum is analyzed using Metamorph software (Molecular Devices, Downingtown, Pa.). Three or four brain slices are used for each treatment group.

Lysolecithin Demyelination Model

Adult Sprague Dawley rats (220-260 g) are anesthetized by intraperitoneal injection of a cocktail, consisting of Ketamine (35 mg/kg), Xylazine (6 mg/kg) and Acepromazine (1 mg/kg). The back of the animal is shaved from the lower thoracic to the lumbar region, subsequently sanitized with 70% isopropanol, Betadine Scrub solution, and 70% isopropanol again. The animal is then placed onto stereotaxic frame.

After ensuring an adequate anesthetic level, the skin is incised along the midline over the thoracic region. The dorsal fascia is incised and the paraspinal muscles separated from the spinous processes of the thoracic vertebrae T-9 through T-11. The T-10 vertebra is demolished, and the lamina removed with micro-rongeurs. Once the dorsal spinal cord region is exposed, a microcapillary glass needle is inserted into the dorsal column to a depth of 0.6 mm. The demyelinating reagent, 1.5 µL of 1% Lysolecithin (LPC, Sigma#L1381) in saline is injected with the infusion rate of 2 nL/sec controlled by a micro-pump (World Precision Instrument #micro4). Once the injection is completed, the needle is placed for additional 1 min before removal. The paraspinal muscles and the lumbar fascia are closed with suture (#5, silk). The skin incision is closed with wound clips. Animals are allowed to recover from the anesthesia and are observed in the humidified incubator.

Buprenorphine (0.05 mg/kg) is administrated subcutaneously (s.c.) twice a day for additional two days following operation.

Three days following the primary surgery, treatments with an S1P4 receptor antagonist (30 pmol), LPA (30 pmol) or control (0.1% DMSO in saline) are injected at the primary injection region in a volume of 1.5 µL with the same infusion speed as indicated above. Nine days following the primary surgery, the animals are anesthetized and perfused transcardially with heparin (10 iu/mL) in saline followed by 4% PFA in PBS. The spinal cords are removed and post fixed in PFA overnight. Then the cords are cut into 100 µM thickness longitudinally and then 1% loxuol fast blue is stained and histological evaluation for remyelination and repair is assessed under microscope.

For systemic treatment, the animals are administered once daily intraperitoneally with either an S1P4 receptor antagonist (10 mg/kg) or control (15% HPCD (hydroxypropyl-β-cyclodextrin)) 2 days following the primary surgery. Nine days after the primary surgery, animals are sacrificed and the spinal cords were processed as indicated above.

In Vivo Screening Assays

Measurement of circulating lymphocytes: Compounds are dissolved in 30% HPCD. Mice (C57bl/6 male, 6-10 week-old) are administered 0.5 and 5 mg/kg of a compound via oral gavage 30% HPCD is included as a negative control.

Blood is collected from the retro-orbital sinus 5 and 24 hours after drug administration under short isoflurane anesthesia. Whole blood samples are subjected to hematology analysis. Peripheral lymphocyte counts are determined using an automated analyzer (HEMAVET™ 3700). Subpopulations of peripheral blood lymphocytes are stained by fluorochrome-conjugated specific antibodies and analyzed using a fluorescent activating cell sorter (FACSCALIBUR™). Three mice are used to assess the lymphocyte depletion activity of each compound screened.

Compounds of formula (I) can induce full lymphopenia at times as short as 4 hours or less to as long as 48 hours or more; for example, 4 to 36 hours, or 5 to 24 hours. In some cases, a compound of formula can induce full lymphopenia at 5 hours and partial lymphopenia at 24 hours. The dosage required to induce lymphopenia can be in the range of, e.g., 0.001 mg/kg to 100 mg/kg; or 0.01 mg/kg to 10 mg/kg. The dosage can be 10 mg/kg or less, such as 5 mg/kg or less, 1 mg/kg or less, or 0.1 mg/kg or less.

CFA Inflammatory Pain Model

In the CFA (complete Freund's adjuvant) model, adult male SD (250-300 g) rats are anesthetized with isoflurane inhalation (4.5% induction/2.0% maintenance). Heat-killed M. Tuberculosis H37 RA (non-viable) suspended at a concentration of 1.0 mg/ml in incomplete Freund's adjuvant is used (Chondrex Inc., catalog#7008). At day 0, intradermal injection (i.d.) of 100 μl of CFA (1:1 oil/saline) is slowly perfused into the right footpad of the rats. At day 1, baseline tactile allodynia test are conducted: rats that develop sensitive painful response are enrolled to the study. At day 2, rats are orally dosed once with either vehicle or test compound, then at 2 hrs, 4 hrs, 6 hrs and 24 hrs after dosage, all rats are tested for mechanical allodynia response.

Tactile allodynia is tested as follows. A rat is placed in an elevated Plexiglas observation chamber (approximately 4"×6"×10") having a wire grid (1 cm² spacing) mesh floor under polycarbonate cages. The rat is left to acclimate to the experimental conditions for 20 minutes before testing begins. After the rat is calm, tactile allodynia is assessed using a series of von Frey filaments ranging from 2.04-28.84 g (Stoelting, Wood Dale, Ill.). Graded pressure is presented to a localized area on the plantar surface of the paw via the use of Von Frey hairs (monofilaments which are calibrated to bend at a known pressure). A response to the VonFrey hair is recorded as the rat withdrawing the tested paw and is usually followed by lifting and licking. A series of filaments are used to determine the threshold response using the established "Up-Down" method. Each paw is tested 4-6 times repeatedly with 1-2 seconds (modified from Seltzer et al., 1991) in between each probe to accurately assess the behavior. A sharp lifting of the paw is scored as a positive response.

Rat Model of Neuropathic Pain

Chronic Constriction Injury (CCI) Surgery: In the CCI model (Bennett and Xie, *Pain*, 1989, which is incorporated by reference in its entirety), adult male SD (250-275 g) rats are anesthetized with isoflurane inhalation (4.5% induction/2.0% maintenance). The surgery is performed under aseptic conditions and involves exposing the sciatic nerve at the mid-thigh level. Ocular lubricant is used as needed to prevent corneal drying. After shaving and disinfecting the skin (betadine followed by 70% ethanol), a small incision is made just caudal to the biceps femoris. Care is taken to not disturb the sciatic nerve. The nerve is slightly elevated, and 4 loose ligatures of 4-0 chromic gut suture are inserted under the nerve, and then are loosely tied around it. The sutures constrict the nerve but do not strangle it. Prior to inserting the chromic gut, it is rinsed twice in sterile saline. The incision is closed with wound clips, and rats are allowed to recover from anesthesia on a circulating water heating pad before being returned to their home cages. In the sham controls the skin is opened, and the sciatic nerve is identified and elevated, but no sutures are tied around the nerve. All rats are screened for pain response around post-surgery day 7 and only rats with sensitive pain response are enrolled to the study.

Animals are orally dosed twice/day for 3 times/week with either vehicle or test compound post-surgery at days 10, 12, 14, 17, 19 and 21, and animals are also tested at the same schedule for three types of neuropathic pain: thermal hyperalgesia, tactile allodynia and incapacitance.

(1) Plantar thermal hyperalgesia: Rats are tested for hyperalgesia using a plantar device (Ugo Basile Inc., Cat.#37370). After acclimation to the testing room, rats are placed on an elevated glass floor beneath inverted clear plastic cages, and a radiant heat source beneath the glass is aimed at the mid-plantar surface of the hindpaw after they have ceased all exploratory behavior. The onset of light activates a timer, which is terminated by a hindpaw withdrawal response. A cutoff time of 30 seconds is used to avoid tissue damage in the absence of a response. The average withdrawal latency value of three trials from the ipsilateral hindpaw is measured with at least 5-10 minutes between each trial to avoid any tissue damage.

(2) Tactile allodynia is tested as described above.

(3) Incapacitance: The incapacitance test measures the weight the rat places on each of its hindpaws. The rat is placed in a small, clear Plexiglas box (6" long×3" wide×4" tall). The box is tilted up and opens in the front. The rat is placed in the box so that its hindpaws are at the back (lower) portion of the box, and the forepaws are at the front (raised) part of the box. The rat's head is at the opening in the front of the box. The box is placed on a divided scale such that each of the rat's hindpaws is on one of the two weighing pans of the scale. The weight that the rat placed on each hindpaw is then measured. The procedure is rapid (about 10 sec) and does not cause the animal any pain.

Other embodiments are within the scope of the following claims.

What is claimed is:
1. A compound represented by formula (I):

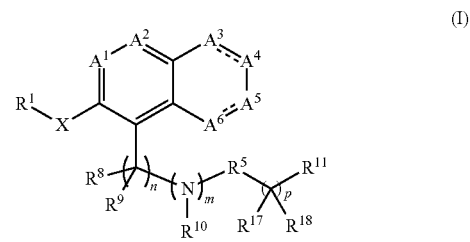

or a pharmaceutically acceptable salt thereof, wherein:
X is O, S(O)$_r$, NR$^{12}$, C(O) or CH$_2$;
A$^1$ is CR$^2$;
A$^2$ is CR$^3$;
A$^3$, A$^4$, A$^5$ and A$^6$ are each independently CR$^2$ or C(R$^2$),
"- - - - -" indicates a double or a single bond;

R$^1$ is a C$_{6-20}$alkyl, a C$_{3-14}$carbocyclyl, a 3- to 15-membered heterocyclyl, a C$_{6-10}$aryl, or a five- to 14-membered heteroaryl, wherein the heterocyclyl and the heteroaryl comprise from 1 to 10 heteroatoms independently selected from N, S or O, and wherein R$^1$ may be optionally substituted with from one to six independently selected R$^6$;

R$^2$ and R$^3$, for each occurrence, are independently selected from the group consisting of hydrogen, halo, hydroxyl, nitro, cyano, carboxy, C$_{1-6}$alkyl, C$_{1-6}$haloalkyl, C$_{3-8}$cycloalkyl, C$_{3-8}$halocycloalkyl, C$_{1-6}$alkoxy, C$_{1-6}$haloalkoxy, C$_{3-8}$cycloalkoxy, C$_{3-8}$halocycloalkoxy, C$_{1-6}$alkanoyl, amino, N—(C$_{1-6}$alkyl)amino, N,N-di-(C$_{1-6}$alkyl)amino, C$_{1-6}$alkoxycarbonyl, C$_{1-6}$alkanoyloxy, carbamoyl, N—(C$_{1-6}$alkyl)carbamoyl, N,N-di-(C$_{1-6}$alkyl)carbamoyl, C$_{1-6}$alkylamido, mercapto, C$_{1-6}$alkylthio, C$_{1-6}$alkylsulfonyl, sulfamoyl, N—(C$_{1-6}$alkyl)sulfamoyl, N,N-di-(C$_{1-6}$alkyl)sulfamoyl, and C$_{1-6}$alkylsulfonamido;

R$^5$ is a C$_{1-6}$alkyl, C$_{3-8}$carbocyclyl, a 3- to 8-membered heterocyclyl, C$_{6-10}$aryl, a 5- to 10-membered heteroaryl, a bridged ring system comprising from 6 to 12 ring members, a spiro ring system comprising from 5-14 ring members; or a bicyclic ring system represented by the following formula:

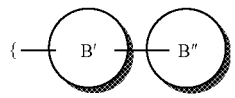

wherein B' and B" are independently selected from the group consisting of monocyclic C$_{3-8}$carbocyclyl, a monocyclic 3- to 8-membered heterocyclyl, phenyl or a 5- to 6- membered heteroaryl; wherein R$^5$ may be optionally substituted with from 1 to 4 independently selected R$^7$;

R$^6$, for each occurrence, is independently selected from the group consisting of halo, C$_{1-6}$alkyl, C$_{1-6}$alkoxy, C$_{1-6}$haloalkyl, C$_{3-8}$cycloalkyl, C$_{6-10}$aryl, C$_{1-6}$alkoxy-C$_{1-6}$alkyl, and tri-(C$_{1-6}$alkyl)silyl; or two R$^6$ that are attached to the same carbon atom may form C$_{3-8}$spirocycloalkyl or 3- to 8-membered spiroheterocyoalkyl;

R$^7$, for each occurrence, is independently halo, hydroxyl, nitro, cyano, C$_{1-6}$alkyl, C$_{1-6}$haloalkyl, C$_{1-6}$alkoxy, C$_{1-4}$haloalkoxy, C$_{2-6}$alkenyl, C$_{2-6}$alkynyl, C$_{3-8}$cycloalkyl, C$_{3-8}$halocycloalkyl, C$_{3-8}$cycloalkoxy, C$_{3-8}$halocycloalkoxy, —NR$^a$R$^b$, —C(O)NR$^a$R$^b$, —N(R$^a$)C(O)R$^b$, —C(O)R$^a$, —S(O)$_r$R$^a$, or —N(R$^a$)S(O)$_2$R$^b$;

R$^8$ and R$^9$ are each independently hydrogen, a carboxy, C$_{1-6}$alkyl, or a C$_{2-6}$alkenyl; or R$^8$ and R$^9$ together with the carbon to which they are attached are —C(═O)—, a C$_{3-8}$spirocycloalkyl, or a 3- to 8-membered spiroheterocycloalkyl;

R$^{10}$ and R$^{12}$ are each, independently, hydrogen or a C$_{1-6}$alkyl;

R$^{11}$ is —OH, —C(O)OR$^{15}$, —C(O)N(R$^{16}$)$_2$, —C(O)N(R$^{15}$)—S(O)$_2$R$^{15}$, —S(O)$_2$OR$^{15}$, —C(O)NHC(O)R$^{15}$, —Si(O)OH, —B(OH)$_2$, —N(R$^{15}$)S(O)$_2$R$^{15}$, —S(O)$_2$N(R$^{15}$)$_2$, —O—P(O)(OR$^{15}$)$_2$, —P(O)(OR$^{15}$)$_2$, —CN, —S(O)$_2$NHC(O)R$^{15}$, —C(O)NHS(O)$_2$R$^{15}$, —C(O)NHOH, —C(O)NHCN, or a heteroaryl or a heterocyclyl selected from the group consisting of formulae (a)-(i'):

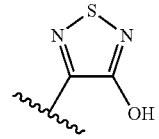 (a)

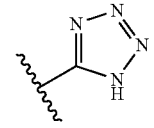 (b)

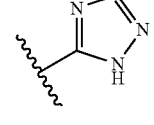 (c)

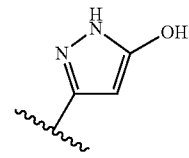 (d)

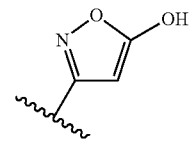 (e)

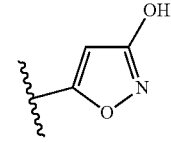 (f)

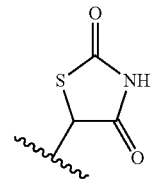 (g)

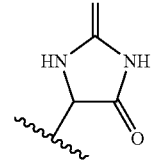 (h)

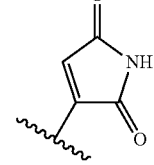 (i)

-continued
(j) 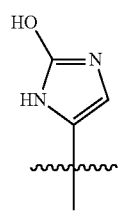
(k) 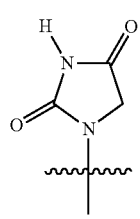
(l) 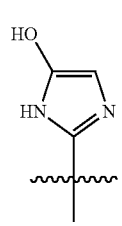
(m) 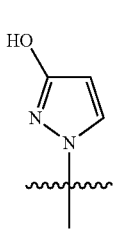
(n) 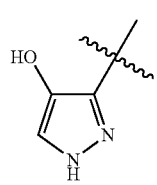
(o) 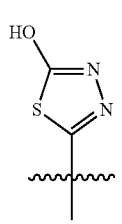
(p) 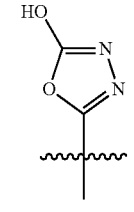
-continued
(q) 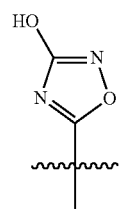
(r) 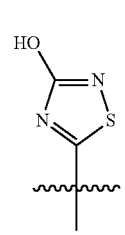
(s) 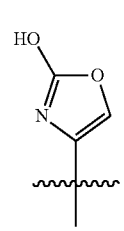
(t) 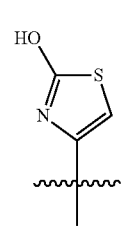
(u) 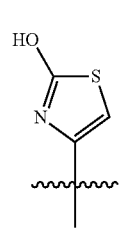
(v) 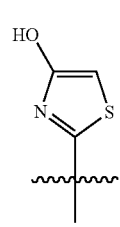
(w) 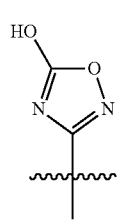

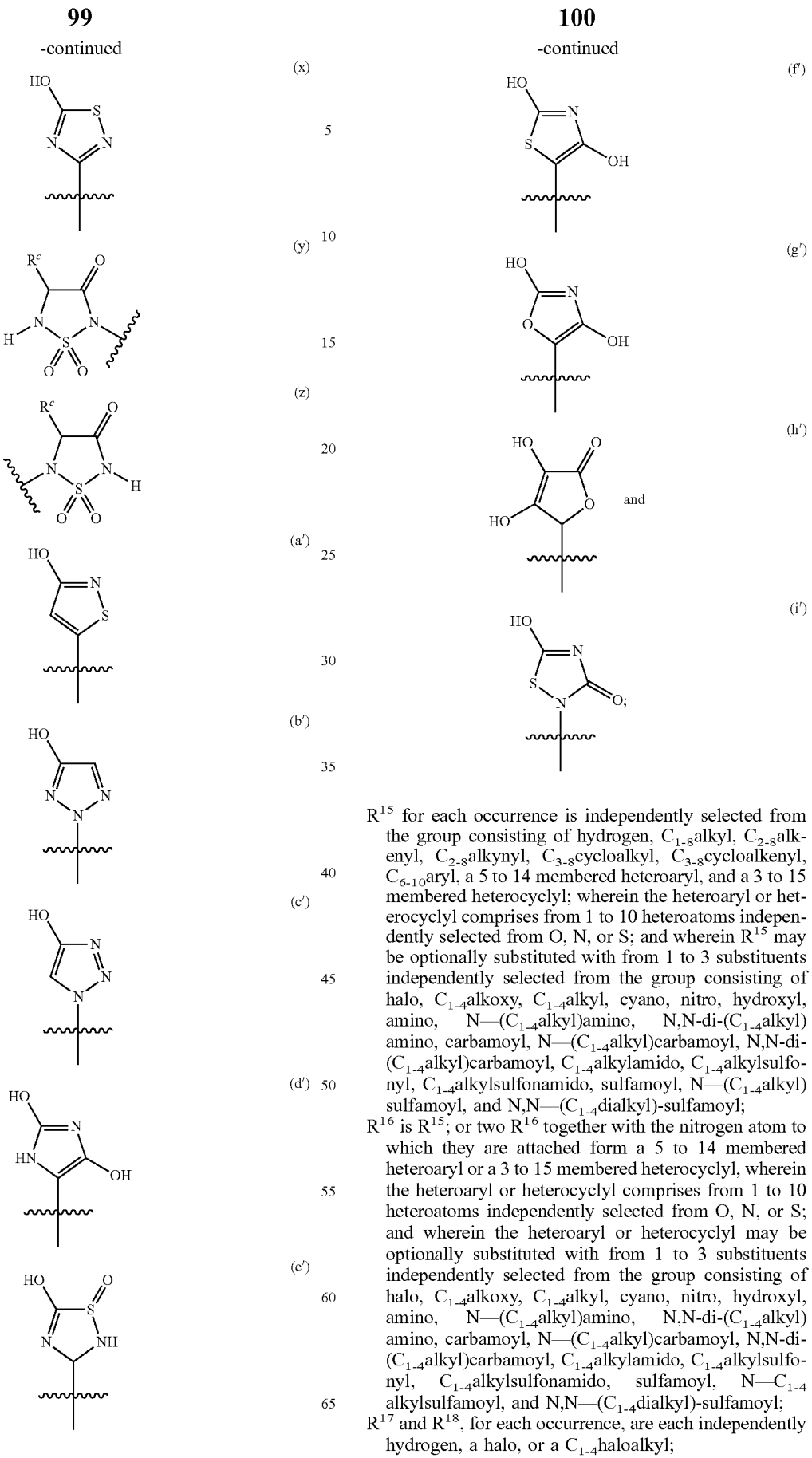

$R^{15}$ for each occurrence is independently selected from the group consisting of hydrogen, $C_{1-8}$alkyl, $C_{2-8}$alkenyl, $C_{2-8}$alkynyl, $C_{3-8}$cycloalkyl, $C_{3-8}$cycloalkenyl, $C_{6-10}$aryl, a 5 to 14 membered heteroaryl, and a 3 to 15 membered heterocyclyl; wherein the heteroaryl or heterocyclyl comprises from 1 to 10 heteroatoms independently selected from O, N, or S; and wherein $R^{15}$ may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—($C_{1-4}$alkyl)sulfamoyl, and N,N—($C_{1-4}$dialkyl)-sulfamoyl;

$R^{16}$ is $R^{15}$; or two $R^{16}$ together with the nitrogen atom to which they are attached form a 5 to 14 membered heteroaryl or a 3 to 15 membered heterocyclyl, wherein the heteroaryl or heterocyclyl comprises from 1 to 10 heteroatoms independently selected from O, N, or S; and wherein the heteroaryl or heterocyclyl may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—$C_{1-4}$alkylsulfamoyl, and N,N—($C_{1-4}$dialkyl)-sulfamoyl;

$R^{17}$ and $R^{18}$, for each occurrence, are each independently hydrogen, a halo, or a $C_{1-4}$haloalkyl;

R¹⁹ for each occurrence is independently selected from the group consisting of hydrogen, carboxy, $C_{1-6}$alkyl, $C_{1-6}$haloalkyl, $C_{3-8}$cycloalkyl, $C_{3-8}$halocycloalkyl, $C_{1-6}$alkanoyl, $C_{1-6}$alkoxycarbonyl, carbamoyl, N—($C_{1-6}$alkyl)carbamoyl, N,N-di-($C_{1-6}$alkyl)carbamoyl, $C_{1-6}$alkylsulfonyl, sulfamoyl, N—($C_{1-6}$alkyl)sulfamoyl, and N,N-di-($C_{1-6}$alkyl)sulfamoyl;

$R^a$ and $R^b$, for each occurrence, are independently hydrogen, $C_{1-6}$alkyl, $C_{2-6}$alkenyl, $C_{2-6}$alkynyl, $C_{3-8}$cycloalkyl, $C_{6-10}$aryl, or $C_{3-8}$halocycloalkyl;

$R^c$ is hydrogen or a $C_{1-4}$alkyl;

m is 0 or 1, provided that when m is 0, $R^5$ comprises at least one nitrogen;

n is an integer from 1 to 6;

p is 0 or an integer from 1 to 6, and r, for each occurrence, is independently 0, 1, or 2, provided that the compound is not methyl 2-(((2-((4-(tert-butyl)cyclohexyl)oxy)-4-methylnaphthalen-1-yl)methyl)amino)acetate;

2-(((2-((4-(tert-butyl)cyclohexyl)oxy)-4-methylnaphthalen-1-yl)methyl)amino)acetic acid;

4-(((2-((4-(tert-butyl)cyclohexyl)oxy)-4-methylnaphthalen-1-yl)methyl) amino)butanoic acid;

methyl 1-((2-((4-(tert-butyl)cyclohexyl)oxy)-4-methylnaphthalen-1-yl)methyl)azetidine-3-carboxylate;

1-((2-((4-(tert-butyl)cyclohexyl)oxy)-4-methylnaphthalen-1-yl)methyl)azetidine-3-carboxylic acid;

ethyl 3-(((2-((4-(tert-butyl)cyclohexyl)oxy)-4-methylnaphthalen-1-yl)methyl)amino)propanoate;

3-(((2-((4-(tert-butyl)cyclohexyl)oxy)-4-methylnaphthalen-1-yl)methyl)amino)propanoic acid;

methyl 1-((2-((4-(tert-butyl)cyclohexyl)oxy)-4-methylnaphthalen-1-yl)methyl)pyrrolidine-3-carboxylate; or 1-((2-((4-(tert-butyl)cyclohexyl)oxy)-4-methylnaphthalen-1-yl)methyl)pyrrolidine-3-carboxylic acid.

2. The compound of claim 1, or a pharmaceutically acceptable salt thereof, wherein $R^3$ is a halo, $C_{1-6}$alkyl, $C_{1-6}$haloalkyl or cyano.

3. The compound of claim 1, or a pharmaceutically acceptable salt thereof, wherein $R^5$ is substituted by —$(CR^{17}R^{18})_p$—$R^7$ and is optionally substituted by from 1 to 3 independently selected $R^{11}$.

4. The compound of claim 1, or a pharmaceutically acceptable salt thereof, wherein $R^1$ is a cyclohexyl which is optionally substituted with from one to three independently selected $R^6$.

5. The compound of claim 4, or a pharmaceutically acceptable salt thereof, wherein m is 1 and $R^5$ is $C_{1-6}$alkyl.

6. The compound of claim 4, or a pharmaceutically acceptable salt thereof, wherein
m is 0; and
$R^5$ is selected from the group consisting of:

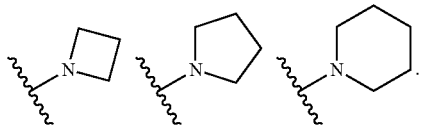

7. The compound of claim 5, or a pharmaceutically acceptable salt thereof, wherein $R^7$ is COOH.

8. The compound of claim 1, or a pharmaceutically acceptable salt thereof, wherein $A^4$ and $A^6$ are each independently $CR^2$.

9. The compound of claim 1, or a pharmaceutically acceptable salt thereof, wherein X is O.

10. A compound selected from the group consisting of:
3-(((2-(((trans)-4-(tert-butyl)cyclohexyl)oxy)-4-iodonaphthalen-1-yl)methyl)amino)propanoic acid;
1-((2-(trans-4-tert-butylcyclohexyloxy)-4-methylnaphthalen-1-yl)methyl)-4-methylpiperidine-4-carboxylic acid;
4-(((2-((trans-4-(tert-butyl)cyclohexyl)oxy)-4-methylnaphthalen-1-yl)methyl)amino)bicyclo[2.2.2]octane-1-carboxylic acid;
3-(((2-((trans-4-(tert-butyl)cyclohexyl)oxy)-4-methylnaphthalen-1-yl)methyl)amino)cyclobutanecarboxylic acid;
4-(((2-((trans-4-(tert-butyl)cyclohexyl)oxy)-4-methylnaphthalen-1-yl)methyl)amino)cyclohexanecarboxylic acid;
3-(((2-((trans-4-(tert-butyl)cyclohexyl)oxy)-4-methylnaphthalen-1-yl)methyl)amino)cyclopentanecarboxylic acid;
2-(1-((2-((trans-4-(tert-Butyl)cyclohexyl)oxy)-4-methylnaphthalen-1-yl)methyl)piperidin-4-yl)acetic acid;
2-(1-((2-((trans-4-(tert-butyl)cyclohexyl)oxy)-4-methylnaphthalen-1-yl)methyl)azetidin-3-yl)acetic acid;
2-(1-((2-((trans-4-(tert-butyl)cyclohexyl)oxy)-4-methylnaphthalen-1-yl)methyl)pyrrolidin-3-yl)acetic acid;
1-((2-(cyclohexyloxy)-4-methylnaphthalen-1-yl)methyl)piperidine-4-carboxylic acid;
1-((4-methyl-2-((trans-4-(tert-pentyl)cyclohexyl)oxy)naphthalen-1-yl)methyl)piperidine-4-carboxylic acid;
1-((4-methyl-2-((trans-4-phenylcyclohexyl)oxy)naphthalen-1-yl)methyl)piperidine-4-carboxylic acid;
1-((4-methyl-2-(spiro[4.5]decan-8-yloxy)naphthalen-1-yl)methyl)piperidine-4-carboxylic acid;
1-((4-methyl-2-(spiro[5.5]undecan-3-yloxy)naphthalen-1-yl)methyl)piperidine-4-carboxylic acid;
1-((2-((cis-4-(tert-Butyl)cyclohexyl)oxy)-4-methylnaphthalen-1-yl)methyl)piperidine-4-carboxylic acid;
1-((4-methyl-2-((cis-4-methylcyclohexyl)oxy)naphthalen-1-yl)methyl)piperidine-4-carboxylic acid;
1-((2-((cis-4-Ethylcyclohexyl)oxy)-4-methylnaphthalen-1-yl)methyl)piperidine-4-carboxylic acid;
1-((4-Methyl-2-((cis-4-phenylcyclohexyl)oxy)naphthalen-1-yl)methyl)piperidine-4-carboxylic acid;
1-((4-methyl-2-((trans-4-(trimethylsilyl)cyclohexyl)oxy)naphthalen-1-yl)methyl)piperidine-4-carboxylic acid;
1-((4-methyl-2-((cis-4-(trimethylsilyl)cyclohexyl)oxy)naphthalen-1-yl)methyl)piperidine-4-carboxylic acid;
1-((2-(((trans)-4-(tert-butyl)cyclohexyl)oxy)-4-(trifluoromethyl)naphthalen-1-yl)methyl)piperidine-4-carboxylic acid;
1-((2-(((trans)-4-(tert-butyl)cyclohexyl)oxy)-4-iodonaphthalen-1-yl)methyl)piperidine-4-carboxylic acid;
1-((2-(((trans)-4-(tert-butyl)cyclohexyl)oxy)-4-chloronaphthalen-1-yl)methyl)piperidine-4-carboxylic acid;
(R)-1-((6-(((trans-4-(tert-Butyl)cyclohexyl)oxy)-8-methylnaphthalen-2-yl)methyl)pyrrolidine-3-carboxylic acid;
(S)-1-((2-(((trans)-4-(tert-butyl)cyclohexyl)oxy)-4-methylnaphthalen-1-yl)methyl)pyrrolidine-3-carboxylic acid; and
1-((2-(((trans)-4-(tert-butyl)cyclohexyl)oxy)-4-methylnaphthalen-1-yl)methyl)piperidine-4-carboxylic acid;
or a pharmaceutically acceptable salt thereof.

11. A pharmaceutical composition comprising a pharmaceutically acceptable carrier or excipient and a compound according to claim 1, or a pharmaceutically acceptable salt thereof.

12. A method of treating or reducing symptoms of a condition in a mammal comprising administering said mammal an effective amount of a compound of claim 1, wherein the condition is multiple sclerosis in a mammal.

13. The method of claim 12, wherein the condition is multiple sclerosis.

14. The method of claim 12, further comprising administering to said mammal an effective amount of one or more drugs selected from the group consisting of: a corticosteroid, a bronchodilator, an antiasthmatic, an antiinflammatory, an antirheumatic, an immunosuppressant, an antimetabolite, an immunomodulating agent, an antipsoriatic, and an antidiabetic.

15. A method of treating, or reducing chronic pain in a mammal comprising administering to said mammal an effective amount of a compound according to claim 1, or a pharmaceutically acceptable salt thereof.

16. The method of claim 15, wherein the chronic pain is inflammatory pain.

17. The method of claim 15, wherein the chronic pain is neuropathic pain.

18. The compound of claim 6, wherein $R^7$ is COOH.

* * * * *